(12) United States Patent
Bissantz et al.

(10) Patent No.: US 7,498,339 B2
(45) Date of Patent: Mar. 3, 2009

(54) SPIROPIPERIDINE GLYCINAMIDE DERIVATIVES

(75) Inventors: Caterina Bissantz, Village-Neuf (FR); Erwin Goetschi, Reinach BL (CH); Christophe Grundschober, Rodersdorf (CH); Raffaello Masciadri, Zürich (CH); Hasane Ratni, Habsheim (FR); Mark Rogers-Evans, Oberwil BL (CH); Patrick Schnider, Bottmingen (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/969,975

(22) Filed: Jan. 7, 2008

(65) Prior Publication Data

US 2008/0171759 A1 Jul. 17, 2008

(30) Foreign Application Priority Data

Jan. 12, 2007 (EP) .................................. 07100486

(51) Int. Cl.
*A61K 31/438* (2006.01)
*C07D 491/107* (2006.01)

(52) U.S. Cl. .................. 514/278; 546/17; 544/124; 544/360; 514/232.8; 514/253

(58) Field of Classification Search ................. 514/278, 514/232.8, 253; 546/17; 544/124, 360
See application file for complete search history.

(56) References Cited

U.S. PATENT DOCUMENTS

| 3,370,091 A | 2/1968 | Archer et al. |
| 3,531,467 A | 9/1970 | Archer et al. |
| 2004/0260100 A1 | 12/2004 | Ku et al. |

FOREIGN PATENT DOCUMENTS

| EP | 0718280 | 6/1996 |
| WO | WO 93/025527 | 12/1993 |
| WO | WO 2004/022528 | 3/2004 |
| WO | WO 2004/026855 | 4/2004 |
| WO | WO 2004/069809 | 8/2004 |
| WO | WO 2005/046682 | 5/2005 |
| WO | WO 2007/006688 | 1/2007 |

OTHER PUBLICATIONS

Ebner et al., Eur. J. Neurosci. vol. 15, pp. 384-388 (2002).
Bielsky et al., Neuropsychopharmacology vol. 29, pp. 483-493 (2004).
Liebsch et al., Regulatory Peptides vol. 59, Issue 2, pp. 229-239 (1995).
Michelini et al., Ann. NY Acad. Sci. vol. 897, pp. 198-211 (1999).
Vankerckhoven et al., Eur. J. Pharmacol. vol. 449, Issue 1-2, pp. 135-141 (2002).
Abdel-Magid, A. F.; Carson, K. G.; Harris, B. D.; Maryanoff, C. A.; Shah, R. D. J. Org. Chem. 1996, 61, 3849-3862.
Mattson, R. J.; Pham, K. M.; Leuck, D. J.; Cowen, K. A. J. Org. Chem. 1990, 55, 2552-2554.
Lecointe, L.; Rolland, V.; Pappalardo, L.; Roumestant, M. L.; Viallefont, P.; Martinez, J. Journal of Peptide Research 2000, 55, 300-307.
Baeza, A.; Najera, C.; de Gracia Retamosa, M.; Sansano, J. M. Synthesis 2005, 2787-2797.
Deuchert, K.; Hertenstein, U.; Huenig, S.; Wehner, G. Chem. Ber. 1979, 112, 2045-2061.
Dejaegher, Y.; Mangelinckx, S.; De Kimpe, N. Synlett 2002, 113-115.
Grisar, J. M.; Claxton, G. P.; Wiech, N. L.; Lucas, R. W.; MacKenzie, R. D.; Goldstein, S. J Med. Chem. 1973, 16, 885-893.
Brenner, D. G.; Cavolowsky, K. M.; Shepard, K. L. J. Heterocyclic Chem. 1985, 22, 805-808.
Sasse, A.; Stark, H.; Ligneau, X.; Elz, S.; Reidemeister, S.; Ganellin, C. R.; Schwartz, J. C.; Schunack, W. Bioorganic & Medicinal Chemistry 2000, 8, 1139-1149.
Terrasson, V.; Marque, S.; Scarpacci, A.; Prim, D. Synthesis 2006, 1858-1862.
Fryer, R. I.; Earley, J. V.; Zally, W. J. Heterocyclic Chem. 1967, 4, 149-150.
Walker, G. N.; Smith, R. T. J. Org. Chem. 1970, 36, 305-308.
Walser, A.; Flynn, T.; Fryer, R. I. J. Heterocyclic Chem. 1974, 11, 885-888.
Fryer, R. I.; Earley, J. V. J. Heterocyclic Chem. 1977, 14, 1435-1437.
Clerici, A.; Porta, O. J. Org. Chem. 1982, 47, 2852-2856.
Clerici, A.; Porta, O. J. Org. Chem. 1993, 58, 2889-2893.
Pfoertner, K. H.; Montavon, F.; Bernauer, K. Helv. Chim. Acta 1985, 68, 600-605.
Serradeil-Le Gal et al, *Elsevier*, 139 (2002) 197-210 XP001205440.

*Primary Examiner*—Charanjit S Aulakh
(74) *Attorney, Agent, or Firm*—George W. Johnston; Patricia S. Rocha-Tramaloni; Kimberly J. Prior

(57) ABSTRACT

In particular, the present invention is concerned with compounds of the general formula (I)

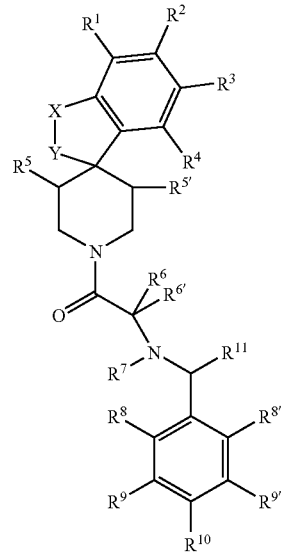

wherein X, Y and $R^1$ to $R^{10}$ are as described herein. The compounds are V1a receptor antagonists. The invention also relates to the manufacture of compounds of formula I, pharmaceutical compositions containing them and their use for the treatment of anxiety and depressive disorders and other diseases.

19 Claims, No Drawings

SPIROPIPERIDINE GLYCINAMIDE DERIVATIVES

PRIORITY TO RELATED APPLICATION(S)

This application claims the benefit of European Patent Application No. 07100486.5, filed Jan. 12, 2007, which is hereby incorporated by reference in its entirety.

BACKGROUND OF THE INVENTION

Vasopressin is a 9 amino acid peptide mainly produced by the paraventricular nucleus of the hypothalamus. Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water excretion and mediates the antidiuretic effects of vasopressin.

In the periphery vasopressin acts as a neurohormone and stimulates vasoconstriction, glycogenolysis and antidiuresis. In the brain vasopressin acts as a neuromodulator and is elevated in the amygdala during stress (Ebner, K., C. T. Wotjak, et al. (2002). "Forced swimming triggers vasopressin release within the amygdala to modulate stress-coping strategies in rats." Eur J Neurosci 15(2): 384-8). The V1a receptor is extensively expressed in the brain and particularly in limbic areas like the amygdala, lateral septum and hippocampus which are playing an important role in the regulation of anxiety. Indeed V1a knock-out mouse show a reduction in anxious behavior in the plus-maze, open field and light-dark box (Bielsky, I. F., S. B. Hu, et al. (2003). "Profound Impairment in Social Recognition and Reduction in Anxiety-Like Behavior in Vasopressin V1a Receptor Knockout Mice." Neuropsychopharmacology). The downregulation of the V1a receptor using antisense oligonucleotide injection in the septum also causes a reduction in anxious behavior (Landgraf, R., R. Gerstberger, et al. (1995). "V1 vasopressin receptor antisense oligodeoxynucleotide into septum reduces vasopressin binding, social discrimination abilities, and anxiety-related behavior in rats." Regul Pept 59(2): 229-39).

The V1a receptor is also mediating the cardiovascular effects of vasopressin in the brain by centrally regulating blood pressure and heart rate in the solitary tract nucleus (Michelini, L. C. and M. Morris (1999). "Endogenous vasopressin modulates the cardiovascular responses to exercise." Ann N Y Acad Sci 897: 198-211). In the periphery it induces the contraction of vascular smooth muscles and chronic inhibition of the V1a receptor improves hemodynamic parameters in myocardial infarcted rats (Van Kerckhoven, R., I. Lankhuizen, et al. (2002). "Chronic vasopressin V(1A) but not V(2) receptor antagonism prevents heart failure in chronically infarcted rats." Eur T Pharmacol 449(1-2): 135-41)

SUMMARY OF THE INVENTION

The present invention provides novel spiropiperidine glycinamide derivatives as V1a receptor antagonists, their manufacture, pharmaceutical compositions containing them and their use for the treatment of anxiety and depressive disorders and other diseases.

In particular, the present invention provides compounds of formula (I)

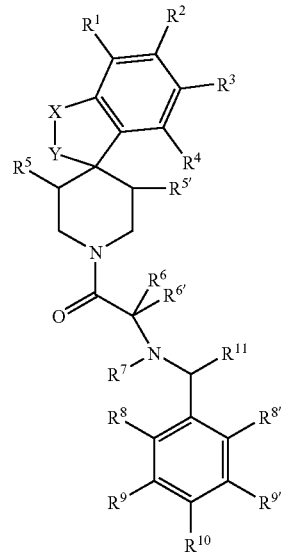

wherein
X and Y are selected from the combinations of
X is $CH_2$, and Y is O,
X is C=O, and Y is O,
X is O, and Y is $CH_2$,
X is $NR^7$, and Y is C=O,
X is $NR^7$, and Y is $CH_2$,
X—Y is —C=C—, or
X—Y is —$CH_2CH_2$—, and
X is O, and Y is C=O;
$R^1$, $R^2$, $R^3$, and $R^4$ are each independently hydrogen, halo, $C_{1-6}$-alkyl, $C_{1-6}$-haloalkyl, $C_{1-6}$-alkoxy, or $C_{1-6}$-haloalkoxy;
$R^5$ and $R^{5'}$ are each independently hydrogen or methyl;
$R^6$ and $R^{6'}$ are each independently hydrogen or methyl;
$R^7$ is hydrogen, $C_{1-6}$-alkyl, —C(O)O—$C_{1-6}$-alkyl, or —C(O)O—$C_{2-6}$-alkenyl;
$R^8$, $R^{8'}$, $R^9$, $R^{9'}$, and $R^{10}$ are each independently selected from
hydrogen,
halogen,
$C_{1-4}$-alkyl, optionally substituted by CN or OH,
$C_{1-4}$-haloalkyl,
$C_{1-4}$-alkoxy,
$C_{1-4}$-haloalkoxy, and
hydroxy;
$R^{11}$ is hydrogen,
$C_{1-6}$-alkyl, optionally substituted by CN, OH or halogen,
—$(CR^iR^{ii})_m$—$R^{iii}$,
wherein $R^i$ and $R^{ii}$ are each independently
H,
OH,
$C_{1-4}$-alkyl, optionally substituted with OH,
or one $R^i$ and one $R^{ii}$ together with the carbon atom to which they are bound form a 3 to 5-membered cycloalkyl,
wherein m is from 0 to 4,
wherein $R^{iii}$ is
phenyl, naphthyl, 5- to 6-membered monocyclic or 9- to 10-membered bicyclic heteroaryl, 3- to 7-membered heterocycloalkyl, or 3- to 7-membered cycloalkyl, each of which is optionally substituted by one or more A,
—C(O)—R$^{iv}$,
  wherein R$^{iv}$ is
    C$_{1-6}$-alkyl, optionally substituted with OH, or CN,
    C$_{1-6}$-alkoxy,
    hydroxy,
    phenyl, naphthyl, benzyl, -Obenzyl, 5- to 6-membered monocyclic or 9- to 10-membered bicyclic heteroaryl, 3- to 7-membered heterocycloalkyl, or 3- to 7-membered cycloalkyl,
      each of which is optionally substituted by one or more A,
—C(O)—NR$^f$R$^g$, or
—NR$^h$R$^j$,
  wherein R$^f$, R$^g$, R$^h$ and R$^j$ are each independently selected from
    hydrogen,
    C$_{1-6}$-alkyl, and
    phenyl or 5- to 6-membered heteroaryl,
      optionally substituted with one or more A,
A is halo, nitro, hydroxy, cyano, =O, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, —(CH$_2$)$_x$—S(O)$_{0-2}$C$_{1-6}$-alkyl, —(C$_{1-6}$-alkylene)-O—C$_{1-6}$-alkyl, —(C$_{1-6}$-alkylene)-O—C$_{1-6}$-haloalkyl, —(CH$_2$)$_x$—NR$^a$R$^b$, —(CH$_2$)$_x$—C(O)NR$^a$R$^b$, —(CH$_2$)$_x$—S(O)$_2$NR$^a$R$^b$, —(CH$_2$)$_x$—R$^c$, —(CH$_2$)$_x$—O—R$^d$, —(CH$_2$)$_x$—S(O)$_{0-2}$—R$^d$, —(CH$_2$)$_x$—NR$^a$R$^d$, —(CH$_2$)$_x$—C(O)—NR$^a$R$^d$, —(CH$_2$)$_x$—C(O)R$^e$, —(CH$_2$)$_x$—NR$^a$S(O)$_2$R$^e$, or —(CH$_2$)$_x$—NR$^a$(CH$_2$)xC(O)R$^e$, wherein
  x is from 0 to 4;
  R$^a$ and R$^b$ are each independently hydrogen or C$_{1-6}$-alkyl,
  R$^c$ is phenyl, 5- to 6-membered heteroaryl, 3- to 7-membered heterocycloalkyl, or 3- to 7-membered cycloalkyl,
  R$^d$ is phenyl or 5- to 6-membered heteroaryl,
  R$^e$ is C$_{1-6}$-alkyl, C$_{1-6}$-alkoxy, phenyl, or 5- to 6-membered heteroaryl, 3- to 7-membered heterocycloalkyl, or 3- to 7-membered cycloalkyl,
    wherein phenyl, 5- to 6-membered heteroaryl, 3- to 7-membered heterocycloalkyl, or 3- to 7-membered cycloalkyl of R$^c$, R$^d$ or R$^e$ are optionally substituted with one, two, or three halo, C$_{1-6}$-haloalkyl, C$_{1-6}$-alkyl, or C$_{1-6}$-alkoxy, or one of R$^8$ or R$^{8'}$ together with R$^{11}$ and the atoms to which they are bound form a 5-membered carbocycle, optionally anellated with benzo,
  wherein the benzo is optionally substituted with one, two or three substituents selected from halo, C$_{1-6}$-haloalkyl, C$_{1-6}$-alkyl, C$_{1-6}$-alkoxy, C$_{1-6}$-haloalkoxy, nitro, hydroxy, and cyano, or a pharmaceutically acceptable salt thereof.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The compounds of formula (I) possess pharmaceutical activity, in particular they are modulators of V1a receptor activity. More particular, the compounds are antagonists of the V1a receptor. Such antagonists are useful as therapeutics in the conditions of dysmenorrhea, hypertension, chronic heart failure, inappropriate secretion of vasopressin, liver cirrhosis, nephrotic syndrome, obsessive compulsive disorder, anxiety and depressive disorders. The preferred indications with regard to the present invention are the treatment of anxiety and depressive disorders.

DETAILED DESCRIPTION OF THE INVENTION

Unless otherwise stated, the following terms used in the present description have the definitions given in the following. It must be noted that, as used in the specification and the appended claims, the singular forms "a", "an," and "the" include plural forms unless the context clearly dictates otherwise.

In the present description, the term "alkyl", alone or in combination with other groups, refers to a branched or straight-chain monovalent saturated hydrocarbon radical. The term "C$_{1-6}$-alkyl" denotes a saturated straight- or branched-chain hydrocarbon group containing from 1 to 6 carbon atoms, for example, methyl, ethyl, n-propyl, isopropyl, n-butyl, isobutyl, tert-butyl, the isomeric pentyls and the like. A preferred sub-group of C$_{1-6}$-alkyl is C$_{1-4}$-alkyl, i.e. with 1-4 carbon atoms.

In the present invention, the term "alkylene" refers to a linear or branched saturated divalent hydrocarbon radical. In particular, "C$_{1-6}$-alkylene", means a linear saturated divalent hydrocarbon radical of one to six carbon atoms or a branched saturated divalent hydrocarbon radical of three to six carbon atoms, e.g. methylene, ethylene, 2,2-dimethylethylene, n-propylene, 2-methylpropylene, 1-methyl-ethylene, 2-methyl-ethylene and the like.

In the present description, the terms "alkoxy" and "C$_{1-6}$-alkoxy" refer to the group R'—O—, wherein R' is alkyl or C$_{1-6}$-alkyl as defined above. Examples of alkoxy groups are methoxy, ethoxy, n-propoxy, isopropoxy, n-butoxy, tert-butoxy, sec-butoxy and the like. A preferred sub-group of C$_{1-6}$-alkoxy, and still more preferred alkoxy groups are methoxy and/or ethoxy.

In the present description, the terms "thioalkyl" and "C$_{1-6}$-thioalkyl" refer to the group R'—S—, wherein R' is alkyl or C$_{1-6}$-alkyl as defined above. The term "—S(O)$_{0-2}$C$_{1-6}$-alkyl" hence refers to the residues —S—C$_{1-6}$-alkyl, —S(O)—C$_{1-6}$-alkyl, and —S(O)$_2$—C$_{1-6}$-alkyl wherein C$_{1-6}$-alkyl is as defined above. Further, the term "—(CH$_2$)$_x$—S(O)$_{0-2}$C$_{1-6}$-alkyl" relates to the residues —(CH$_2$)$_x$—S—C$_{1-6}$-alkyl, —(CH$_2$)$_x$—S(O)—C$_{1-6}$-alkyl, and —(CH$_2$)$_x$—S(O)$_2$—C$_{1-6}$-alkyl wherein x in —(CH$_2$)$_x$—is from 0, 1, 2, 3, or 4.

The term "C$_{1-6}$-alkyl substituted by OH" is synonymous with "C$_{1-6}$-hydroxyalkyl" and "hydroxy-C$_{1-6}$-alkyl" and means a C$_{1-6}$-alkyl group as defined above wherein at least one of the hydrogen atoms of the alkyl group is replaced by a hydroxy group.

The term "C$_{1-6}$-alkyl substituted by CN" is synonymous with "C$_{1-6}$-cyanoalkyl" and "cyano-C$_{1-6}$-alkyl" and means a C$_{1-6}$-alkyl group as defined above wherein at least one of the hydrogen atoms of the alkyl group is replaced by a CN group.

The terms "halo" and "halogen" refer to fluorine (F), chlorine (Cl), bromine (Br) and iodine (I) with fluorine, chlorine and bromine being preferred.

The term "halo-C$_{1-6}$-alkyl" is synonymous with "C$_{1-6}$-haloalkyl" and "C$_{1-6}$-alkyl substitutied by halo" and means a C$_{1-6}$-alkyl group as defined above wherein at least one of the hydrogen atoms of the alkyl group is replaced by a halogen atom, preferably fluoro or chloro, most preferably fluoro. Examples of halo-C$_{1-6}$-alkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Among the preferred halo-$C_{1-6}$-alkyl groups are difluoro- or trifluoro-methyl or -ethyl.

The term "halo-$C_{1-6}$-alkoxy" is synonymous with "$C_{1-6}$-haloalkoxy" and "$C_{1-6}$-alkoxy substitutied by halo" and means a $C_{1-6}$-alkoxy group as defined above wherein at least one of the hydrogen atoms of the alkoxy group is replaced by a halogen atom, preferably fluoro or chloro, most preferably fluoro. Among the preferred halogenated alkoxy groups are difluoro- or trifluoro-methoxy or -ethoxy.

The term "$C_{2-6}$-alkenyl", alone or in combination, denotes a straight-chain or branched hydrocarbon residue of 2 to 6 carbon atoms comprising at least one double bond. Examples of the preferred alkenyl groups are ethenyl, propen-1-yl, propen-2-yl (allyl), buten-1-yl, buten-2-yl, buten-3-yl, penten-1-yl, penten-2-yl, penten-3-yl, penten-4-yl, hexen-1-yl, hexen-2-yl, hexen-3-yl, hexen-4-yl and hexen-5-yl, as well as those specifically illustrated by the examples herein below.

The term "5 or 6 membered heteroaryl" means a monovalent aromatic ring of 5 or 6 ring atoms as ring members containing one, two, three or four ring heteroatoms selected from N, O, and S, the rest being carbon atoms, whereby one, two or three heteroatoms are preferred, and one or two heteroatoms are even more preferred. The attachment point of the monovalent heteroaryl shall be a carbon atom. Examples of heteroaryl moieties include, but are not limited to pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. 5 or 6-membered heteroaryl are optionally substituted with one or more substituents. These optional substitutents include the substituents as described herein, in particular the substituents defined herein as "A". Further, preferred subsitituents are halo, $C_{1-6}$-haloalkyl, $C_{1-6}$-alkyl, $C_{1-6}$-alkoxy, $C_{1-6}$-haloalkoxy, cyano, $C_{1-6}$-cyanoalkyl, —$CH_2OCH_3$, —$S(O)_2$—$C_{1-6}$-alkyl, $C_{1-6}$-hydroxyalkyl, —$C(O)OC_{1-6}$-alkyl, —NHC(O)—$C_{1-6}$-alkyl, —$NHS(O)_2$$C_{1-6}$-alkyl, —$C(O)N(C_{1-6}$-alkyl$)_2$, —$C(O)NH(C_{1-6}$-alkyl), —$S(O)_2N(C_{1-6}$-alkyl$)_2$, or —$S(O)_2NH(C_{1-6}$-alkyl). Particularly preferred are halo, —$CH_2OH$ and $C_{1-6}$-alkyl.

The term "9- to 10-membered bicyclic heteroaryl" means a monovalent aromatic bicyclic ring of 9 or 10 ring atoms as ring members containing one, two, three or four ring heteroatoms selected from N, O, and S, the rest being carbon atoms, whereby one, two or three heteroatoms are preferred, and one or two heteroatoms are even more preferred. The attachment point of the monovalent heteroaryl shall be a carbon atom. Examples of 9- to 10-membered bicyclic heteroaryl moieties include, but are not limited to indolyl, benzoimidazolyl, indazolyl, benzooxazolyl, 1H-pyrrolo[2,3-c]pyridinyl, benzothienyl, benzofuranyl, purinyl, quinolinyl, isoquinolinyl, quinazolinyl, quinoxalinyl, cinnolinyl, phthalazinyl, or pteridinyl. Preferred 9- to 10-membered bicyclic heteroaryl are benzofuranyl, benzothienyl, indolyl, benzoimidazolyl, indazolyl, or benzooxazolyl. More preferred is benzofuranyl. The 9- to 10-membered bicyclic heteroaryl group is optionally substituted with one or more substituents. These optional substitutents include the substituents as described herein, in particular the substituents defined herein as "A". Further, preferred subsitituents are halo, $C_{1-6}$-haloalkyl, $C_{1-6}$-alkyl, $C_{1-6}$-alkoxy, $C_{1-6}$-haloalkoxy, cyano, $C_{1-6}$-cyanoalkyl, —$CH_2OCH_3$, —$S(O)_2$—$C_{1-6}$-alkyl, $C_{1-6}$-hydroxyalkyl, —$C(O)OC_{1-6}$-alkyl, —NHC(O)—$C_{1-6}$-alkyl, —$NHS(O)_2$$C_{1-6}$-alkyl, —$C(O)N(C_{1-6}$-alkyl$)_2$, —$C(O)NH(C_{1-6}$-alkyl), —$S(O)_2N(C_{1-6}$-alkyl$)_2$, or —$S(O)_2NH(C_{1-6}$-alkyl). Particularly preferred are halo, —$CH_2OH$ and $C_{1-6}$-alkyl.

The term "aromatic" in the above sense means the presence of an electron sextet in the ring, according to Hückel's rule.

The term "heterocycloalkyl" means a monovalent saturated ring, consisting of one ring of 3 to 7, preferably from 4 to 6 atoms as ring members, including one, two, three or four heteroatoms chosen from nitrogen, oxygen or sulfur, the rest being carbon atoms, whereby one, two or three heteroatoms are preferred, and one or two heteroatoms are even more preferred. It is understood that the number of heteroatoms depends on the ring size, i.e. 3 and 4-membered heterocycloalkyl preferably contain one heteroatom, 5 to 7-membered heterocycloalkyl preferably contain one, two or three heteroatoms, and even more preferably one or two heteroatoms. Examples of heterocyclic moieties include, but are not limited to, oxiranyl, thiiranyl, aziridinyl, oxetanyl, azetidinyl, tetrahydro-furanyl, tetrahydro-thiophenyl (synonymous with tetrahydro-thienyl), pyrrolidinyl, pyrazolidinyl, imidazolidinyl, oxazidinyl, isoxazidinyl, thiazolidinyl, isothiazolidinyl, piperidinyl, piperazidinyl, morpholinyl, or tetrahydropyranyl, each of which is optionally substituted as described herein. 3 to 7-membered heterocycloalkyl are optionally substituted with one or more substituents as defined herein, in particular as defined herein as "A". Further, preferred subsitituents are =O, hydroxy, halo, $C_{1-6}$-haloalkyl, $C_{1-6}$-alkyl, $C_{1-6}$-alkoxy, $C_{1-6}$-haloalkoxy, cyano, $C_{1-6}$-cyanoalkyl, —$CH_2OCH_3$, —$S(O)_2$—$C_{1-6}$-alkyl, $C_{1-6}$-hydroxyalkyl, —$C(O)OC_{1-6}$-alkyl, —$N(C_{1-6}$-alkyl$)_2$, —$S(O)_2N(C_{1-6}$-alkyl$)_2$, —NHC(O)—$C_{1-6}$-alkyl, —$NHS(O)_2C_{1-6}$-alkyl, —$C(O)N(C_{1-6}$-alkyl$)_2$, —$C(O)NH(C_{1-6}$-alkyl), —$S(O)_2N(C_{1-6}$-alkyl$)_2$, or —$S(O)_2NH(C_{1-6}$-alkyl). Particularly preferred are =O, hydroxy, $C_{1-6}$-alkyl, —$S(O)_2$—$C_{1-6}$-alkyl, $C_{1-6}$-hydroxyalkyl, —$C(O)OC_{1-6}$-alkyl, —$N(C_{1-6}$-alkyl$)_2$, —$S(O)_2N(C_{1-6}$-alkyl$)_2$, or —$C(O)N(C_{1-6}$-alkyl$)_2$.

The term "one or more substituents" indicates that in principle every position in the aryl (in particular phenyl), heteroaryl, heterocycloalkyl and cycloalkyl residue may bear such a substituent. The pentafluorophenyl residue may be mentioned as an example. However, in 5 to 6-membered aromatic rings, one, two, or three substituents are preferred. In 9- to 10-membered bicyclic heteroaryl rings, one, two or three substituents are preferred. In 5 to 6-membered saturated rings, one, two three or four substituents are preferred. In 3 to 4-membered rings, one or two substituents are preferred.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salt" or "pharmaceutically acceptable salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The invention further comprises individual optical isomers of the compounds herein as well as racemic and non-racemic mixtures thereof.

In detail, the present invention relates to compounds of the general formula (I)

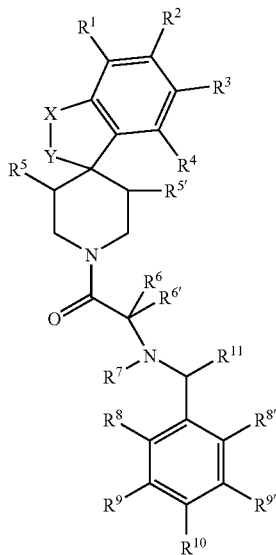

wherein
X and Y are selected from the combinations of
X is $CH_2$, and Y is O,
X is C=O, and Y is O,
X is O, and Y is $CH_2$,
X is $NR^7$, and Y is C=O,
X is $NR^7$, and Y is $CH_2$,
X—Y is —C=C—,
X—Y is —$CH_2CH_2$—, and
X is O, and Y is C=O;

$R^1$, $R^2$, $R^3$, and $R^4$ are each independently hydrogen, halo, $C_{1-6}$-alkyl, $C_{1-6}$-haloalkyl, $C_{1-6}$-alkoxy, or $C_{1-6}$-haloalkoxy;

$R^5$ and $R^{5'}$ are each independently hydrogen or methyl;

$R^6$ and $R^{6'}$ are each independently hydrogen or methyl;

$R^7$ is hydrogen, $C_{1-6}$-alkyl, —C(O)O—$C_{1-6}$-alkyl, or —C(O)O—$C_{2-6}$-alkenyl;

$R^8$, $R^{8'}$, $R^9$, $R^{9'}$, and $R^{10}$ are each independently selected from
hydrogen,
halogen,
$C_{1-4}$-alkyl, optionally substituted by CN or OH,
$C_{1-4}$-haloalkyl,
$C_{1-4}$-alkoxy,
$C_{1-4}$-haloalkoxy, and
hydroxy;

$R^{11}$ is hydrogen,
$C_{1-6}$-alkyl, optionally substituted by CN, OH or halogen,
—$(CR^iR^{ii})_m$—$R^{iii}$,
wherein $R^i$ and $R^{ii}$ are independently from each other
H,
OH,
$C_{1-4}$-alkyl, optionally substituted with OH,
or one $R^i$ and one $R^{ii}$ together with the carbon atom to which they are bound form a 3 to 5-membered cycloalkyl,
wherein m is from 0 to 4,
wherein $R^{iii}$ is
phenyl, naphthyl, 5- to 6-membered monocyclic or 9- to 10-membered bicyclic heteroaryl, 3- to 7-membered heterocycloalkyl, or 3- to 7-membered cycloalkyl,
each of which is optionally substituted by one or more A,
—C(O)—$R^{iv}$,
wherein $R^{iv}$ is
$C_{1-6}$-alkyl, optionally substituted with OH, or CN,
$C_{1-6}$-alkoxy,
hydroxy,
phenyl, naphthyl, benzyl, -Obenzyl, 5- to 6-membered monocyclic or 9- to 10-membered bicyclic heteroaryl, 3- to 7-membered heterocycloalkyl, or 3- to 7-membered cycloalkyl,
each of which is optionally substituted by one or more A,
—C(O)—$NR^fR^g$, or
—$NR^hR^j$,
wherein $R^f$, $R^g$, $R^h$ and $R^j$ are each independently selected from
hydrogen,
$C_{1-6}$-alkyl, and
phenyl or 5- to 6-membered heteroaryl, optionally substituted with one or more A, A is halo, nitro, hydroxy, cyano, =O, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —$(CH_2)_x$—$S(O)_{0-2}C_{1-6}$-alkyl, —$(C_{1-6}$-alkylene)-O—$C_{1-6}$-alkyl, —$(C_{1-6}$-alkylene)-O—$C_{1-6}$-haloalkyl, —$(CH_2)_x$—$NR^aR^b$, —$(CH_2)_x$—$C(O)NR^aR^b$, —$(CH_2)_x$—$S(O)_2NR^aR^b$, —$(CH_2)_x$—$R^c$, —$(CH_2)_x$—O—$R^d$, —$(CH_2)_x$—$S(O)_{0-2}$—$R^d$, —$(CH_2)_x$—$NR^aR^d$, —$(CH_2)_x$—C(O)—$NR^aR^d$, —$(CH_2)_x$—$C(O)R^e$, —$(CH_2)_x$—$NR^aS(O)_2R^e$, or —$(CH_2)_x$—$NR^a(CH_2)_xC(O)R^e$, wherein
x is from 0 to 4;
$R^a$ and $R^b$ are each independently hydrogen or $C_{1-6}$-alkyl,
$R^c$ is phenyl, 5- to 6-membered heteroaryl, 3- to 7-membered heterocycloalkyl, or 3- to 7-membered cycloalkyl,
$R^d$ is phenyl or 5- to 6-membered heteroaryl,
$R^e$ is $C_{1-6}$-alkyl, $C_{1-6}$-alkoxy, phenyl, or 5- to 6-membered heteroaryl, 3- to 7-membered heterocycloalkyl, or 3- to 7-membered cycloalkyl,
wherein phenyl, 5- to 6-membered heteroaryl, 3- to 7-membered heterocycloalkyl, or 3- to 7-membered cycloalkyl of $R^c$, $R^d$ or $R^e$ are optionally substituted with one, two, or three halo, $C_{1-6}$-haloalkyl, $C_{1-6}$-alkyl, or $C_{1-6}$-alkoxy, or one of $R^8$ or $R^{8'}$ together with $R^{11}$ and the atoms to which they are bound form a 5-membered carbocycle, optionally anellated with benzo,
wherein the benzo is optionally substituted with one, two or three substituents selected from halo, $C_{1-6}$-haloalkyl, $C_{1-6}$-alkyl, $C_{1-6}$-alkoxy, $C_{1-6}$-haloalkoxy, nitro, hydroxy, and cyano, or a pharmaceutically acceptable salt thereof.

In the following, certain embodiments of the invention are disclosed, whereby the combination of each of these embodiments with each other embodiment is also encompassed by present invention.

In certain embodiments, $R^1$, $R^2$, $R^3$, and $R^4$ are each independently hydrogen, halo, $C_{1-6}$-alkyl, $C_{1-6}$-haloalkyl, $C_{1-6}$-alkoxy, or $C_{1-6}$-haloalkoxy.

In certain embodiments, $R^1$, $R^2$, $R^3$, and $R^4$ are each independently hydrogen, halo, methyl, ethyl, trifluoromethyl, methoxy, ethoxy, or trifluoromethoxy.

In certain embodiments, $R^1$, $R^2$, $R^3$, and $R^4$ are each hydrogen.

In certain embodiments, $R^1$, $R^2$, $R^3$, and $R^4$ are independently hydrogen or halo.

In certain embodiments, $R^2$ is fluoro, and $R^1$, $R^3$ and $R^4$ are hydrogen.

In certain embodiments, $R^1$, $R^2$ and $R^4$ are hydrogen and $R^3$ is chloro or bromo.

In certain embodiments, $R^1$, $R^2$, $R^3$, and $R^4$ are independently hydrogen or methyl.

In certain embodiments, $R^5$ and $R^{5'}$ are each independently hydrogen or methyl; preferably, $R^5$ and $R^{5'}$ are each hydrogen.

In certain embodiments, $R^6$ and $R^{6'}$ are each independently hydrogen or methyl; preferably, $R^6$ and $R^{6'}$ are each hydrogen.

In certain embodiments, $R^7$ is hydrogen, $C_{1-6}$-alkyl, —C(O)O—$C_{1-6}$-alkyl, or —C(O)O—$C_{2-6}$-alkenyl. In certain embodiments, $R^7$ is hydrogen, $C_{1-6}$-alkyl, or —C(O)O—$C_{2-6}$-alkenyl. Preferably, $R^7$ is hydrogen or $C_{1-6}$-alkyl, and more preferably, $R^7$ is hydrogen.

In certain embodiments, $R^8$, $R^{8'}$, $R^9$, $R^{9'}$, and $R^{10}$ are each independently selected from hydrogen, halogen, $C_{1-4}$-alkyl, $C_{1-4}$-hydroxyalkyl, $C_{1-4}$-cyanoalkyl, $C_{1-4}$-haloalkyl, $C_{1-4}$-alkoxy, $C_{1-4}$-haloalkoxy, and hydroxy.

In certain embodiments, $R^8$, $R^{8'}$, $R^9$, $R^{9'}$, and $R^{10}$ are each independently selected from hydrogen, halogen, $C_{1-4}$-alkyl, $C_{1-4}$-haloalkyl, $C_{1-4}$-alkoxy, $C_{1-4}$-haloalkoxy, and hydroxy.

In certain embodiments, $R^9$, $R^{9'}$, and $R^{10}$ are each independently selected from hydrogen, halogen, $C_{1-4}$-alkyl, $C_{1-4}$-hydroxyalkyl, $C_{1-4}$-cyanoalkyl, $C_{1-4}$-haloalkyl, $C_{1-4}$-alkoxy, $C_{1-4}$-haloalkoxy, and hydroxy, and $R^8$ and $R^{8'}$ are hydrogen.

In certain embodiments, $R^8$, $R^{8'}$, $R^9$, $R^{9'}$, and $R^{10}$ are each independently selected from hydrogen, halogen, methyl, ethyl, trifluoromethyl, methoxy and hydroxy.

In certain embodiments, $R^8$, $R^{8'}$, $R^9$, $R^{9'}$, and $R^{10}$ are each independently selected from hydrogen, halogen, methyl, ethyl, and trifluoromethyl.

In certain embodiments, $R^9$, $R^{9'}$, and $R^{10}$ are each independently selected from hydrogen, halogen, methyl, ethyl and trifluoromethyl, and $R^8$ and $R^{8'}$ are hydrogen.

In certain embodiments, $R^{11}$ is as described above.

In certain embodiments, $R^{11}$ is $C_{1-6}$-alkyl, optionally substituted by CN, OH or halogen, —$(CR^iR^{ii})_m$—$R^{iii}$, wherein $R^i$ and $R^{ii}$ are independently from each other
H,
OH,
$C_{1-4}$-alkyl, optionally substituted with OH,
wherein m is from 0 to 4,
wherein $R^{iii}$ is
phenyl, 5- to 6-membered monocyclic or 9- to 10-membered bicyclic heteroaryl, or 3- to 7-membered heterocycloalkyl,
each of which is optionally substituted by one or more A, —C(O)—$R^{iv}$, wherein $R^{iv}$ is
$C_{1-6}$-alkyl, optionally substituted with OH, or CN,
$C_{1-6}$-alkoxy,
hydroxy,
phenyl, -Obenzyl, 5- to 6-membered monocyclic heteroaryl, or 3- to 7-membered heterocycloalkyl,
each of which is optionally substituted by one or more A, —C(O)—$NR^fR^g$, wherein $R^f$, and $R^g$ are each independently selected from
hydrogen,
$C_{1-6}$-alkyl, and
phenyl or 5- to 6-membered heteroaryl,
optionally substituted with one or more A, A is halo, nitro, hydroxy, cyano, =O, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —$(CH_2)_x$—$S(O)_{0-2}C_{1-6}$-alkyl, —($C_{1-6}$-alkylene)-O—$C_{1-6}$-alkyl, —($C_{1-6}$-alkylene)-O—$C_{1-6}$-haloalkyl, —$(CH_2)_x$—$NR^aR^b$, —$(CH_2)_x$—$C(O)NR^aR^b$, —$(CH_2)_x$—$S(O)_2NR^aR^b$, —$(CH_2)_x$—$R^c$, —$(CH_2)_x$—O—$R^d$, —$(CH_2)_x$—$S(O)_{0-2}$—$R^d$, —$(CH_2)_x$—$NR^aR^d$, —$(CH_2)_x$—$C(O)$—$NR^aR^d$, —$(CH_2)_x$—$C(O)R^e$, —$(CH_2)_x$—$NR^aS(O)_2R^e$, or —$(CH_2)_x$—$NR^a(CH_2)_xC(O)R^e$, wherein x is from 0 to 4;

$R^a$ and $R^b$ are each independently hydrogen or $C_{1-6}$-alkyl, $R^c$ is phenyl, 5- to 6-membered heteroaryl, 3- to 7-membered heterocycloalkyl, or 3- to 7-membered cycloalkyl, $R^d$ is phenyl or 5- to 6-membered heteroaryl, $R^e$ is $C_{1-6}$-alkyl, $C_{1-6}$-alkoxy, phenyl, or 5- to 6-membered heteroaryl, 3- to 7-membered heterocycloalkyl, or 3- to 7-membered cycloalkyl, wherein phenyl, 5- to 6-membered heteroaryl, 3- to 7-membered heterocycloalkyl, or 3- to 7-membered cycloalkyl of $R^c$, $R^d$ or $R^e$ are optionally substituted with one, two, or three halo, $C_{1-6}$-haloalkyl, $C_{1-6}$-alkyl, or $C_{1-6}$-alkoxy.

"A" may be further defined as indicated below.

In —$(CR^iR^{ii})_m$—$R^{iii}$, $R^i$ and $R^{ii}$ are independently from each other H, OH, $C_{1-4}$-alkyl, or $C_{1-4}$-hydroxyalkyl; or one $R^i$ and one $R^{ii}$ together with the carbon atom to which they are bound form a 3 to 5-membered cycloalkyl.

Examples for the linkers —$(CR^iR^{ii})_m$— are: —$CH_2$—, —C(OH)H—, —C(OH)$CH_3$—, —C($CH_2OH$)$CH_3$—, —CH($CH_3$)—, —C($CH_3$)$_2$—, —$CH_2CH_2$—, —$CH_2CH_2CH_2$—, —CH($CH_3$)$CH_2$—, —$CH_2$CH($CH_3$)—, —CH($CH_3$)$CH_2CH_2$—, —$CH_2$CH($CH_3$)$CH_2$—, or —$CH_2CH_2$CH($CH_3$)—. Preferred linkers are —$CH_2$—, —C(OH)H—, —C(OH)$CH_3$—, —C($CH_2OH$)$CH_3$—, —CH($CH_3$)—, or —C($CH_3$)$_2$—.

The variable m in —$(CR^iR^{ii})_m$—$R^{iii}$ is 0, 1, 2, 3 or 4. Preferably, m is 0, 1 or 2. More preferably, m is 0 or 1.

In case $R^{iii}$ is phenyl, naphthyl, 5- to 6-membered monocyclic or 9- to 10-membered bicyclic heteroaryl, or 3- to 7-membered cycloalkyl, m is selected from 0, 1, 2, 3 and 4. Preferably, m is 0, 1, or 2; more preferred is 0 or 1.

In case $R^{iii}$ is 3- to 7-membered heterocycloalkyl and m is 0, the attachment point of the 3- to 7-membered heterocycloalkyl is preferably a carbon atom. Preferably, the 3- to 7-membered heterocycloalkyl of $R^{iii}$ is attached via a carbon atom, regardless of the nature of m. Preferably, m is 1.

When $R^{iii}$ is phenyl, then phenyl is optionally substituted with one ore more, preferably one or two, substituents as described herein. These optional substitutents comprise the substituents defined herein as "A". Further, the subsitituents are halo, hydroxy, $C_{1-6}$-haloalkyl, $C_{1-6}$-alkyl, $C_{1-6}$-alkoxy, $C_{1-6}$-haloalkoxy, cyano, $C_{1-6}$-cyanoalkyl, —$CH_2OCH_3$, —$S(O)_2$—$C_{1-6}$-alkyl, $C_{1-6}$-hydroxyalkyl, —$C(O)OC_{1-6}$-alkyl, —$N(C_{1-6}$-alkyl)$_2$, —$NH(C_{1-6}$-alkyl), $NH_2$, —NHC(O)—$C_{1-6}$-alkyl, —$NH(CH_2C(O)OC_{1-6}$-alkyl), —$NHS(O)_2$$C_{1-6}$-alkyl, —$NHS(O)_2$-phenyl, —$NHS(O)_2$-(p-toluyl), imidazolyl, thiazolyl, oxazolyl, 4-methylpiperazinyl-1-methylenyl, 4-methylpiperazin-1-yl, piperazin-1-yl, morpholin-4-yl, —$C(O)N(C_{1-6}$-alkyl)$_2$, —$C(O)NH(C_{1-6}$-alkyl), —$S(O)_2N(C_{1-6}$-alkyl)$_2$, or —$S(O)_2NH(C_{1-6}$-alkyl) are preferred.

Particularly preferred are halo, hydroxy, $C_{1-6}$-haloalkyl, $C_{1-6}$-alkyl, $C_{1-6}$-alkoxy, $C_{1-6}$-haloalkoxy, —N($C_{1-6}$-alkyl)$_2$, —NH($C_{1-6}$-alkyl), NH$_2$, —NH(CH$_2$C(O)OC$_2$H$_5$), —NHS(O)$_2$-(p-toluyl), 2-imidazolyl, 4-methylpiperazinyl-1-methylenyl or morpholin-4-yl.

When $R^{iii}$ in —(CR$^i$R$^{ii}$)$_m$—R$^{iii}$ is 5 to 6-membered heteroaryl, then 5- to 6-membered heteroaryl is as defined above, namely pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. Preferred 5 to 6-membered heteroaryl groups are pyrazolyl, imidazolyl, thiophenyl (synonymous to thienyl), oxazolyl, thiazolyl, pyridinyl, or pyrimidinyl, in particular 1,3-oxazol-2-yl, 2-thienyl, pyridin-2-yl, pyridin-3-yl, pyridin-4-yl, pyrazol-4-yl, 1,3-thiazol-2-yl, pyrimidin-2-yl or imidazol-2-yl. All these residues are optionally substituted as described herein. These optional substituents comprise the substituents defined herein as "A". Further, the subsitituents are halo, $C_{1-6}$-haloalkyl, $C_{1-6}$-alkyl, $C_{1-6}$-alkoxy, $C_{1-6}$-haloalkoxy, cyano, $C_{1-6}$-cyanoalkyl, —CH$_2$OCH$_3$, —S(O)$_2$—$C_{1-6}$-alkyl, $C_{1-6}$-hydroxyalkyl, —C(O)OC$_{1-6}$-alkyl, —NHC(O)—$C_{1-6}$-alkyl, —NHS(O)$_2$C$_{1-6}$-alkyl, —C(O)N(C$_{1-6}$-alkyl)$_2$, —C(O)NH(C$_{1-6}$-alkyl), —S(O)$_2$N(C$_{1-6}$-alkyl)$_2$, or —S(O)$_2$NH(C$_{1-6}$-alkyl) are preferred. Particularly preferred are halo, —CH$_2$OH and C$_{1-6}$-alkyl.

When $R^{iii}$ in —(CR$^i$R$^{ii}$)$_m$—R$^{iii}$ is 9- to 10-membered bicyclic heteroaryl, then 9- to 10-membered bicyclic heteroaryl is as defined above, namely indolyl, benzoimidazolyl, indazolyl, benzooxazolyl, 1H-pyrrolo[2,3-c]pyridinyl, benzothienyl, benzofuranyl, purinyl, quinolinyl, isoquinolinyl, quinazolinyl, quinoxalinyl, cinnolinyl, phthalazinyl, or pteridinyl. Preferred 9- to 10-membered bicyclic heteroaryl groups are benzofuranyl, benzothienyl, indolyl, benzoimidazolyl, indazolyl, or benzooxazolyl. More preferred is benzofuranyl, in particular 1-benzofuran-2-yl. All these residues are optionally substituted as described herein. These optional substitutents comprise the substituents defined herein as "A". Further, the subsitituents are halo, $C_{1-6}$-haloalkyl, $C_{1-6}$-alkyl, $C_{1-6}$-alkoxy, $C_{1-6}$-haloalkoxy, cyano, $C_{1-6}$-cyanoalkyl, —CH$_2$OCH$_3$, —S(O)$_2$—$C_{1-6}$-alkyl, $C_{1-6}$-hydroxyalkyl, —C(O)OC$_{1-6}$-alkyl, —NHC(O)—$C_{1-6}$-alkyl, —NHS(O)$_2$C$_{1-6}$-alkyl, —C(O)N(C$_{1-6}$-alkyl)$_2$, —C(O)NH(C$_{1-6}$-alkyl), —S(O)$_2$N(C$_{1-6}$-alkyl)$_2$, or —S(O)$_2$NH(C$_{1-6}$-alkyl) are preferred.

When $R^{iii}$ in —(CR$^i$R$^{ii}$)$_m$—R$^{iii}$ is a 3- to 7-membered heterocycloalkyl, then 3- to 7-membered heterocycloalkyl is as defined above, namely oxiranyl, thiiranyl, aziridinyl, oxetanyl, azetidinyl, tetrahydro-furanyl, tetrahydro-thiophenyl (synonymous with tetrahydro-thienyl), pyrrolidinyl, pyrazolidinyl, imidazolidinyl, oxazidinyl, isoxazidinyl, thiazolidinyl, isothiazolidinyl, piperidinyl, piperazidinyl, morpholinyl, or tetrahydropyranyl. When $R^{iii}$ is 3- to 7-membered heterocycloalkyl, oxiranyl, oxetanyl, pyrrolidinyl, piperidinyl, piperazidinyl, morpholinyl, or tetrahydropyranyl are preferred. More preferred is pyrrolidin-2-yl. All these residues are optionally substituted as described herein. These optional substitutents comprise the substituents defined herein as "A". Further, the substituents =O, hydroxy, halo, $C_{1-6}$-haloalkyl, $C_{1-6}$-alkyl, $C_{1-6}$-alkoxy, $C_{1-6}$-haloalkoxy, cyano, $C_{1-6}$-cyanoalkyl, —CH$_2$OCH$_3$, —S(O)$_2$—$C_{1-6}$-alkyl, $C_{1-6}$-hydroxyalkyl, —C(O)OC$_{1-6}$-alkyl, —N(C$_{1-6}$-alkyl)$_2$, —S(O)$_2$N(C$_{1-6}$-alkyl)$_2$, —NHC(O)—$C_{1-6}$-alkyl, —NHS(O)$_2$C$_{1-6}$-alkyl, —C(O)N(C$_{1-6}$-alkyl)$_2$, —C(O)NH(C$_{1-6}$-alkyl), —S(O)$_2$N(C$_{1-6}$-alkyl)$_2$, or —S(O)$_2$NH(C$_{1-6}$-alkyl) are preferred.

In certain embodiments, $R^{iv}$ is as described above.
In certain embodiments,
$R^{iv}$ is $C_{1-6}$-alkoxy,
hydroxy,
phenyl, -Obenzyl, 5- to 6-membered monocyclic heteroaryl, or 3- to 7-membered heterocycloalkyl,
each of which is optionally substituted by one or more A as described herein.
In certain embodiments,
$R^{iv}$ is $C_{1-6}$-alkoxy,
hydroxy,
-Obenzyl, or 3- to 7-membered heterocycloalkyl, each of which is optionally substituted by one or more A as described herein.

Preferably, $R^{iv}$ is 3- to 7-membered heterocycloalkyl which is optionally substituted as described herein.

When $R^{iv}$ is $C_{1-6}$-alkoxy, hydroxy, phenyl, -Obenzyl, 5- to 6-membered monocyclic or 9- to 10-membered bicyclic heteroaryl, m is preferably 0, 1 or 2.

When $R^{iv}$ is 3- to 7-membered heterocycloalkyl, m is preferably 0, 1 or 2, more preferably 0.

When $R^{iv}$ is 5 to 6-membered heteroaryl, then 5- to 6-membered heteroaryl is as defined above, namely pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. Phenyl and 5- to 6-membered heteroaryl are optionally substituted as described herein.

When $R^{iv}$ is phenyl, naphthyl, benzyl, -Obenzyl, 5- to 6-membered monocyclic or 9- to 10-membered bicyclic heteroaryl, then preferred optional subsitituents are halo, hydroxy, $C_{1-6}$-haloalkyl, $C_{1-6}$-alkyl, $C_{1-6}$-alkoxy, $C_{1-6}$-haloalkoxy, cyano, $C_{1-6}$-cyanoalkyl, —CH$_2$OCH$_3$, —S(O)$_2$—$C_{1-6}$-alkyl, $C_{1-6}$-hydroxyalkyl, —C(O)OC$_{1-6}$-alkyl, —N(C$_{1-6}$-alkyl)$_2$, —NH(C$_{1-6}$-alkyl), NH$_2$, —NHC(O)—$C_{1-6}$-alkyl, —NH(CH$_2$C(O)OC$_{1-6}$-alkyl), —NHS(O)$_2$C$_{1-6}$-alkyl, —NHS(O)$_2$-phenyl, —NHS(O)$_2$-(p-toluyl), imidazolyl, thiazolyl, oxazolyl, 4-methylpiperazinyl-1-methylenyl, 4-methylpiperazin-1-yl, piperazin-1-yl, morpholin-4-yl, —C(O)N(C$_{1-6}$-alkyl)$_2$, —C(O)NH(C$_{1-6}$-alkyl), —S(O)$_2$N(C$_{1-6}$-alkyl)$_2$, or —S(O)$_2$NH(C$_{1-6}$-alkyl), or those subsitutents as specifically indicated herein.

When $R^{iv}$ is 3- to 7-membered heterocycloalkyl, then 3- to 7-membered heterocycloalkyl is as defined above, namely oxiranyl, thiiranyl, aziridinyl, oxetanyl, azetidinyl, tetrahydro-furanyl, tetrahydro-thiophenyl (synonymous with tetrahydro-thienyl), pyrrolidinyl, pyrazolidinyl, imidazolidinyl, oxazidinyl, isoxazidinyl, thiazolidinyl, isothiazolidinyl, piperidinyl, piperazidinyl, morpholinyl, or tetrahydropyranyl. Preferred 3- to 7-membered heterocycloalkyl groups are those comprising at least one nitrogen atom, which is attached to the carbonyl group of $R^{iii}$. Preferred examples are azetidinyl, piperazinyl, pyrrolidinyl, piperidinyl, morpholinyl or thiomorpholinyl. All these residues are optionally substituted as described herein. These optional substitutents comprise the substituents defined herein as "A". Further, the subsitituents =O, hydroxy, halo, $C_{1-6}$-haloalkyl, $C_{1-6}$-alkyl, $C_{1-6}$-alkoxy, $C_{1-6}$-haloalkoxy, cyano, $C_{1-6}$-cyanoalkyl, —CH$_2$OCH$_3$, —S(O)$_2$—$C_{1-6}$-alkyl, $C_{1-6}$-hydroxyalkyl, —C(O)OC$_{1-6}$-alkyl, —N(C$_{1-6}$-alkyl)$_2$, —S(O)$_2$N(C$_{1-6}$-alkyl)$_2$, —NHC(O)—$C_{1-6}$-alkyl, —NHS(O)$_2$C$_{1-6}$-alkyl, —C(O)N(C$_{1-6}$-alkyl)$_2$, —C(O)NH(C$_{1-6}$-alkyl), —S(O)$_2$N(C$_{1-6}$-alkyl)$_2$, or —S(O)$_2$NH(C$_{1-6}$-alkyl) are preferred. Particularly preferred are =O, hydroxy, $C_{1-6}$-alkyl, —S(O)$_2$—$C_{1-6}$-alkyl, $C_{1-6}$-hydroxyalkyl, —N(C$_{1-6}$-alkyl)$_2$, —S(O)$_2$N(C$_{1-6}$-alkyl)$_2$, or —C(O)N(C$_{1-6}$-alkyl)$_2$, or those subsitutents as specifically indicated in the examples.

When $R^{iii}$ is —C(O)—$NR^fR^g$, then m is preferably 0, 1 or 2, more preferably 0 or 1.

When $R^{iii}$ is —$NR^fR^g$, then m is preferably 1, 2 or 3, more preferably 1 or 2.

When $R^f$, $R^g$, $R^h$ and/or $R^j$ are 5- to 6-membered heteroaryl, then 5- to 6-membered heteroaryl is as defined above, namely pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. Preferred 5- to 6-membered heteroaryl groups are isoxazolyl, pyridinyl, pyrimidinyl, or pyrazinyl; in particular pyridine-2-yl, pyrazin-2-yl, isoxazol-3-yl or pyrimidin-2-yl. All these residues are optionally substituted as described herein. In particular, these optional subtituents comprise the subtituents defined with "A".

"A" defines the optional substituents of cyclic groups of $R^{iii}$, namely phenyl, naphthyl, 5- to 6-membered monocyclic or 9- to 10-membered bicyclic heteroaryl, 3- to 7-membered heterocycloalkyl, or 3- to 7-membered cycloalkyl; of cyclic groups of $R^{iv}$, namely phenyl, naphthyl, benzyl, -Obenzyl, 5- to 6-membered monocyclic or 9- to 10-membered bicyclic heteroaryl, 3- to 7-membered heterocycloalkyl, or 3- to 7-membered cycloalkyl; and of $R^f$, $R^g$, $R^h$ and $R^j$, namely phenyl or 5- to 6-membered heteroaryl.

"A" is defined as halo, nitro, hydroxy, cyano, $=O$, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —$(CH_2)_x$—$S(O)_{0-2}C_{1-6}$-alkyl, —($C_{1-6}$-alkylene)-O—$C_{1-6}$-alkyl, —($C_{1-6}$-alkylene)-O—$C_{1-6}$-haloalkyl, —$(CH_2)_x$—$NR^aR^b$, —$(CH_2)_x$—C(O)$NR^aR^b$, —$(CH_2)_x$—$S(O)_2NR^aR^b$, —$(CH_2)_x$—$R^c$, —$(CH_2)_x$—O—$R^d$, —$(CH_2)_x$—$S(O)_{0-2}$—$R^d$, —$(CH_2)_x$—$NR^aR^d$, —$(CH_2)_x$—C(O)—$NR^aR^d$, —$(CH_2)_x$—$C(O)R^e$, —$(CH_2)_x$—$NR^aS(O)_2R^e$, or —$(CH_2)_x$—$NR^a(CH_2)_xC(O)R^e$, wherein x is 0, 1, 2, 3 or 4; preferably 0, 1 or 2;

$R^a$ and $R^b$ are each independently hydrogen or $C_{1-6}$-alkyl, $R^c$ is phenyl, 5- to 6-membered heteroaryl, 3- to 7-membered heterocycloalkyl, or 3- to 7-membered cycloalkyl, optionally substituted with one, two, or three halo, $C_{1-6}$-haloalkyl, $C_{1-6}$-alkyl, or $C_{1-6}$-alkoxy, $R^d$ is phenyl or 5- to 6-membered heteroaryl, optionally substituted with one, two, or three halo, $C_{1-6}$-haloalkyl, $C_{1-6}$-alkyl, or $C_{1-6}$-alkoxy, $R^e$ is $C_{1-6}$-alkyl, $C_{1-6}$-alkoxy, or phenyl, or 5- to 6-membered heteroaryl, 3- to 7-membered heterocycloalkyl, or 3- to 7-membered cycloalkyl, optionally substituted with one, two, or three halo, $C_{1-6}$-haloalkyl, $C_{1-6}$-alkyl, or $C_{1-6}$-alkoxy.

"A" is preferably halo, nitro, hydroxy, cyano, $=O$, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —$(CH_2)_x$—$S(O)_{0-2}C_{1-6}$-alkyl, —$(CH_2)_x$—$NR^aR^b$, —$(CH_2)_x$—C(O)$NR^aR^b$, —$(CH_2)_x$—$S(O)_2NR^aR^b$, —$(CH_2)_x$—$R^c$, —$(CH_2)_x$—$S(O)_{0-2}$—$R^d$, —$(CH_2)_x$—$C(O)R^e$, or —$(CH_2)_x$—$NR^a(CH_2)_xC(O)R^e$, wherein x is 0, 1, 2, 3 or 4; preferably x is 0 or 1, $R^a$ and $R^b$ are each independently hydrogen or $C_{1-6}$-alkyl, $R^c$ is phenyl, 5- to 6-membered heteroaryl, 3- to 7-membered heterocycloalkyl, or 3- to 7-membered cycloalkyl, optionally substituted with one, two, or three halo, $C_{1-6}$-haloalkyl, $C_{1-6}$-alkyl, or $C_{1-6}$-alkoxy, $R^d$ is phenyl or 5- to 6-membered heteroaryl, optionally substituted with one, two, or three halo, $C_{1-6}$-haloalkyl, $C_{1-6}$-alkyl, or $C_{1-6}$-alkoxy, $R^e$ is $C_{1-6}$-alkyl, $C_{1-6}$-alkoxy, phenyl, or 5- to 6-membered heteroaryl, 3- to 7-membered heterocycloalkyl, or 3- to 7-membered cycloalkyl, optionally substituted with one, two, or three halo, $C_{1-6}$-haloalkyl, $C_{1-6}$-alkyl, or $C_{1-6}$-alkoxy.

Preferred A for aromatic rings are halo, nitro, hydroxy, cyano, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —$(CH_2)_x$—$S(O)_{0-2}C_{1-6}$-alkyl, —$(CH_2)_x$—$NR^aR^b$, —$(CH_2)_x$—C(O)$NR^aR^b$, —$(CH_2)_x$—$S(O)_2NR^aR^b$, —$(CH_2)_x$—$R^c$, —$(CH_2)_x$—$S(O)_{0-2}$—$R^d$, —$(CH_2)_x$—$C(O)R^e$, or —$(CH_2)_x$—$NR^a(CH_2)_xC(O)R^e$, wherein x is 0, 1, 2, 3 or 4; preferably x is 0 or 1, $R^a$ and $R^b$ are each independently hydrogen or $C_{1-6}$-alkyl, $R^c$ is phenyl, 5- to 6-membered heteroaryl, 3- to 7-membered heterocycloalkyl, or 3- to 7-membered cycloalkyl, $R^d$ is phenyl or 5- to 6-membered heteroaryl, $R^e$ is $C_{1-6}$-alkyl, $C_{1-6}$-alkoxy, phenyl, or 5- to 6-membered heteroaryl, 3- to 7-membered heterocycloalkyl, or 3- to 7-membered cycloalkyl, wherein phenyl, 5- to 6-membered heteroaryl, 3- to 7-membered heterocycloalkyl, or 3- to 7-membered cycloalkyl of $R^c$, $R^d$ or $R^e$ are optionally substituted with one, two, or three halo, $C_{1-6}$-haloalkyl, $C_{1-6}$-alkyl, or $C_{1-6}$-alkoxy.

Preferred A for saturated rings are those described for aromatic rings, and additionally $=O$.

In certain embodiments of the invention, one of $R^8$ or $R^{8'}$ together with $R^{11}$ and the atoms to which they are bound form a 5-membered carbocycle, optionally anellated with benzo, wherein the benzo is optionally substituted with one, two or three substituents selected from halo, $C_{1-6}$-haloalkyl, $C_{1-6}$-alkyl, $C_{1-6}$-alkoxy, $C_{1-6}$-haloalkoxy, nitro, hydroxy, and cyano. Preferably, one of $R^8$ or $R^{8'}$ together with $R^{11}$ form fluorene, optionally substituted with one, two or three substituents selected from halo, $C_{1-6}$-haloalkyl, $C_{1-6}$-alkyl, $C_{1-6}$-alkoxy, $C_{1-6}$-haloalkoxy, nitro, hydroxy, and cyano.

Preferably, $R^{11}$ is $C_{1-6}$-alkyl, $C_{1-6}$-hydroxyalkyl, $C_{1-6}$-cyanoalkyl, or —$(CR^iR^{ii})_m$—$R^{iii}$, wherein $R^i$, $R^{ii}$ and $R^{iii}$ are as defined above.

In a certain embodiment the compounds of the invention are those compounds of formula (I-a), wherein X is $CH_2$, and Y is O, and $R^1$ to $R^{11}$ are as defined above.

In a certain embodiment the compounds of the invention are those compounds of formula (I-b), wherein X is C=O, and Y is O, and $R^1$ to $R^{11}$ are as defined above.

In a certain embodiment the compounds of the invention are those compounds of formula (I-c), X is O, and Y is $CH_2$, and $R^1$ to $R^{11}$ are as defined above.

In a certain embodiment the compounds of the invention are those compounds of formula (I-d), X is $NR^7$, and Y is C=O, and $R^1$ to $R^{11}$ are as defined above.

In a certain embodiment the compounds of the invention are those compounds of formula (I-e), X is $NR^7$, and Y is $CH_2$, and $R^1$ to $R^{11}$ are as defined above.

In a certain embodiment the compounds of the invention are those compounds of formula (I-f), X—Y is —C=C—, and $R^1$ to $R^{11}$ are as defined above.

In a certain embodiment the compounds of the invention are those compounds of formula (I-g), X—Y is —$CH_2CH_2$—, and $R^1$ to $R^{11}$ are as defined above.

In a certain embodiment the compounds of the invention are those compounds of formula (I-h), X is O, and Y is C=O, and $R^1$ to $R^{11}$ are as defined above.

Preferred embodiments of the present invention are those of compounds I-a, I-b. I-c. I-e. I-f or I-g, particularly preferred are those of I-a or I-b.

The invention further encompasses an embodiment of formula (I)

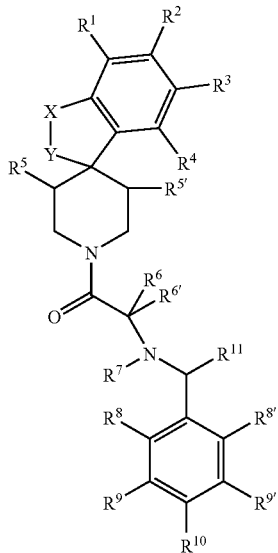

wherein
X and Y are selected from the combinations of:
X is $CH_2$, and Y is O,
X is C=O, and Y is O,
X is O, and Y is $CH_2$,
X is $NR^7$, and Y is C=O,
X is $NR^7$, and Y is $CH_2$,
X—Y is —C=C—,
X—Y is —$CH_2CH_2$—, and
X is O, and Y is C=O;
$R^1$, $R^2$, $R^3$, and $R^4$ are each independently hydrogen, halo, methyl, ethyl, trifluoromethyl, methoxy, ethoxy, or trifluoromethoxy;
$R^5$ and $R^{5'}$ are each hydrogen;
$R^6$ and $R^{6'}$ are each independently hydrogen or methyl;
$R^7$ is hydrogen, $C_{1-6}$-alkyl, or —C(O)O—$C_{2-6}$-alkenyl;
$R^8$, $R^{8'}$, $R^9$, $R^{9'}$, and $R^{10}$ are each independently selected from
hydrogen,
halogen,
$C_{1-4}$-alkyl, optionally substituted by CN or OH,
$C_{1-4}$-haloalkyl,
$C_{1-4}$-alkoxy,
$C_{1-4}$-haloalkoxy, and
hydroxy;
$R^{11}$ is $C_{1-6}$-alkyl, optionally substituted by CN, OH or halogen,
—$(CR^iR^{ii})_m$—$R^{iii}$,
wherein $R^i$ and $R^{ii}$ are independently from each other
H,
OH,
$C^{1-4}$-alkyl, optionally substituted with OH,
wherein m is from 0 to 4,
wherein $R^{iii}$ is
phenyl, 5- to 6-membered monocyclic or 9- to 10-membered bicyclic heteroaryl, or 3- to 7-membered heterocloalkyl,
each of which is optionally substituted by one or more A,
—C(O)—$R^{iv}$,
wherein $R^{iv}$ is
$C_{1-6}$-alkyl, optionally substituted with OH, or CN,
$C_{1-6}$-alkoxy,
hydroxy,
phenyl, -Obenzyl, 5- to 6-membered monocyclic heteroaryl, or 3- to 7-membered heterocycloalkyl,
each of which is optionally substituted by one or more A,
—C(O)—$NR^fR^g$,
wherein $R^f$, and $R^g$ are each independently selected from hydrogen,
$C_{1-6}$-alkyl, and
phenyl or 5- to 6-membered heteroaryl,
optionally substituted with one or more A,
A is halo, nitro, hydroxy, cyano, =O, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —$(CH_2)_x$—$S(O)_{0-2}C_{1-6}$-alkyl, —($C_{1-6}$-alkylene)-O—$C_{1-6}$-alkyl, —($C_{1-6}$-alkylene)-O—$C_{1-6}$-haloalkyl, —$(CH_2)_x$—$NR^aR^b$, —$(CH_2)_x$—$C(O)NR^aR^b$, —$(CH_2)_x$—$S(O)_2NR^aR^b$, —$(CH_2)_x$—$R^c$, —$(CH_2)_x$—O—$R^d$, —$(CH_2)_x$—$S(O)_{0-2}$—$R^d$, —$(CH_2)_x$—$NR^aR^d$, —$(CH_2)_x$—C(O)—$NR^aR^d$, —$(CH_2)_x$—$C(O)R^e$, —$(CH_2)_x$—$NR^aS(O)_2R^e$, or —$(CH_2)_x$—$NR^a(CH_2)_xC(O)R^e$, wherein
x is from 0 to 4;
$R^a$ and $R^b$ are each independently hydrogen or $C_{1-6}$-alkyl,
$R^c$ is phenyl, 5- to 6-membered heteroaryl, 3- to 7-membered heterocycloalkyl, or 3- to 7-membered cycloalkyl,
$R^d$ is phenyl or 5- to 6-membered heteroaryl,
$R^e$ is $C_{1-6}$-alkyl, $C_{1-6}$-alkoxy, phenyl, or 5- to 6-membered heteroaryl, 3- to 7-membered heterocycloalkyl, or 3- to 7-membered cycloalkyl,
wherein phenyl, 5- to 6-membered heteroaryl, 3- to 7-membered heterocycloalkyl, or 3- to 7-membered cycloalkyl of $R^c$, $R^d$ or $R^e$ are optionally substituted with one, two, or three halo, $C_{1-6}$-haloalkyl, $C_{1-6}$-alkyl, or $C_{1-6}$-alkoxy, or one of $R^8$ or $R^{8'}$ together with $R^{11}$ and the atoms to which they are bound form a 5-membered carbocycle, optionally anellated with benzo,
wherein the benzo is optionally substituted with one, two or three substituents selected from halo, $C_{1-6}$-haloalkyl, $C_{1-6}$-alkyl, $C_{1-6}$-alkoxy, $C_{1-6}$-haloalkoxy, nitro, hydroxy, and cyano, or a pharmaceutically acceptable salt thereof.

Preferred compounds of the invention are those explicitly shown in the examples.

More preferred compounds of the invention are
RS)-N-[(4-Chlorophenyl)(phenyl)methyl]-2-oxo-2-(1'H, 3H-spiro[2-benzofuran-1,4'-piperidin]-1'-yl)ethanamine,
N-[(+)-(4-chlorophenyl)(phenyl)methyl]-2-oxo-2-(1'H,3H-spiro[2-benzofuran-1,4'-piperidin]-1'-yl)ethanamine,
N-(Diphenylmethyl)-2-oxo-2-(1'H,3H-spiro[2-benzofuran-1,4'-piperidin]-1'-yl)ethanamine,
(RS)-N-[(3-Chlorophenyl)(phenyl)methyl]-2-oxo-2-(1'H, 3H-spiro[2-benzofuran-1,4'-piperidin]-1'-yl)ethanamine,
(RS)-N-[(3,4-Dichlorophenyl)(phenyl)methyl]-2-oxo-2-(1'H,3H-spiro[2-benzofuran-1,4'-piperidin]-1'-yl)ethanamine, (RS)-N-[(2,4-Dichlorophenyl)(phenyl)methyl]-2-oxo-2-(1'H,3H-spiro[2-benzofuran-1,4'-piperidin]-1'-yl)ethanamine,
(RS)-2-Oxo-N-{phenyl[3-(trifluoromethyl)phenyl]methyl}-2-(1'H,3H-spiro[2-benzofuran-1,4'-piperidin]-1'-yl)ethanamine,
(RS)-N-{(4-Fluorophenyl)[3-(trifluoromethyl)phenyl]methyl}-2-oxo-2-(1'H,3H-spiro[2-benzofuran-1,4'-piperidin]-1'-yl)ethanamine,
(RS)-2-Oxo-N-[phenyl(pyrimidin-2-yl)methyl]-2-(1'H,3H-spiro[2-benzofuran-1,4'-piperidin]-1'-yl)ethanamine,
(RS)-2-Oxo-N-{phenyl[4-(trifluoromethyl)phenyl]methyl}-2-(1'H,3H-spiro[2-benzofuran-1,4'-piperidin]-1'-yl)ethanamine,
(RS)-N-[(4-Chlorophenyl)(4-fluorophenyl)methyl]-2-oxo-2-(1'H,3H-spiro[2-benzofuran-1,4'-piperidin]-1'-yl)ethanamine,
(RS)-2-Oxo-N-[phenyl(2-thienyl)methyl]-2-(1'H,3H-spiro[2-benzofuran-1,4'-piperidin]-1'-yl)ethanamine,
(RS)-2-Oxo-N-[phenyl(pyridin-2-yl)methyl]-2-(1'H,3H-spiro[2-benzofuran-1,4'-piperidin]-1'-yl)ethanamine,
(RS)-N-{[4-(Difluoromethoxy)phenyl](phenyl)methyl}-2-oxo-2-(1'H,3H-spiro[2-benzofuran-1,4'-piperidin]-1'-yl)ethanamine,
(RS)-N-[(4-Fluorophenyl)(2-thienyl)methyl]-2-oxo-2-(1'H,3H-spiro[2-benzofuran-1,4'-piperidin]-1'-yl)ethanamine,
(RS)-N-[(3,5-Dimethyl-1H-pyrazol-4-yl)(phenyl)methyl]-2-oxo-2-(1'H,3H-spiro[2-benzofuran-1,4'-piperidin]-1'-yl)ethanamine,
(2R)-N-(4-Chlorophenyl)-2-{[2-oxo-2-(1'H,3H-spiro[2-benzofuran-1,4'-piperidin]-1'-yl)ethyl]amino}-2-phenylacetamide,
(RS)-N-[(3-Methylphenyl)(phenyl)methyl]-2-oxo-2-(1'H,3H-spiro[2-benzofuran-1,4'-piperidin]-1'-yl)ethanamine,
(RS)-N-[(4-Methoxyphenyl)(phenyl)methyl]-2-oxo-2-(1'H,3H-spiro[2-benzofuran-1,4'-piperidin]-1'-yl)ethanamine,
(RS)-4-Chloro-2-[{[2-oxo-2-(1'H,3H-spiro[2-benzofuran-1,4'-piperidin]-1'yl)ethyl]amino}(phenyl)methyl]phenol,
(RS)-4-Methyl-N-{2-[{[2-oxo-2-(1'H,3H-spiro[2-benzofuran-1,4'-piperidin]-1'-yl)ethyl]amino}(phenyl)methyl]phenyl}benzenesulfonamide,
(RS)-N-{[2-(1H-Imidazol-2-yl)phenyl](phenyl)methyl}-2-oxo-2-(1'H,3H-spiro[2-benzofuran-1,4'-piperidin]-1'-yl)ethanamine,
(1S,2R)-2-(4-Chlorophenyl)-1-(4-morpholin-4-ylphenyl)-2-{[2-oxo-2-(1'H,3H-spiro[2-benzofuran-1,4'-piperidin]-1'-yl)ethyl]amino}ethanol,
(1RS,2RS)-1-(4-Chlorophenyl)-1-{[2-oxo-2-(1'H,3H-spiro[2-benzofuran-1,4'-piperidin]-1'-yl)ethyl]amino}-2-pyridin-2-yl-propan-2-ol,
1-(4-Chlorophenyl)-1-{[2-oxo-2-(1'H,3H-spiro[2-benzofuran-1,4'-piperdin]-1'-yl)ethyl]amino}-2-pyridin-3-yl-propan-2-ol,
1-(4-Chlorophenyl)-1-{[2-oxo-2-(1'H,3H-spiro[2-benzofuran-1,4'-piperdin]-1'-yl)ethyl]amino}-2-pyridin-4-ylpropan-2-ol,
(RS)-N-[(3-chlorophenyl)(pyridin-2-yl)methyl]-2-oxo-2-(1'H,3H-spiro[2-benzofuran-1,4'-piperidin]-1'-yl)ethanamine,
(RS)-N-[(3-Chlorophenyl)(1,3-thiazol-2-yl)methyl]-2-oxo-2-(1'H,3H-spiro[2benzofuran-1,4'-piperidin]-1'-yl)ethanamine,
(RS)-N-[(3-Chlorophenyl){3-[(4-methylpiperazin-1-yl)methyl]phenyl}methyl]-2-oxo-2-(1'H,3H-spiro[2-benzofuran-1,4'-piperidin]-1'-yl)ethanamine,
(RS)-N-[(3-Chlorophenyl)(1,3-oxazol-2-yl)methyl]-2-oxo-2-(1'H,3H-spiro[2-benzofuran-1,4'-piperidin]-1'-yl)ethanamine,
1-[(2R)-2-{[2-Oxo-2-(1'H,3H-spiro[2-benzofuran-1,4'-piperidin]-1'-yl)ethyl]amino}-2-phenylacetyl]azetidin-3-ol,
(2R)-2-{[2-Oxo-2-(1'H,3H-spiro[2-benzofuran-1,4'-piperidin]-1'-yl)ethyl]amino}-2-phenyl-N-pyridin-2-ylacetamide,
(2R)-2-{[2-Oxo-2-(1'H,3H-spiro[2-benzofuran-1,4'-piperidin]-1'-yl)ethyl]amino}-2-phenyl-N-pyrazin-2-ylacetamide,
N,N-Dimethyl-4-[(2R)-2-{[2-oxo-2-(1'H,3H-spiro[2-benzofuran-1,4'-piperidin]-1'-yl)ethyl]amino}-2-phenylacetyl]piperazine-1-sulfonamide,
(2R)-N-Isoxazol-3-yl-2-{[2-oxo-2-(1'H,3H-spiro[2-benzofuran-1,4'-piperidin]-1'-yl)ethyl]amino}-2-phenylacetamide,
1'-[N-(Diphenylmethyl)glycyl]-3H-spiro[2-benzofuran-1,4'-piperidin]-3-one, or
N-(Diphenylmethyl)-N-methyl-2-oxo-2-(1'H,3H-spiro[2-benzofuran-1,4'-piperidin]-1'-yl)ethanamine.

The invention also encompasses methods for the treatment of dysmenorrhea, hypertension, chronic heart failure, inappropriate secretion of vasopressin, liver cirrhosis, nephrotic syndrome, obsessive compulsive disorder, anxiety and depressive disorders which comprises administering a compound of formula (I), (I-a), (I-b), (I-c), (I-d), (I-e), (I-f), (I-g) or (I-h).

The invention also encompasses a pharmaceutical composition comprising a compound of formula (I), (I-a), (I-b), (I-c), (I-d), (I-e), (I-f), (I-g) or (I-h) and a pharmaceutically acceptable carrier. The pharmaceutical composition can further comprise at least one pharmaceutically acceptable excipient.

In a certain embodiment, the compounds of formula (I) of the invention can be manufactured according to a process comprising the step of reacting a compound of formula (II):

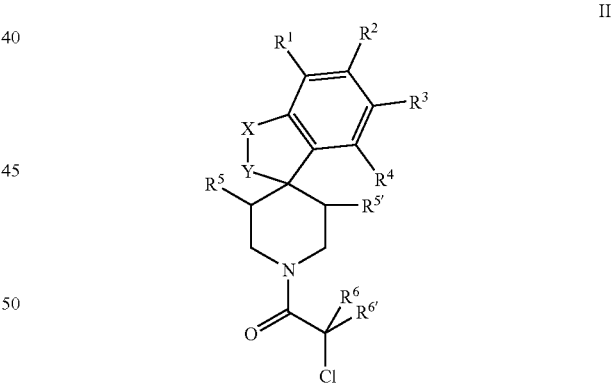

with a compound of formula (III):

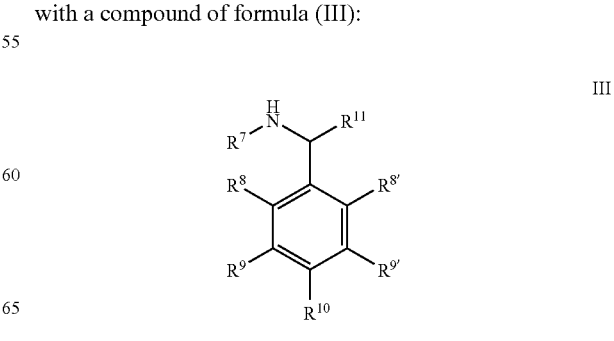

to obtain a compound of formula (I) wherein $R^1$ to $R^{6'}$, $R^8$ to $R^{11}$, X and Y are as defined hereinabove for formula (I) and $R^7$ is hydrogen or $C_{1-6}$-alkyl.

In another embodiment, the compounds of formula (I) of the invention can be manufactured according to a process comprising the step of reacting a compound of formula (V)

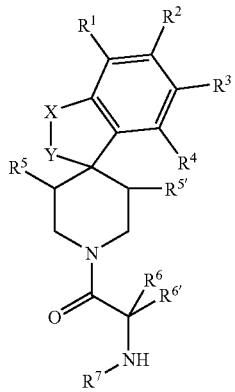

V with a compound of formula (VI)

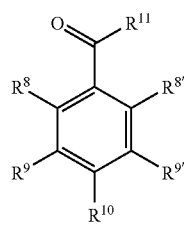

VI or with a compound of formula (VIII)

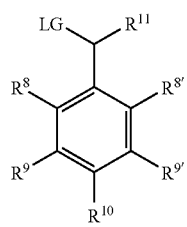

VIII wherein LG is a leaving group, preferably halogen, —$OSO_2Me$, —$OSO_2C_6H_4CH_3$, to obtain a compound of formula (I) wherein $R^1$ to $R^{6'}$, $R^8$ to $R^{11}$, X and Y are as defined hereinabove for formula (I) and $R^7$ is hydrogen or $C_{1-6}$-alkyl.

In another embodiment, the compounds of formula (I) of the invention can be manufactured according to a process comprising the step of reacting a compound of formula (I-4)

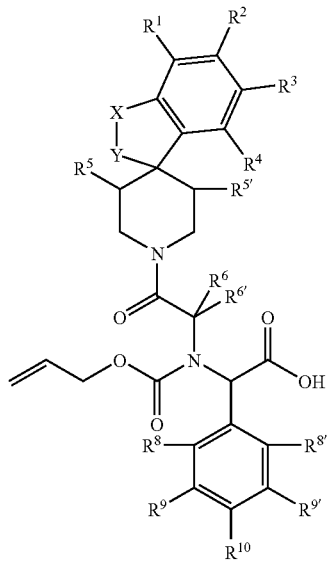

I-4 with an amine $HNR^fR^g$, followed by palladium catalyzed removal of the allyloxycarbonyl group to obtain a compound of formula (I) wherein $R^1$ to $R^{6'}$, $R^8$ to $R^{11}$, $R^f$, $R^g$ X and Y are as defined hereinabove for formula (I) and $R^7$ is hydrogen.

These processes are described in more detail with the following general schemes and procedures:

The compounds of formula I as described herein can be prepared in accordance with the process variants as described above and with the following schemes 1 to 8. The starting materials and intermediates described in the example section are either commercially available or are otherwise known or derivable from the chemical literature. The following abbreviations are used:

HBTU: N,N,N',N'-tetramethyl-o-(benzotriazol-1-yl)uronium hexafluorophosphate
HATU: O-(7-azabenzotriazol-1-yl)-N,N,N',N'-tetramethyluronium hexafluorophosphate
THF: tetrahydrofuran
DCM: dichloromethane
DMF: N,N-dimethylformamide
BOC: t-butyloxycarbonyl
TMS: trimethylsilyl
TEA: triethylamine
DIPEA: N,N-diisopropylethylamine
LDA: lithiumdiisopropylamide
DME: dimethoxyethane
TPP: triphenylphosphine
LG: leaving group, e.g. halogen, $OSO_2Me$, $OSO_2C_6H_4CH_3$
MW: microwave Scheme 1
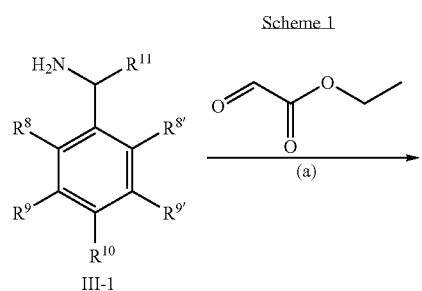
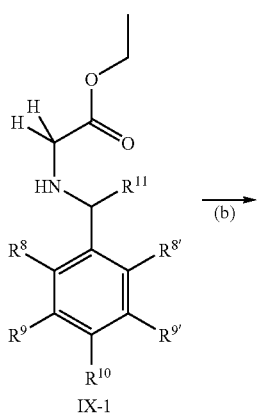
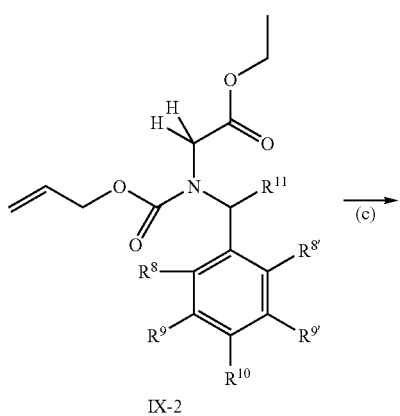
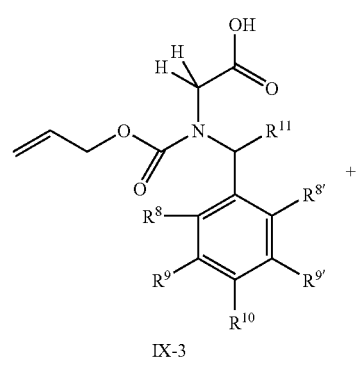
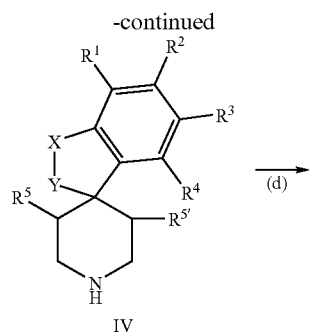
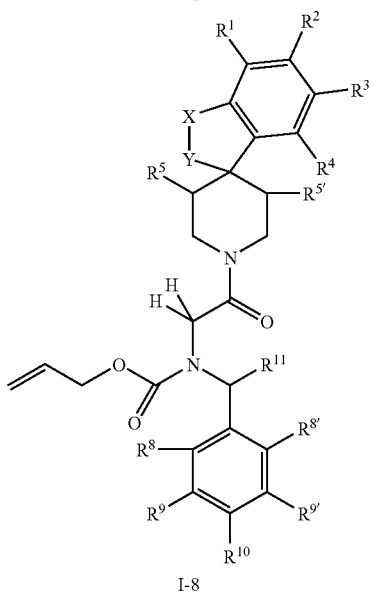
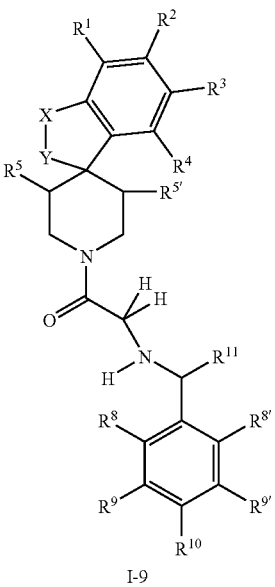
Synthetic Methods (Scheme 1):
(a) Reductive amination according to Maryanoff[1]: NaBH(OAc)$_3$ (3 eq), AcOH (0.1 eq), DCM, 16 h, 20° C.
(b) Standard alkoxy- or allyloxycarbonylation: e.g. ClCO$_2$Allyl (1.1 eq), DIPEA (1.1 eq), DCM, 20° C., 8 h
(c) Standard mild ester hydrolysis: LiOH (5 eq), THF, MeOH, H$_2$O, 20° C., 2 h (d) Standard peptide coupling: HBTU or HATU (1.3 eq), TEA (3.3 eq), DCM, 3 h, 20° C.

(e) Removal of allyloxycarbonyl group by palladium catalyzed transfer of the allyl group to an excess of pyrrolidine. N-allylpyrrolidine and pyrrolidine are then easily separated from the product due to their volatility: Pd(TPP)$_4$, pyrrolidine (5 eq), DCM, 20° C., 3 h

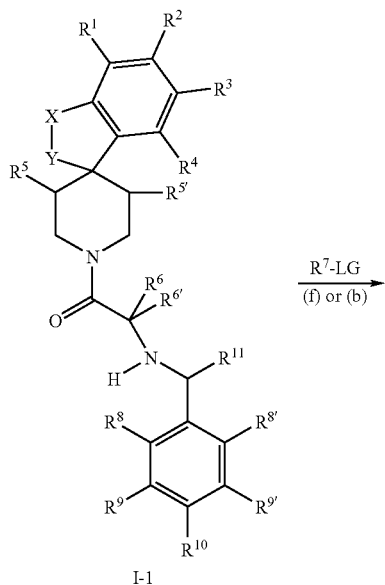

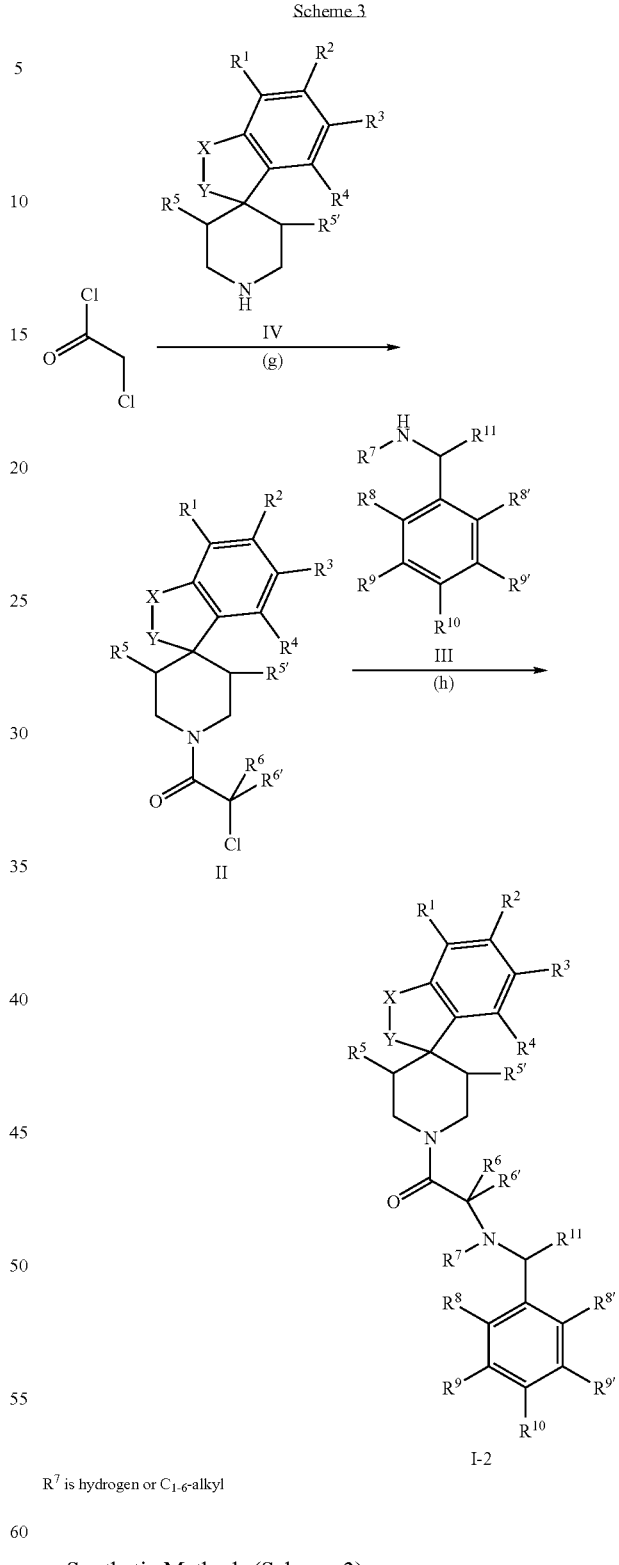

$R^7$ is hydrogen or $C_{1-6}$-alkyl

Synthetic Methods (Scheme 2):

(f) Standard methylation with excess sodium hydride and methyl iodide: NaH (3 eq), $R^7$-LG (3 eq), DMF, 20° C., 24 h Synthetic Methods (Scheme 3):

(g) Chloroacetylation of in the presence of Huenig's base with chloroacetylchloride.[2]: DIPEA, THF, 0-20° C., 0.5 h (h) Alkylation of primary and secondary amines with an α-chloroamide in the presence of an inorganic or organic base such as potassium carbonate, cesium carbonate, triethylamine, N-ethyldiisopropylamine, 1,1,3,3-tetramethylguanidine etc in a suitable solvent such as THF, DCM, MeCN, DMF, etc. at temperatures 20-80° C.: e.g. TEA (3 eq), DMF, 20° C., 48 h Scheme 4

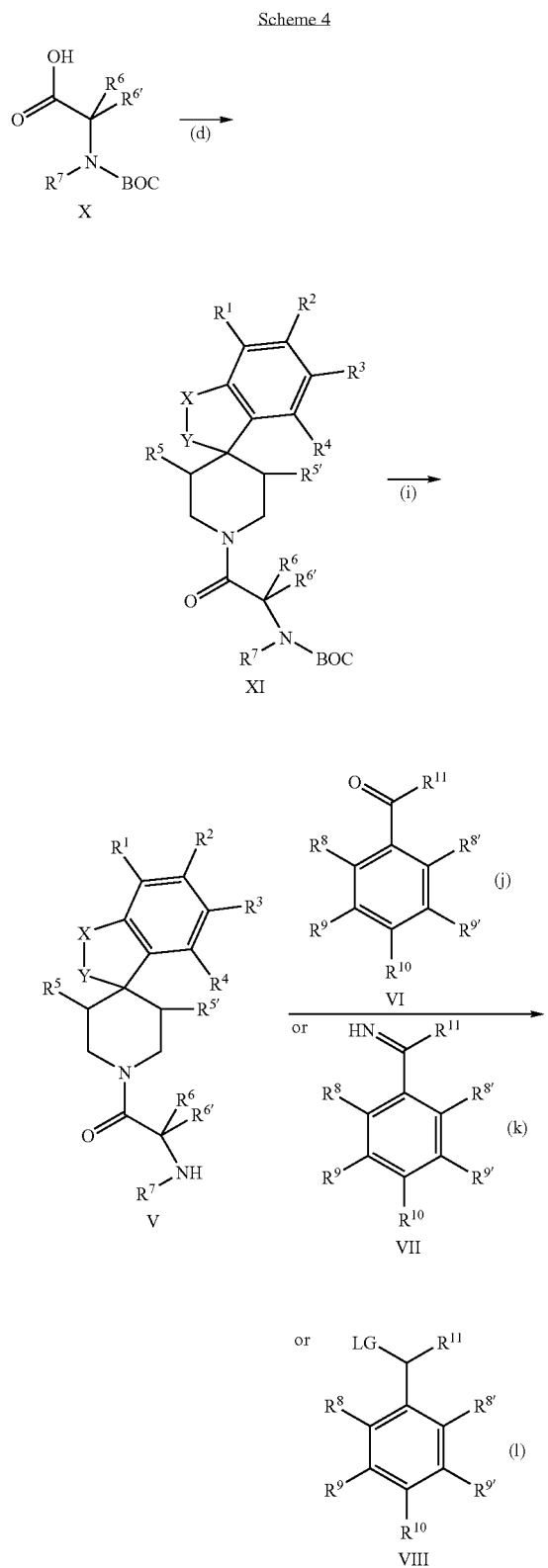

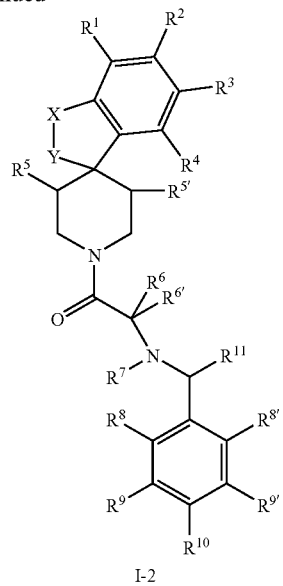

I-2

$R^7$ is hydrogen or $C_{1-6}$-alkyl

Synthetic Methods (Scheme 4):

(i) Standard BOC cleavage. Free amines are obtained after neutralisation with 10% $Na_2CO_3$ or 1 N NaOH and extraction with DCM: 1. TFA (5 eq), DCM, 20° C., 1 h; 2. $Na_2CO_3$ extraction (j) Reductive amination according to Mattson[3] adapted for small scale parallel chemistry using microwave heating up to 140° C. in toluene to effect imine formation between poorly reactive diarylketones and a primary amine: 1. Ti(OiPr)$_4$ (2 eq), toluene, MW 140° C., 10 min; 2. NaBH$_3$CN (1.2 eq), EtOH, 1 h; 3. H$_2$O, 20° C. 15 min (k) Reaction of a ketone either with the salt of a primary amine4 in DCM or MeCN at ambient temperature or with its free base at 20-80° C. followed by in situ reduction of the intermediate imine: 1. MeCN, 80°, 1 h; 2. NaBH$_3$CN, 20° C., 24 h, MeCN (l) Preferred method for the coupling of intermediates of formula (V) to compounds of formula (I) where at least one of the two substituents $R^6$ and $R^{6'}$ is not hydrogen: DIPEA, NMP, MW 200° C., 15 min or $Cs_2CO_3$, MeCN, 80° C., 16 h Scheme 5

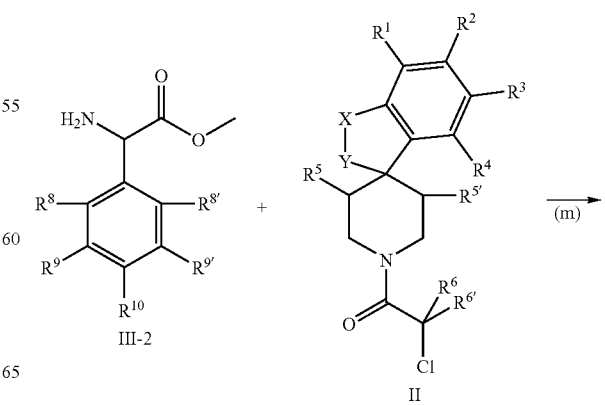

Synthetic Methods (Scheme 5):
(m) Variation of method (h) with higher reaction temperature: TEA (4 eq), DMF, 80° C., 16 h
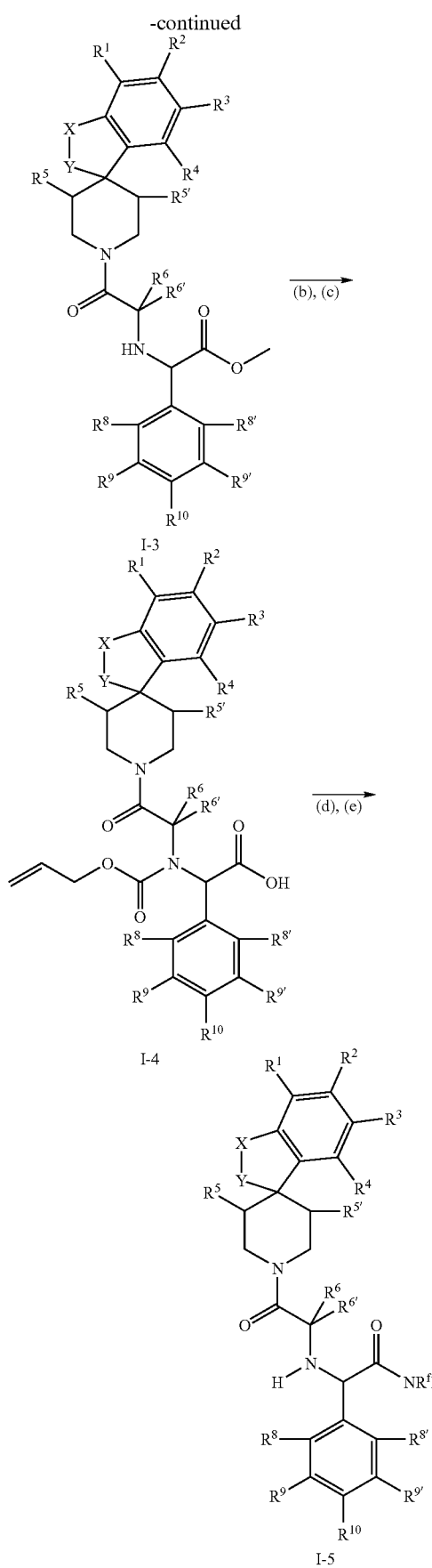
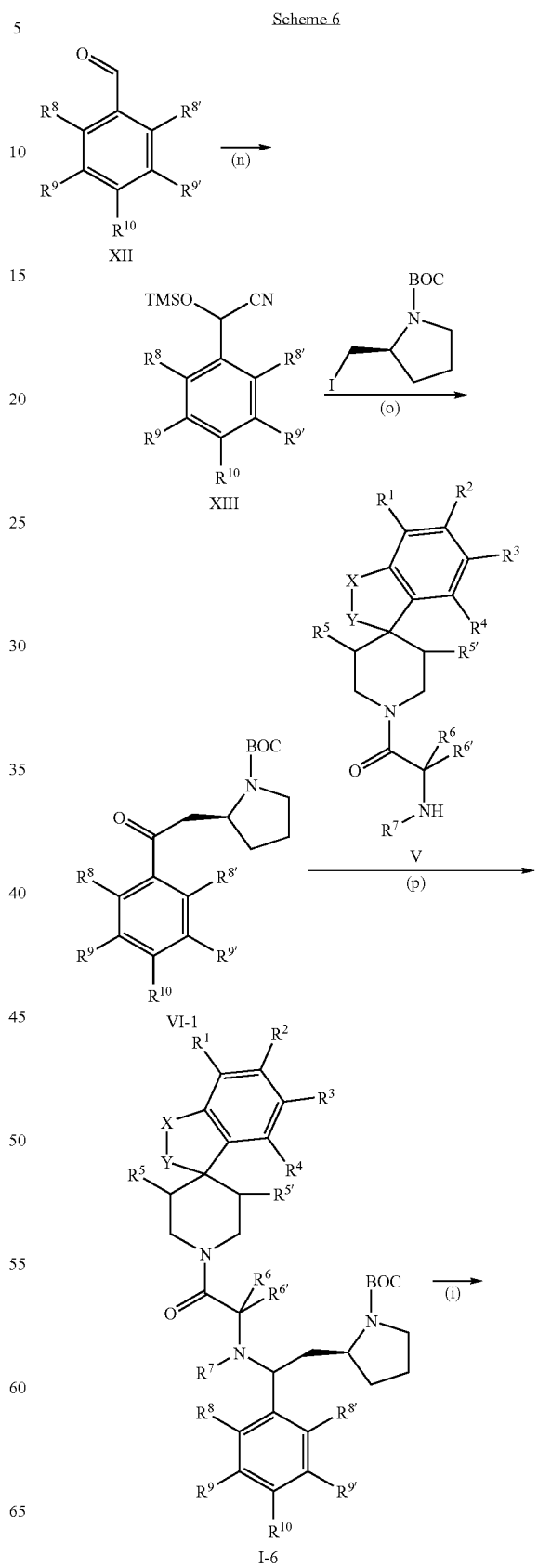

29

-continued

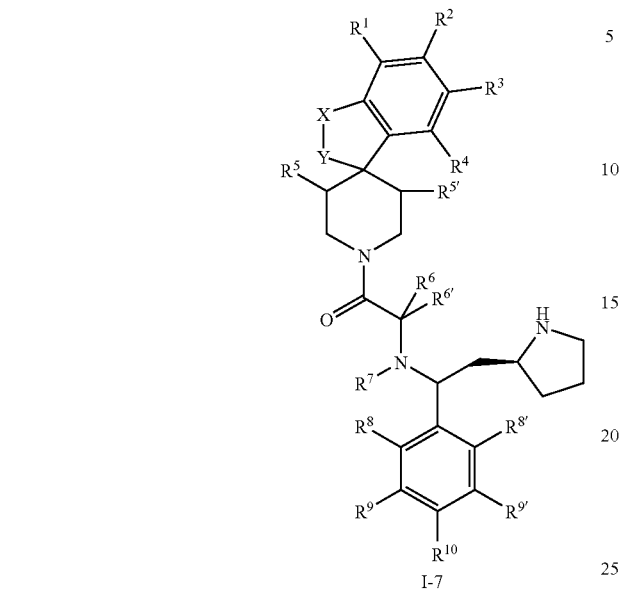

I-7

$R^7$ is hydrogen or $C_{1-6}$-alkyl

Synthetic Methods (Scheme 6):

(n) TMS-Cyanohydrine formation with a catalytic amount of TEA in neat aldehyde according to Sansano[5]: TMSCN, cat. TEA, neat, 0-20° C., 15 min (o) Deprotoantion of a TMS cyanohydrine with LDA at −70° C. (Huenig Umpolung)[6] and alkylation with an alkylation agent, e.g. a primary iodide.[7]: 1. LDA, THF, −70°, 30 mm; 2. Alkylation agent, THF, —70° C., 5 h, to 20° C. overnight (p) Reductive amination according to Mattson.[3] Imine formation in neat Ti(OiPr)$_4$: 1. Ti(OiPr)$_4$ neat; 2. NaBH$_3$CN, EtOH Scheme 7

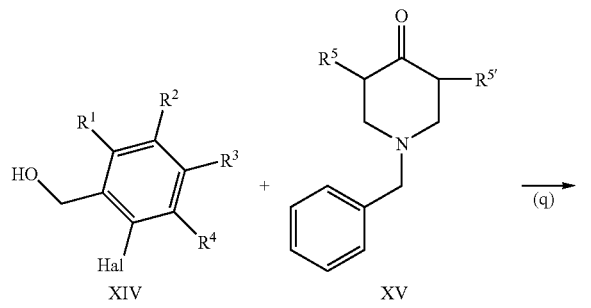

30

-continued

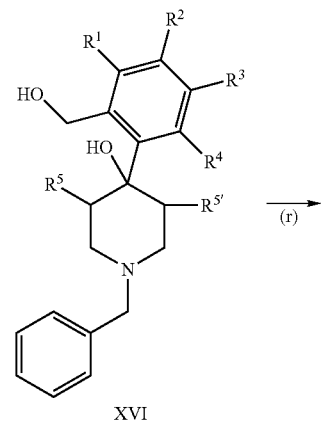

XVI

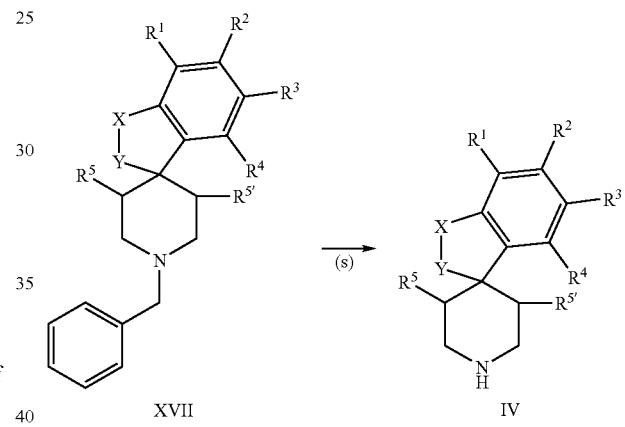

XVII          IV

Synthetic Methods (Scheme 7):

(q) Grignard reaction according to Sommer and Nielsen[8] but using an N-benzylpiperidone derivative (XV) instead of N-ethoxycarbonyl-piperidone: 1. 2.8 M EtMgCl (1 eq), THF; 2. Mg turnings (1 eq), THF, 66° C., 2.5 h; 3. N-benzylpiperidone derivative (1 eq), THF, 66° C., 2.5 h (r) Ring-closure reaction according to Sommer and Nielsen[8] with mesyl chloride and TEA: 1. TEA (2.1 eq); 2. MsCl (0.85 eq), THF, 66° C., 4 h (s) N-Debenzylation reaction under hydrogenolytic conditions. Pretreatment of the starting material with Raney nickel to remove impurites which may poison the palladium on charcoal catalyst. Filtration and addition of fresh catalyst may be neccessary to achieve full conversion: 1. Raney nickel (0.1 eq), 20°, 1 h; 2. 10% Pd/C (0.1 eq), H$_2$ (5 bar); EtOH, 40° C., 43 h.

Scheme 8

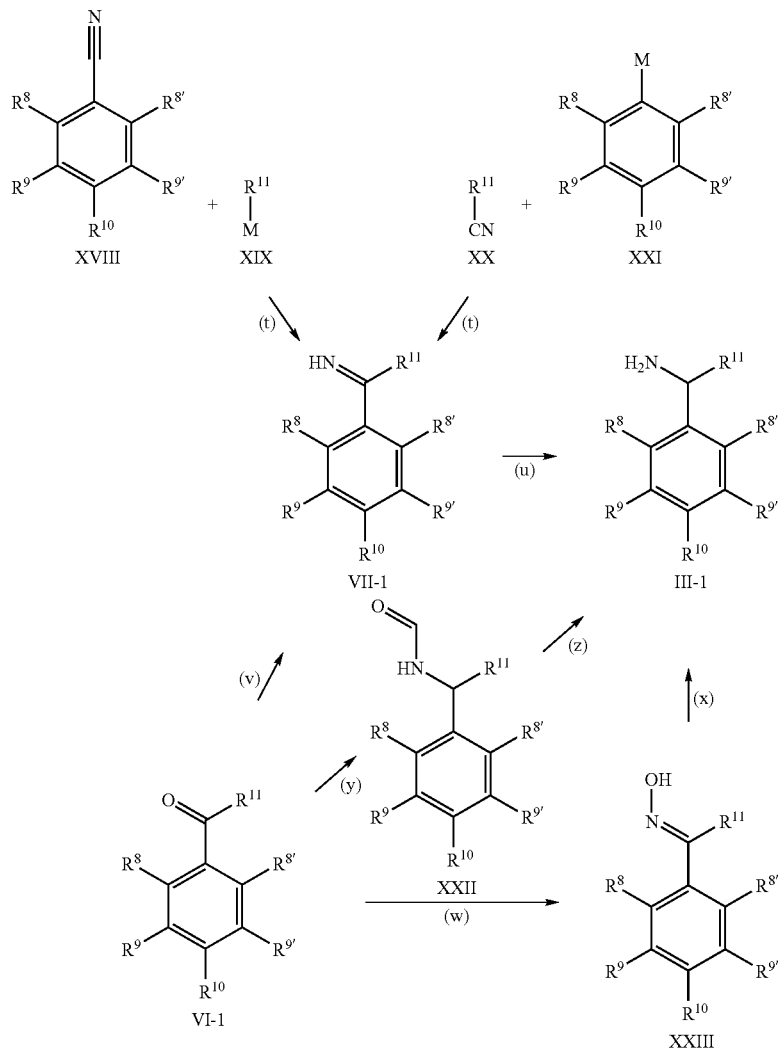

Synthetic Methods (Scheme 8):
(t) Grignard or organolithium addition to a nitrite in diethyl ether or THF, followed by quenching with MeOH or saturated $NH_4Cl$ solution in analogy to a previously reported method.[9,10]: $Et_2O$ or THF, reflux, 2 h
(u) Imine reduction with $NaBH_4$ in MeOH in analogy to a previously reported method[9] or with $LiAlH_4$ in THF in analogy to a previously reported method[10] or with Redal ($NaAlH_2(OCH_2CH_2OMe)_2$) in toluene/THF
(v) Imine formation from ketone and gaseous anhydrous ammonia in presence of stoichiometric amounts of $TiCl_4$ in analogy to a previously reported method.[11]: Excess $NH_3$ (gas), 1M $TiCl_4$ in toluene (2 eq), 0-40° C., 3 h
(w) Oxime formation: $NH_2OH$ HCl, NaOAc or $K_2CO_3$, MeOH, EtOH, or DMF, 20-100° C.
(x) Oxime reduction with catalytic hydrogenation under pressure (10% Pd/C, EtOH, HCl, $H_2$, 4 bar), or oxime reduction with $TiCl_4$—$NaBH_4$ (2eq-4 eq) in DME at 0-20° C. or with zinc in acetic acid at room temperature in analogy to previously reported methods.[12,13]

(y) Leuckart reaction with excess formamide in formic acid at high temperature: $HCONH_2$ (4eq), HCOOH, 180° C.
(z) Cleavage of formyl group with hot concentrated hydrochloric acid, 100° C., 1 h

REFERENCES

1. Abdel-Magid, A. F.; Carson, K. G.; Harris, B. D.; Maryanoff, C. A.; Shah, R. D. *J. Org. Chem.* 1996, 61, 3849-3862.
2. Perregaard, J. K.; Stenberg, J. W.; Moltzen, E. K. Wo Patent 9325527, 1993; *Chem. Abstr.* 1993,
3. Mattson, R. J.; Pham, K. M.; Leuck, D. J.; Cowen, K. A. *J. Org. Chem.* 1990, 55, 2552-2554.
4. Lecointe, L.; Rolland, V.; Pappalardo, L.; Roumestant, M. L.; Viallefont, P.; Martinez, J. *Journal of Peptide Research* 2000, 55, 300-307.
5. Baeza, A.; Najera, C.; de Gracia Retamosa, M.; Sansano, J. M. *Synthesis* 2005, 2787-2797.

6. Deuchert, K.; Hertenstein, U.; Huenig, S.; Wehner, G. *Chem. Ber.* 1979, 112, 2045-2061.
7. Ku, Y.-Y.; Cowart, M. D.; Sharma, P. N. Us Patent 2004260100, 2004; *Chem. Abstr.* 2004, Can 142:74442
8. Sommer, M. B.; Nielsen, O. Wo Patent 2004026855, 2004; *Chem. Abstr.* 2004, Can 140:303514
9. Dejaegher, Y.; Mangelinckx, S.; De Kimpe, N. *Synlett* 2002, 113-115.
10. Grisar, J. M.; Claxton, G. P.; Wiech, N. L.; Lucas, R. W.; MacKenzie, R. D.; Goldstein, S. *J. Med. Chem.* 1973, 16, 885-893.
11. Brenner, D. G.; Cavolowsky, K. M.; Shepard, K. L. *J. Heterocyclic Chem.* 1985, 22, 805-808.
12. Sasse, A.; Stark, H.; Ligneau, X.; Elz, S.; Reidemeister, S.; Ganellin, C. R.; Schwartz, J. C.; Schunack, W. *Bioorganic &Medicinal Chemistry* 2000, 8, 1139-1149.
13. Van Lommen, G. R. E.; Doyon, J. G. P.-O.; Van Wauwe, J. P. F.; Cools, M. L. L.; Coesemans, E. Wo Patent 2004069809, 2004; *Chem. Abstr.* 2004, Can 141:207206
14. Terrasson, V.; Marque, S.; Scarpacci, A.; Prim, D. *Synthesis* 2006, 1858-1862.
15. Fryer, R. I.; Earley, J. V.; Zally, W. *J. Heterocyclic Chem.* 1967, 4, 149-150.
16. Isaac, M.; Xin, T.; Edwards, L.; Begleiter, L.; Stefanac, T.; O'Brien, A.; Da Silva, K.; Arora, J.; Maddaford, S.; Slassi, A. Wo Patent 2004022528, 2004; *Chem. Abstr.* 2004, Can 140:271194
17. Camaggi, G.; Filippini, L.; Gusmeroli, M.; Mormile, S.; Signorini, E.; Garavaglia, C. Ep Patent 718280, 1996; *Chem. Abstr.* 1996, Can 125:168644
18. Walker, G. N.; Smith, R. T. *J. Org. Chem.* 1970, 36, 305-308.
19. Archer, G. A.; Sternbach, L. H. U.S. Pat. No. 3,531,467, 1970; *Chem. Abstr.* 1970, Can 74:13185
20. Archer, G. A.; Sternbach, L. H. U.S. Pat. No. 3,370,091, 1968; *Chem. Abstr.* 1968, Can 69:35764
21. Walser, A.; Flynn, T.; Fryer, R. I. *J. Heterocyclic Chem.* 1974, 11, 885-888.
22. Fryer, R. I.; Earley, J. V. *J. Heterocyclic Chem.* 1977, 14, 1435-1437.
23. Clerici, A.; Porta, O. *J. Org. Chem.* 1982, 47, 2852-2856.
24. Clerici, A.; Porta, O. *J. Org. Chem.* 1993, 58, 2889-2893.
25. Pfoertner, K. H.; Montavon, F.; Bernauer, K. *Helv. Chim. Acta* 1985, 68, 600-605.

The compounds of the present invention exhibit V1a activity, which may be detected as described below:

V1a Activity

Material & Method:

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells were resuspended in 30 ml freshly prepared ice cold Lysis buffer (50 mM HEPES, 1 mM EDTA, 10 mM MgCl2 adjusted to pH=7.4+complete cocktail of protease inhibitor (Roche Diagnostics)), homogenized with Polytron for 1 min, and sonicated on ice for 2×2 minutes at 80% intensity (Vibracell sonicator). The preparation was centrifuged 20 min at 500 g at 4° C., the pellet was discarded and the supernatant centrifuged 1 hour at 43,000 g at 4° C. (19,000 rpm). The pellet was resuspended in 12.5 ml Lysis buffer+ 12.5 ml Sucrose 20% and homogenized using a Polytron for 1-2 min. The protein concentration was determined by the Bradford method and aliquots are stored at −80° C. until use. For binding studies 60 mg Yttrium silicate SPA beads (Amersham) were mixed with an aliquot of membrane in binding buffer (50 mM Tris, 120 mM NaCl, 5 mM KCl, 2 mM CaCl2, 10 mM MgCl2) for 15 minutes with mixing. 50 ul of bead/membrane mixture was then added to each well of a 96 well plate, followed by 50 ul of 4 nM 3H-Vasopressin (American Radiolabeled Chemicals). For total binding measurement 100 ul of binding buffer were added to the respective wells, for non-specific binding 100 ul of 8.4 mM cold vasopressin and for compound testing 100 ul of a serial dilution of each compound in 2% DMSO. The plate was incubated 1 h at room temperature, centrifuged 1 min at 1000 g and counted on a Packard Top-Count. Non-specific binding counts were subtracted from each well and data was normalized to the maximum specific binding set at 100%. To calculate an IC 50 the curve was fitted using a non-linear regression model (XLfit) and the Ki is calculated using the Cheng-Prussoff equation.

| Example | pKi hV1a |
|---|---|
| 2 | 8.04 |
| 4 | 7.69 |
| 6 | 7.93 |
| 8 | 7.83 |
| 9 | 7.84 |
| 12 | 7.52 |
| 13 | 7.53 |
| 18 | 7.68 |
| 20 | 8.04 |
| 27 | 7.74 |
| 29 | 7.80 |
| 30 | 7.63 |
| 31 | 7.37 |
| 34 | 7.73 |
| 37 | 7.84 |
| 46 | 7.62 |
| 49 | 7.73 |
| 52 | 7.58 |
| 68 | 8.07 |
| 71 | 7.10 |
| 92 | 7.37 |
| 93 | 7.55 |

The present invention also provides pharmaceutical compositions containing compounds of the invention, for example compounds of formulae (I-a) to (I-h), or pharmaceutically acceptable salts thereof and a pharmaceutically acceptable carrier. Such pharmaceutical compositions can be in the form of tablets, coated tablets, dragees, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragees and hard gelatine capsules. Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

The following Examples illustrate the present invention without limiting it. All temperatures are given in degrees Celsius.

EXAMPLE A

Tablets of the following composition can be manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition can be manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture can be returned to the mixer, the talc can be added thereto and mixed thoroughly. The mixture can be filled by machine into hard gelatine capsules.

EXAMPLE C

Suppositories of the following composition can be manufactured:

|  | mg/supp. |
| --- | --- |
| Active substance | 15 |
| Suppository mass | 1285 |
| Total | 1300 |

The suppository mass can be melted in a glass or steel vessel, mixed thoroughly and cooled to 45° C. Thereupon, the finely powdered active substance can be added thereto and stirred until it has dispersed completely. The mixture can be poured into suppository moulds of suitable size, left to cool; the suppositories then can be removed from the moulds and packed individually in wax paper or metal foil.

EXAMPLES

Preparation of Intermediates

Intermediate 1: 3H-Spiro[2-benzofuran-1,4'-piperidine]

Step 1: 1-Benzyl-4-(2-hydroxymethyl-phenyl)-piperidin-4-ol

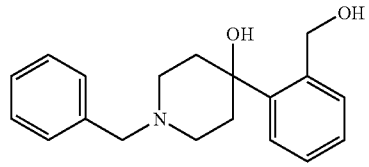

2-Bromobenzyl alcohol (100 g, 0.535 mol) was dissolved in THF (600 mL), and a 2.8 M solution of ethylmagnesium chloride (191 mL, 0.535 mol) was added slowly. During the addition the temperature increased, and the addition rate was adjusted to ensure gentle reflux. When the addition of EtMgCl was finished, magnesium turnings (13 g, 0.535 mol) were added in portions. Sufficient heat was applied to keep the reaction refluxing. When the addition was complete, the reaction mixture was refluxed gently for at least 2 h.

A solution of 1-benzyl-4-piperidone (101.2 mL, 0.535 mol) in THF (100 mL) was added to the Grignard reagent at about 65° C. When addition of the solution was finished, the reaction is refluxed for at least 2 h. The reaction mixture was cooled to room temperature.

The main part of the solvent was removed by distillation. Water (500 mL) and AcOEt (500 mL) were added. The reaction mixture was acidified to pH 3 by slow addition of 37% fuming HCl. The layers were separated, the organic layer with many impurities was discarded, the water layer was adjusted to pH 10 with KOH and extracted with AcOEt. The organic layer was evaporated to give a crude light yellow solid (90 g, 56%). MS: m/z=298 [M+H]$^+$.

Step 2: 1'-Benzyl-3H-spiro[2-benzofuran-1,4'-piperidine]

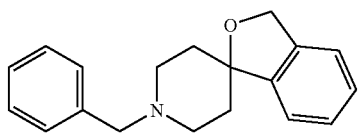

Crude 1-benzyl-4-(2-hydroxymethyl-phenyl)-piperidin-4-ol (180 g, 0.605 mol) was dissolved in THF (1000 mL). Triethylamine (176.18 mL, 1.27 mol) was added. A solution of methanesulfonyl chloride (33.03 mL, 0.424 mol) in THF (100 mL) was added slowly which caused an increase of the temperature from ambient to 53° C. The reaction was then refluxed for 4 h. Water (500 mL) and AcOEt (500 mL) were added to the reaction mixture. The organic phase was separated, dried and evaporated to give a brown oil (160 g). The crude product was purified by chromatography on silica gel with heptane/AcOEt 100:0 to 60:40 to give a light yellow solid (120 g, 71%). MS: m/z=280 [M+H]⁺.

Step 3: 3H-Spiro[2-benzofuran-1,4'-piperidine]

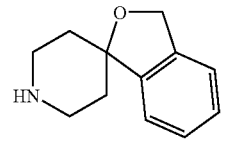

1'-Benzyl-3H-spiro[2-benzofuran-1,4'-piperidine] (119 g, 425.9 mmol) was dissolved EtOH (1 L) under argon and treated with Raney nickel (12 g) at ambient temperature for 1 h to absorb impurities which tended to poison the catalyst. Raney nickel was filtered off and the filtrate was hydrogenated in a steel autoclave over 10% Pd/C (Degussa Nr. 1835) (12 g) at 5 bar hydrogen pressure and 40° C. for 19 h. According to HPLC there was still 2.7% of starting material present. Thus the catalyst was filtered off, fresh 10% Pd/C (4 g) was added to the filtrate, and hydrogenation under the same condition was continued for 24 h. Filtration of the catalyst and evaporation of EtOH gave a light yellow oil, which crystallized spontaneously upon stirring with heptane (1 L) to give a white solid (65 g, 80%). MS: m/z=190 [M+H]⁺.

Intermediate 2: 1'-(Chloroacetyl)-spiro[isobenzofuran-1(3H),4'-piperidine]

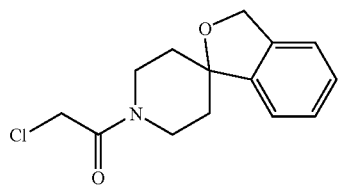

3H-spiro[2-benzofuran-1,4'-piperidine] (5 g, 26 mmol) was dissolved in THF (100 mL) and cooled in ice. Then N-ethyldiisopropylamine (4.94 mL, 29 mmol) and chloroacetyl chloride (2.31 mL, 29 mmol) were added. The mixture was stirred at 20° C. for 15 min. The solid was filtered off and washed with THF. The filtrate was evaporated to dryness and the residue was purified by flash chromatography on silica gel with heptane/AcOEt 70:30. One obtained light yellow crystals (6.5 g, 92%). MS: m/z=266 [M+H]⁺.

Intermediate 3: 1'-(Chloroacetyl)-3H-spiro[2-benzofuran-1,4'-piperidine]-3-one

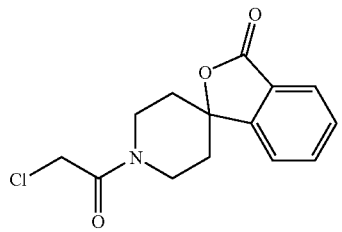

The title compound was prepared in analogy to intermediate 2 using 3H-spiro[2-benzofuran-1,4'-piperidin]-3-one. MS: m/z=280 [M+H]⁺.

Intermediate 4: (RS)-{Allyloxycarbonyl-[(4-chlorophenyl)-phenyl-methyl]-amino}-acetic acid Step 1: (RS)-{[(4-Chloro-phenyl)-phenyl-methyl]-amino}-acetic acid ethyl ester

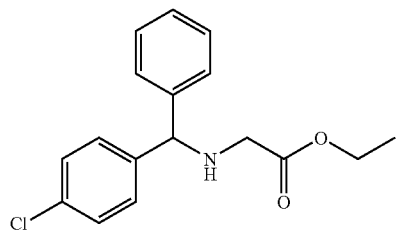

4-Chlorobenzhydrylamine (6.6 g, 30.3 mmol), obtained from the corresponding hydrochloride by extraction with AcOiPr and 10% NaHCO₃, glyoxylic acid ethyl ester (66 mL, 33.3 mmol), sodium triacetoxyborohydride (14.1 g, 66.7 mmol) (exothermic 38° C.) and acetic acid (0.173 mL, 3 mmol) in DCM (100 mL) were stirred under nitrogen at 20° C. for 24 h. The reaction mixture was extracted with 10% Na₂CO₃ (2×). The crude product was purified by chromatography on silica gel in heptane/isopropyl acetate 10:1. One obtained 8.4 g (91%) of a colorless oil. MS: m/z=304 [M+H]⁺.

Step 2: (RS)-{Allyloxycarbonyl-[(4-chloro-phenyl)-phenyl-methyl]-amino}-acetic acid ethyl ester

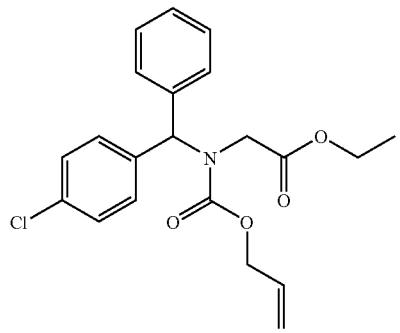

(RS)-{[(4-Chloro-phenyl)-phenyl-methyl]-amino}-acetic acid ethyl ester (18 g, 59 mmol) was dissolved under nitrogen in DCM (1500 mL), N-ethyldiisopropylamine (12.2 mL, 71 mmol) was added, cooled in ice and treated with a solution of allyl chloroformate (6.4 mL, 71 mmol) in DCM (50 mL). Stirring at 20° C. was continued for 16 h. The solution was extracted with 1 M citric acid (200 mL) and 50% NaCl solution. The crude product was purified by chromatography on silica gel in heptane with a gradient of ethyl acetate from 0-50% in 60 min. One obtained 18.1 g (78%) of colorless oil. MS: m/z=388 [M+H]⁺.

Step 3: (RS)-{Allyloxycarbonyl-[(4-chloro-phenyl)-phenyl-methyl]-amino}-acetic acid

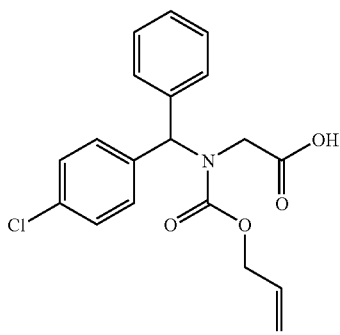

(RS)-{Allyloxycarbonyl-[(4-chloro-phenyl)-phenyl-methyl]-amino}-acetic acid ethyl ester (18 g, 46.4 mmol) was dissolved in THF (60 mL), water (60 mL), and MeOH (60 mL) and treated with lithium hydroxide monohydrate (3.9 g, 92 mmol) at 20° C. for 2 h. The mixture was evaporated and extracted with AcOEt, 1 N HCl and 50% NaCl. The crude product was crystallized from heptane/ethyl acetate 10:1 (100 mL). One obtained 11.08 g (66%) of white crystals. MS: m/z=358 [M+H]$^+$.

Intermediate 5: C-(3-Chloro-phenyl)-C-phenyl-methylamine

Step 1: C-(3-Chloro-phenyl)-C-phenyl-methyleneamine

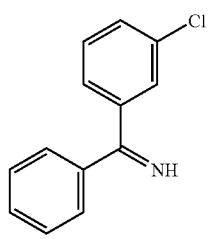

3-Chlorobenzophenone (5 g, 23 mmol) was dissolved in toluene (100 mL) under argon and cooled in ice. Gaseous ammonia was bubbled through the solution for 30 min. This led to a yellow precipitate. The resulting slurry was heated at 40° C. for 3 h in order to complete the reaction. The yellow suspension was poured into ice-cold 10% NaHCO$_3$ solution (400 mL), extracted with toluene (2×400 mL), and washed to neutrality with 50% NaCl solution. One obtained 4.8 g (96%) of a brown oil. MS: m/z=215 [M]$^+$.

Step 2: C-(3-Chloro-phenyl)-C-phenyl-methylamine

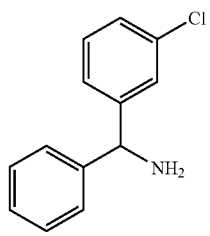

C-(3-Chloro-phenyl)-C-phenyl-methyleneamine (4.58 g, 21.2 mmol) was dissolved in methanol (40 mL) and treated in two portions with sodium borohydride (803 mg, 21.2 mmol). There was an exothermic evolution of hydrogen (40° C.). After 1 h the methanol was evaporated and the residue extracted with ethyl acetate, 10% Na$_2$CO$_3$, and 50% NaCl. One obtained a faint-yellow oil (4.2 g, 90%). Chromatography on silica gel with a gradient of 0-50% AcOEt in heptane afforded a colorless oil (3.8 g, 81%). MS: m/z=217 [M]$^+$.

Intermediate 6: (RS)-C-(3,4-Dichloro-phenyl)-C-phenyl-methylamine

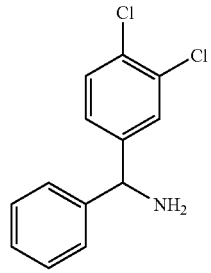

The title compound CAS [742107-55-7] is known from literature.[13]

Intermediate 7: (RS)-C-(2,4-Dichloro-phenyl)-C-phenyl-methylamine

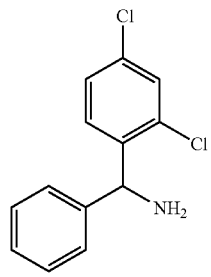

The title compound was prepared from 2,4-dichloro benzonitrile and a) phenyl magnesium bromide b) NaBH$_4$ in MeOH in analogy to known methods.[9]

Intermediate 8: (RS)-C-Phenyl-C-(3-trifluoromethyl-phenyl)-methylamine

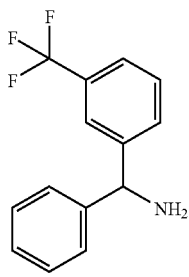

The title compound CAS [70428-92-1] is known from literature[10]

Intermediate 9: (RS)-C-(4-Fluoro-phenyl)-C-(3-trifluoromethyl-phenyl)-methylamine

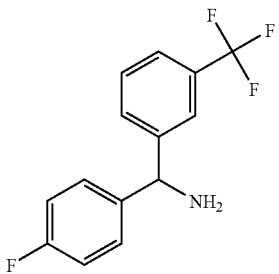

The title compound may be prepared in analogy to Intermediate 8.[10]

Intermediate 10: (RS)-C-p-tolyl-C-(3-trifluoromethyl-phenyl)-methylamine

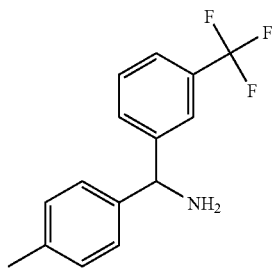

The title compound may be prepared in analogy to Intermediate 8.[10]

Intermediate 11: (RS)-C-(4-Methoxy-phenyl)-C-(3-trifluoromethyl-phenyl)-methylamine

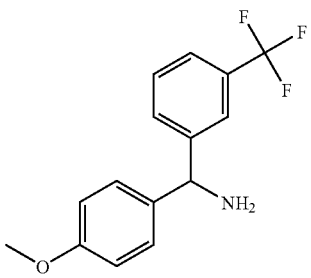

The title compound may be prepared in analogy to Intermediate 8.[10]

Intermediate 12: (RS)-[2-(Amino-phenyl-methyl)-4-chloro-phenyl]-ethyl-methyl-amine

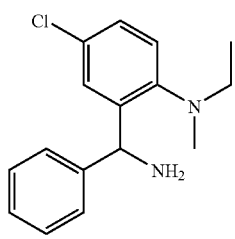

The title compound was prepared from (5-chloro-2-methylamino-phenyl)-phenyl-methanone by treatment with NaH and ethyliodide in DMF, followed by oxime formation and oxime reduction by previously reported methods.[12]

Intermediate 13: (RS)-C-Phenyl-C-pyrimidin-2-yl-methylamine

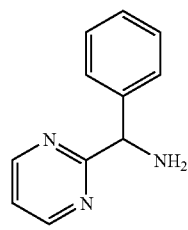

The title compound CAS [907594-98-3] is known from literature.[14]

Intermediate 14: (RS)-C-Phenyl-C-(4-trifluoromethyl-phenyl)-methylamine

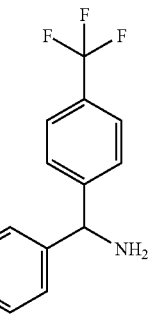

The title compound CAS [154233-38-2] is known from literature.[10]

Intermediate 15: (RS)-[2-(1-Amino-2-propenyl-penta-2,4-dienyl)-4-chloro-phenyl]-methyl-amine

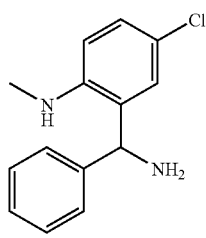

The title compound CAS [22141-68-0], known from literature, was prepared from (5-chloro-2-methylamino-phenyl)-phenyl-methanone by oxime formation followed oxime reduction by previously reported methods.[12]

Intermediate 16: (RS)-[C-(2-Chloro-5-trifluorom-ethyl-phenyl)-C-phenyl-methylamine

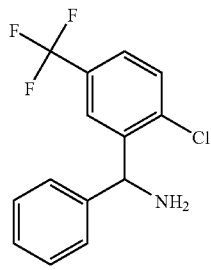

The title compound CAS [802845-82-5] is known from literature.[15]

Intermediate 17: (RS)-[2-(Amino-phenyl-methyl)-phenyl]-dimethyl-amine

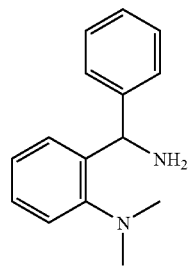

The title compound was prepared from (2-dimethylamino-phenyl)-phenyl-methanone by oxime formation followed oxime reduction by previously reported methods.[12]

Intermediate 18: (2R)-2-Amino-N-(4-chloro-phenyl)-2-phenyl-acetamide

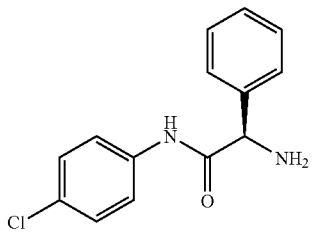

The title compound CAS [672962-56-0] is known from literature.[16]

Intermediate 19: (RS)-3-Amino-3-phenyl-propionic acid benzyl ester

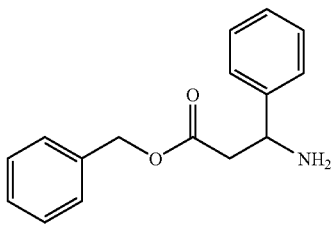

The title compound CAS [116794-78-6] is known in literature.[17]

Intermediate 20: (RS)-C-Phenyl-C-m-tolyl-methylamine

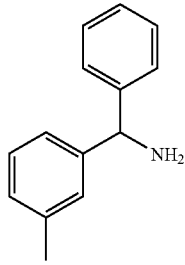

The title compound CAS [55095-20-0] is known from literature.[12]

Intermediate 21: (RS)-2-(Amino-phenyl-methyl)-4-chloro-phenol

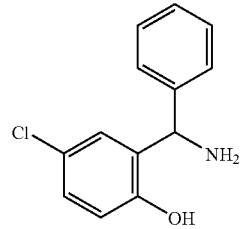

The title compound CAS [26965-58-2] is known from literature.[18]

Intermediate 22: (RS)-[2-(Amino-phenyl-methyl)-4-chloro-phenylamino]-acetic acid ethyl ester

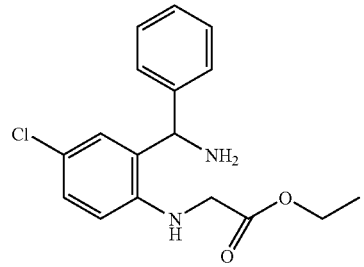

The title compound CAS [10456-62-9] is known from literature.[19]

Intermediate 23: (RS)-2-(Amino-phenyl-methyl)-4-chloro-phenylamine

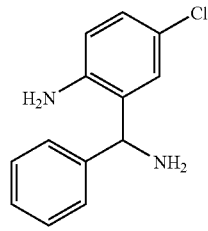

The title compound CAS [1824-70-0] is known from literature.[20]

Intermediate 24: (RS)-Hepta-2,4-diene-3-sulfonic acid [2-(amino-phenyl-methyl)-phenyl]-amide

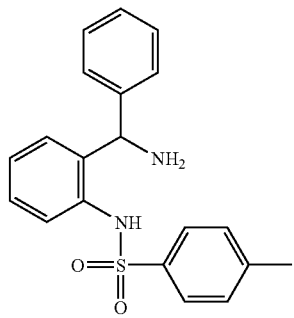

The title compound was prepared from N-(2-benzoyl-phenyl)-4-methyl-benzenesulfonamide by oxime formation followed oxime reduction by previously reported methods.[12]

Intermediate 25: (RS)-2-[Amino-(2-amino-5-chloro-phenyl)-methyl]-phenol

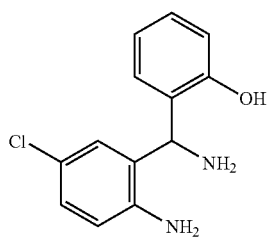

The title compound CAS [55076-02-3] is known in literature.[21]

Intermediate 26: (RS)-C-[2-(1H-Imidazol-2-yl)-phenyl]-C-phenyl-methylamine

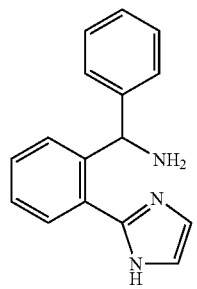

The title compound CAS [66079-72-9] is known in literature.[22]

Intermediate 27: (RS)-2-Amino-N-(4-chloro-2-hydroxymethyl-phenyl)-2-phenyl-acetamide

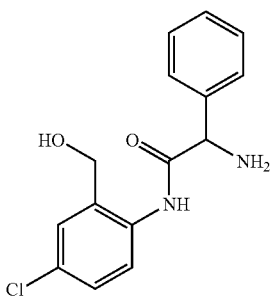

The title compound was prepared from BOC-phenylglycine and 2-amino-5-chloro-benzoic acid methyl ester by peptide coupling, followed by ester reduction and BOC cleavage.

Intermediate 28: (1S,2R)-2-Amino-2-(4-chloro-phenyl)-1-(4-morpholin-4-yl-phenyl)-ethanol

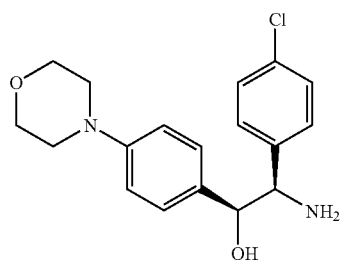

Intermediate 29: (1S,2R)-2-Amino-2-(4-chloro-phenyl)-1-(2-chloro-phenyl)-ethanol

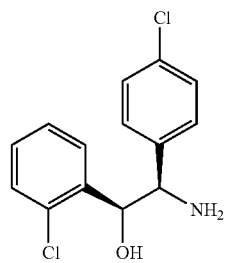

Intermediate 30: (RS)-4-Amino-4-(4-chloro-phenyl)-butyric acid

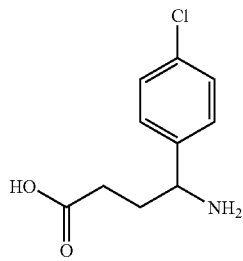

The title compound was prepared from intermediate 19 by hydrolysis of the ester group.

Intermediate 31: (1RS,2RS)-1-Amino-1-(4-chloro-phenyl)-2-pyridin-2-yl-propan-2-ol

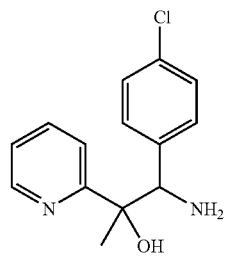

The title compound can be prepared according to previously reported methods.[23-25]

Intermediate 32: (2RS,3RS)-3-Amino-3-(4-chlorophenyl)-2-methyl-2-pyridin-3-yl-propan-1-ol

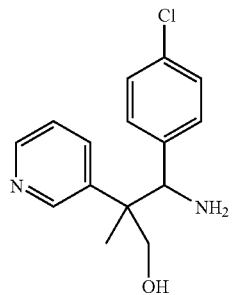

Intermediate 33: (1RS,2RS)-1-Amino-1-(4-chlorophenyl)-2-phenyl-propan-2-ol

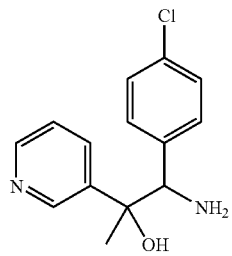

The title compound can be prepared according to previously reported methods.[23-25]

Intermediate 34: (1RS,2RS)-1-Amino-1-(4-chlorophenyl)-2-pyridin-4-yl-propan-2-ol

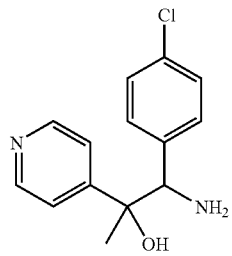

The title compound can be prepared according to previously reported methods[23-25].

Intermediate 35: (2R)-1-Oxo-1-(1'H,3H-spiro[2-benzofuran-1,4'-piperidin]-1'-yl)propan-2-amine trifluoroacetate Step 1: tert-Butyl [(1R)-1-methyl-2-oxo-2-(1'H,3H-spiro[2-benzofuran-1,4'-piperidin]-1'-yl)ethyl]carbamate

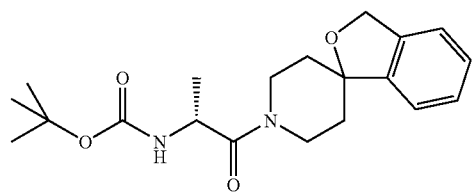

To a stirred suspension of BOC-D-alanine (1.2 g, 6 mmol) and 3H-spiro[2-benzofuran-1,4'-piperidine] (1.27 g, 7 mmol) and N,N,N',N'-tetramethyl-o-(benzotriazol-1-yl)uronium hexafluorophosphate (HBTU) in THF (20 mL) was added slowly triethylamine (2.92 mL, 21 mmol) without exceeding 27° C. The white suspension was stirred for 12 h at 20° C., filtered and evaporated. The crude oil was purified by chromatography with heptane/AcOEt 1:2 to give a white solid (2.1 g, 91%). MS: m/z=361 [M+H]$^+$.

Step 2: (2R)-1-Oxo-1-(1'H,3H-spiro[2-benzofuran-1,4'-piperidin]-1'-yl)propan-2-amine trifluoroacetate

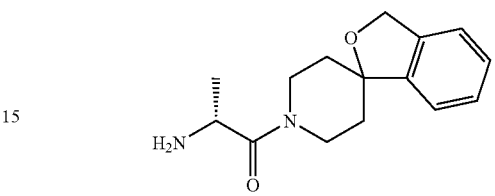

tert-Butyl [(1R)-1-methyl-2-oxo-2-(1'H,3H-spiro[2-benzofuran-1,4'-piperidin]-1'-yl)ethyl]carbamate (2.1 g, 6 mmol) dissolved in DCM (50 mL), trifluoroacetic acid (2.23 mL, 29 mmol) added and stirred at 30° C. 1 h. Evaporation and chromatography on silica gel with DCM/MeOH 10:1 gave a white foam (2.1 g, 96%). MS: m/z=261 [M+H]$^+$.

Intermediate 36: 2-Methyl-1-oxo-1-(1'H,3H-spiro[2-benzofuran-1,4'-piperidin]-1'-yl)propan-2-amine Step 1: tert-Butyl [1,1-dimethyl-2-oxo-2-(1'H,3H-spiro[2-benzofuran-1,4'-piperidin]-1'-yl)ethyl]carbamate

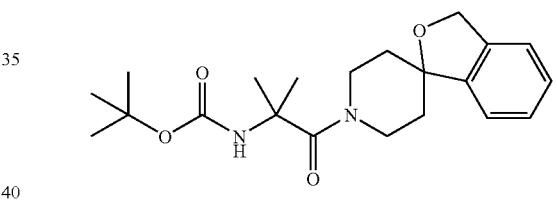

To a stirred suspension of BOC-2-aminoisobutyric acid (4 g, 19.7 mmol) and 3H-spiro[2-benzofuran-1,4'-piperidine] (3.7 g, 19.7 mmol) and N,N,N',N'-tetramethyl-o-(benzotriazol-1-yl)uronium hexafluorophosphate (HBTU) (11.2 g, 29.5 mmol) in THF (70 mL) cooled in ice, triethylamine (8.2 mL, 59 mmol) was added slowly and stirring without cooling was continued for 24 h. The mixture was filtered, evaporated to dryness and extracted with AcOEt, 1 M citric acid, 50% NaCl, 10% Na$_2$CO$_3$, 50% NaCl. The resulting foam was dissolved in heptane/AcOEt 1:2 (80 mL) which led to spontaneous crystallization. One obtained 5.54 g (75%) of white crystals. MS: m/z=375 [M+H]$^+$.

Step 2: 2-Methyl-1-oxo-1-(1'H,3H-spiro[2-benzofuran-1,4'-piperidin]-1'-yl)propan-2-amine

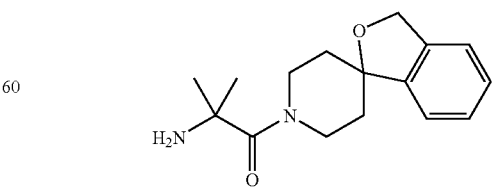

tert-Butyl [1,1-dimethyl-2-oxo-2-(1'H,3H-spiro[2-benzofuran-1,4'-piperidin]-1'-yl)ethyl]carbamate (5.5 g, 14.7 mmol) was dissolved in DCM (50 mL) under nitrogen and treated with TFA (711 mL, 147 mmol) at 20° C. for 2 h. Extraction: DCM, 10% Na$_2$CO$_3$. Evaporated to dryness and purified by chromatography on silica gel in DCM/MeOH 10:1. One obtained 3.48 g (86%) white crystals. MS: m/z=275 [M+H]$^+$.

Intermediate 37: 2R)-{[(Allyloxy)carbonyl][2-oxo-2-(1'H,3H-spiro[2-benzofuran-1,4'-piperidin]-1'-yl)ethyl]amino}(phenyl)acetic acid Step 1: Methyl (2R)-{[2-oxo-2-(1'H,3H-spiro[2-benzofuran-1,4'-piperidin]-1'-yl)ethyl]amino}(phenyl)acetate

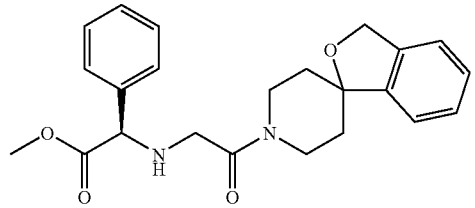

(R)-(–)-2-Phenylglycine methylester (1.5 g, 7.5 mmol) and 1'-(chloroacetyl)-spiro[isobenzofuran-1(3H),4'-piperidine] (1.98 g, 7.5 mmol) were dissolved in DMF (8 mL). Then triethylamine (4.12 mL, 30 mmol) was added and the reaction mixture was stirred at 80° C. over night. Evaporation and extraction with AcOEt and water gave 2.15 g (73%) of crude yellow oil. MS: m/z=395 [M+H]$^+$.

Step 2: Methyl (2R)-{[(allyloxy)carbonyl][2-oxo-2-(1'H,3H-spiro[2-benzofuran-1,4'-piperidin]-1'-yl)ethyl]amino}(phenyl)acetate

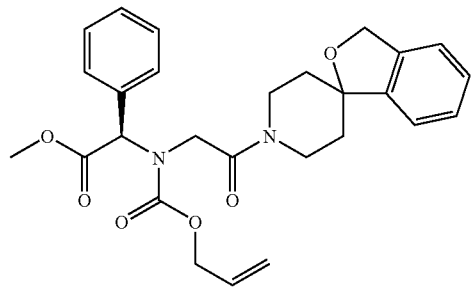

Methyl (2R)-{[2-oxo-2-(1'H,3H-spiro[2-benzofuran-1,4'-piperidin]-1'-yl)ethyl]amino}(phenyl)acetate (1 g, 2.53 mmol) was dissolved in DCM (20 mL), N-ethyl-diisopropylamine (0.47 mL, 0.28 mmol) was added, cooled in ice and treated with allyl chloroformate (0.25 mL, 0.28 mmol). Stirring was continued for 2 h. The reaction mixture was extracted with DCM, 1N HCl, and 50% NaCl. The crude product was purified by chromatography on silica gel with heptane/AcOEt 2:1 to give a colorless oil (1 g, 82%). MS: m/z=479 [M+H]$^+$.

Step 3: (2R)-{[(Allyloxy)carbonyl][2-oxo-2-(1'H,3H-spiro[2-benzofuran-1,4'-piperidin]-1'-yl)ethyl]amino}(phenyl)acetic acid

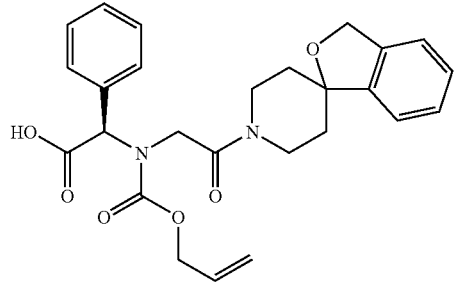

Methyl (2R)-{[(allyloxy)carbonyl][2-oxo-2-(1'H,3H-spiro[2-benzofuran-1,4'-piperidin]-1'-yl)ethyl]amino}(phenyl)acetate (1.1 g, 2.3 mmol) was dissolved in THF (10 mL), water (10 mL), and MeOH (10 mL) and treated with lithium hydroxide monohydrate (0.386 g, 9.2 mmol) at 20° C. for 2 h. The mixture was evaporated and extracted with 1 N HCl and EtOAc. One obtained a white foam (825 mg, 77%). MS: m/z=463 [M+H]$^+$.

Intermediate 38: (2R)-{[(Allyloxy)carbonyl][2-oxo-2-(1'H,3H-spiro[2-benzofuran-1,4'-piperidin]-1'-yl)ethyl]amino}(4-chlorophenyl)acetic acid Step 1: Methyl (2R)-(4-chlorophenyl){[2-oxo-2-(1'H,3H-spiro[2-benzofuran-1,4'-piperidin]-1'-yl)ethyl]amino}acetate

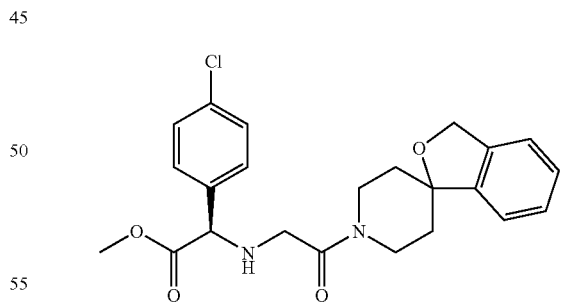

(R)-Amino-(4-chloro-phenyl)-acetic acid methylester (1.8 g, 7.6 mmol) and 1'-(chloroacetyl)-spiro[isobenzofuran-1(3H),4'-piperidine](2.02 g, 7.6 mmol) were dissolved in DMF (20 mL). Then triethylamine (4.23 mL, 30 mmol) was added and the reaction mixture was stirred at 80° C. over night. Evaporation and extraction with AcOEt and water gave a crude yellow oil, which was purified by chromatography on silica gel in heptane/AcOEt 1:2 affording a light brown oil (2 g, 61%). MS: m/z=429 [M+H]$^+$.

Step 2: Methyl (2R)-{[(allyloxy)carbonyl][2-oxo-2-(1'H,3H-spiro[2-benzofuran-1,4'-piperdin]1'-yl)ethyl]amino}(4-chlorophenyl)acetate

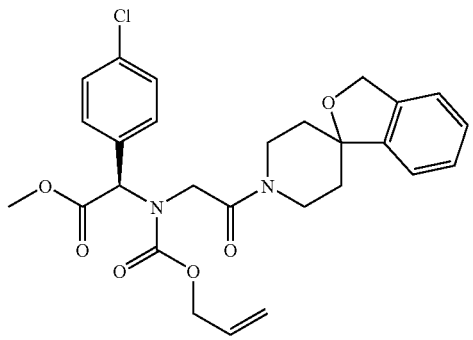

Methyl (2R)-(4-chlorophenyl){[2-oxo-2-(1'H,3H-spiro[2-benzofuran-1,4'-piperidin]-1'-yl)ethyl]amino}acetate (1.8 g, 4.2 mmol) was dissolved in DCM (20 mL), triethylamine (0.64 mL, 4.6 mmol) was added, cooled in ice and treated with allyl chloroformate (0.42 mL, 4.6 mmol). Stirring was continued for 2 h. The reaction solution was extracted with DCM, 1N HCl, and 50% NaCl. The crude product was purified by chromatography on silica gel with heptane/AcOEt 1:1 to give a white foam (1.2 g, 46%). MS: m/z=479 [M+H]$^+$.

Step 3: (2R)-{[(Allyloxy)carbonyl][2-oxo-2-(1'H,3H-spiro[2-benzofuran-1,4'-piperidin]-1'-yl)ethyl]amino}(4-chlorophenyl)acetic acid

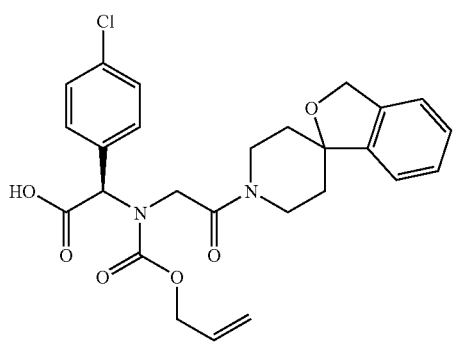

Methyl (2R)-{[(allyloxy)carbonyl][2-oxo-2-(1'H,3H-spiro[2-benzofuran-1,4'-piperidin]-1'-yl)ethyl]amino}(4-chlorophenyl)acetate (0.8 g, 1.55 mmol) was dissolved in THF (10 mL), water (10 mL), and MeOH (10 mL) and treated with lithium hydroxide monohydrate (0.262 g, 6.2 mmol) at 20° C. for 2 h. The mixture was evaporated and extracted with 1 N HCl and AcOEt. One obtained a white foam (825 mg, 77%). MS: m/z=499 [M+H]$^+$.

Intermediate 39: (R)-2-[2-(3-Chloro-phenyl)-2-oxo-ethyl]-pyrrolidine-1-carboxylic acid tert-butyl ester -

Step 1: (3-Chloro-phenyl)-trimethylsilanyloxy-acetonitrile

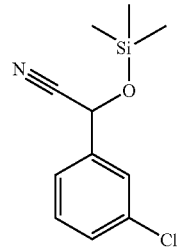

3-Chlorobenzaldehyde (20 g, 142 mmol) and triethylamine (1 mL, 7 mmol) were stirred under nitrogen and cooled in ice. Then trimethylsilyl cyanide (17.8 mL, 142 mmol) was added slowly (exothermic). The mixture was stirred for 15 min at 20° C. and then directly distilled in a Kugelrohr at 100° C./0.2 mbar. One obtained 31.3 g (91%) of a colorless oil. MS: m/z=239 [M$^+$].

Step 2: (R)-2-[2-(3-Chloro-phenyl)-2-oxo-ethyl]-pyrrolidine-1-carboxylic acid tert-butyl ester

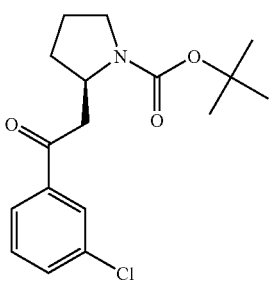

Diisopropylamine (764 uL, 5.4 mmol) was dissolved in THF (15 mL) under nitrogen and cooled to −70° C. Then a 1.6 M solution of butyllithium in hexane (3.4 mL, 5.4 mmol) was added and stirring at −70° C. was continued for 15 min. Then a solution of (3-chloro-phenyl)-trimethylsilanyloxy-acetonitrile (1.18 g, 4.9 mmol) in THF (5 mL) was added and stirring at −70° C. was continued for 30 min, producing a yellow color. Then a solution of (S)-2-iodomethyl-pyrrolidine-1-carboxylic acid tert-butyl ester (1.53 g, 4.9 mmol) in THF (5 mL) was added and stirring at −70° C. was continued for 5 h and then allowed to warm up to 20° C. and stirred overnight. The mixture was extracted with AcOEt, 1 M citric acid, and 50% NaCl. The crude product was purified by flash chromatography on silica gel with a heptane/AcOEt gradient 0-15%. One obtained 500 mg (31%) of a yellow oil. MS: m/z=224 [M$^+$].

EXAMPLES

Example 1

(RS)-Allyl [(4-chlorophenyl)(phenyl)methyl][2-oxo-2-(1'H,3H-spiro[2-benzofuran-1,4'-piperidin]-1'-yl)ethyl]carbamate

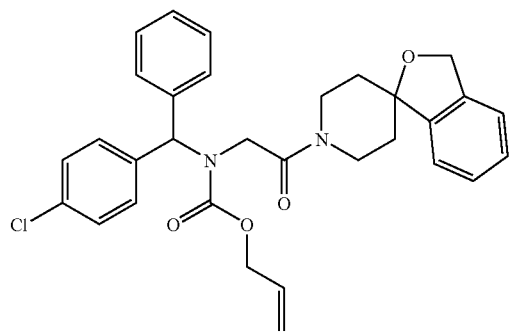

(RS)-{Allyloxycarbonyl-[(4-chloro-phenyl)-phenyl-methyl]-amino}-acetic acid (500 mg, 1.39 mmol), 3H-spiro[2-benzofuran-1,4'-piperidine] (263 mg, 1.39 mmol), and N,N,N',N'-tetramethyl-O-(benzotriazol-1-yl)uronium hexafluorophosphate (HBTU) (685 mg, 1.8 mmol) were suspended in THF (5 mL) and treated with triethylamine (639 uL, 4.59 mmol) for 16 h at 20° C. The mixture was extracted with AcOEt, 1M HCl, and 50% NaCl. The crude product was purified by chromatography on silica gel in DCM/AcOEt 5:1. One obtained 650 mg (88%) of a white foam. MS: m/z=532 [M+H]$^+$.

Example 2

(RS)-N-[(4-Chlorophenyl)(phenyl)methyl]-2-oxo-2-(1'H,3H-spiro[2-benzofuran-1,4'-piperidin]-1'-yl)ethanamine

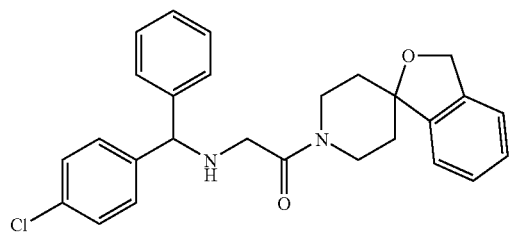

(RS)-Allyl [(4-chlorophenyl)(phenyl)methyl][2-oxo-2-(1'H,3H-spiro[2-benzofuran-1,4'-piperidin]-1'-yl)ethyl]carbamate (550 mg, 1.04 mmol) and pyrrolidine (0.856 mL, 10.4 mmol) were dissolved in DCM (5 mL) under nitrogen and treated with tetrakis(triphenylphosphine)palladium(0) (48 mg, 0.04 mmol) at 20° C. for 5 h. The mixture was evaporated to dryness (HV) and the residue was purified by chromatography on silica gel in DCM/AcOEt 85:15. One obtained 390 mg (84%) of a white foam. MS: m/z=447 [M+H]$^+$.

Examples 3 and 4

N-[(−)-(4-Chlorophenyl)(phenyl)methyl]-2-oxo-2-(1'H,3H-spiro[2-benzofuran-1,4'-piperidin]-1'-yl)ethanamine and N-[(+)-(4-chlorophenyl)(phenyl)methyl]-2-oxo-2-(1'H,3H-spiro[2-benzofuran-1,4'-piperidin]-1'-yl)ethanamine

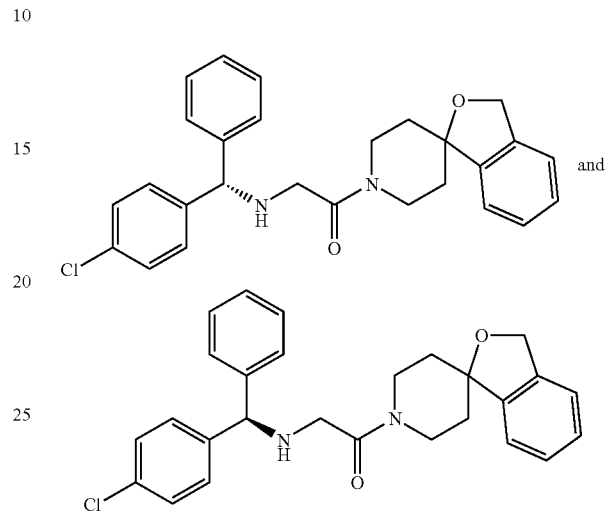

(RS)-N-[(4-Chlorophenyl)(phenyl)methyl]-2-oxo-2-(1'H,3H-spiro[2-benzofuran-1,4'-piperidin]-1'-yl)ethanamine (200 mg) was separated into enantiomers by chromatography on Chiracel OD with heptane/EtOH 95:5. One obtained in order of elution first the (−)-enantiomer (57 mg) and then the (+)-enantiomer (63 mg).

Example 5

(RS)-N-[1-(4-Chlorophenyl)ethyl]-2-oxo-2-(1'H,3H-spiro[2-benzofuran-1,4'-piperidin]-1'-yl)ethanamine

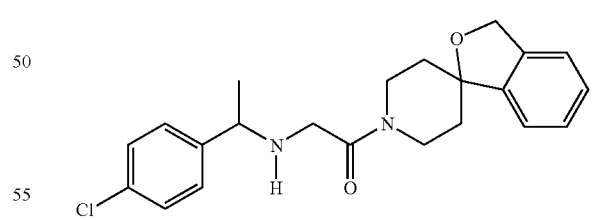

1'-(Chloroacetyl)-spiro[isobenzofuran-1(3H),4'-piperidine] (50 mg, 0.188 mmol)) and (RS)-1-(4-chloro-phenyl)-ethylamine (29.3 mg, 0.188 mmol) were dissolved in dry DMF (0.8 mL). Then triethylamine (0.079 mL, 0.564 mmol) was added and the reaction mixture was shaken at 25° C. for 2.5 days. Water (0.1 mL) was added and the whole mixture was directly purified by preparative HPLC on YMC-AQ column with a gradient of MeCN in water from 0-90% in 15 min. MS: m/z=385 [M+H]$^+$.

Example 6

N-(Diphenylmethyl)-2-oxo-2-(1'H,3H-spiro[2-benzofuran-1,4'-piperidin]-1'-yl)ethanamine

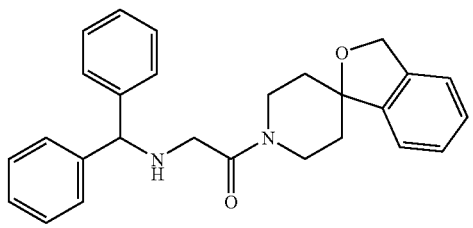

The title compound was prepared in analogy to example 5 using diphenylmethylamine instead of (RS)-1-(4-chlorophenyl)-ethylamine. MS: m/z=413 [M+H]+.

Example 7

N-[2-Oxo-2-(1'H,3H-spiro[2-benzofuran-1,4'-piperidin]-1'-yl)ethyl]-9H-fluoren-9-amine

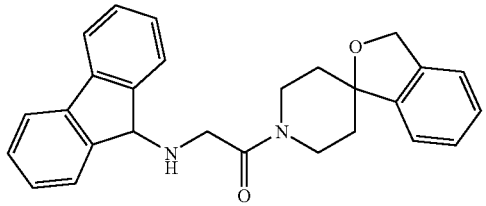

The title compound was prepared in analogy to example 5 using 9H-fluoren-9-amine instead of (RS)-1-(4-chloro-phenyl)-ethylamine. MS: m/z=413 [M+H]+.

Example 8

(RS)-N-[(3-Chlorophenyl)(phenyl)methyl]-2-oxo-2-(1'H,3H-spiro[2-benzofuran-1,4'-piperidin]-1'-yl)ethanamine

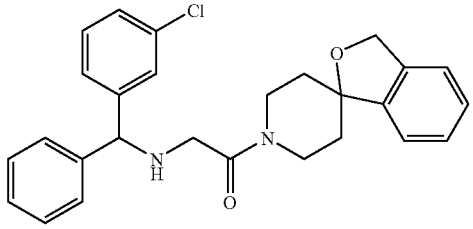

The title compound was prepared in analogy to example 5 using (RS)-C-(3-chloro-phenyl)-C-phenyl-methylamine (intermediate 5) instead of (RS)-1-(4-chloro-phenyl)-ethylamine. MS: m/z=447 [M+H]+.

Example 9

(RS)-N-[(3,4-Dichlorophenyl)(phenyl)methyl]-2-oxo-2-(1'H,3H-spiro[2-benzofuran-1,4'-piperidin]-1'-yl)ethanamine

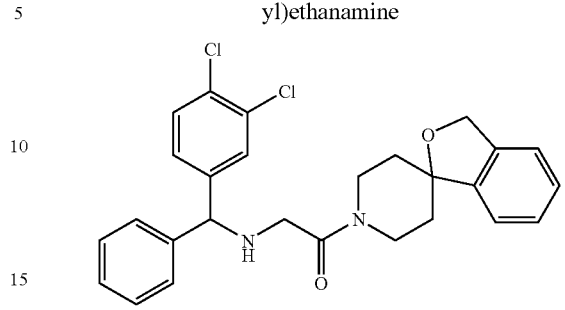

The title compound was prepared in analogy to example 5 using (RS)-C-(3,4-dichloro-phenyl)-C-phenyl-methylamine (intermediate 6) instead of (RS)-1-(4-chloro-phenyl)-ethylamine. MS: m/z=482 [M+H]+.

Example 10

(RS)-N-[(2,4-Dichlorophenyl)(phenyl)methyl]-2-oxo-2-(1'H,3H-spiro[2-benzofuran-1,4'-piperidin]-1'-yl)ethanamine

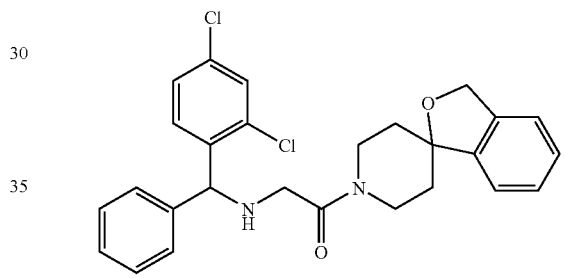

The title compound was prepared in analogy to example 5 using (RS)-C-(2,4-dichloro-phenyl)-C-phenyl-methylamine (intermediate 7) instead of (RS)-1-(4-chloro-phenyl)-ethylamine. MS: m/z=482 [M+H]+.

Example 11

N-[Bis(4-methoxyphenyl)methyl]-2-oxo-2-(1'H,3H-spiro[2-benzofuran-1,4'-piperidin]-1'-yl)ethanamine

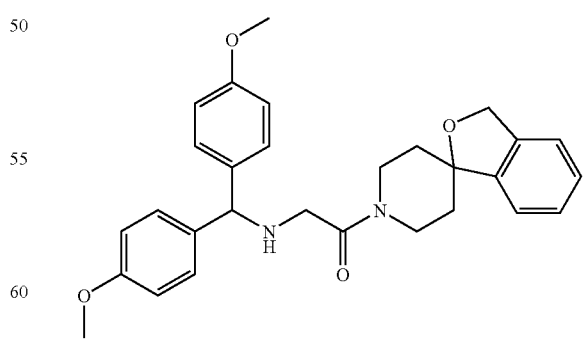

The title compound was prepared in analogy to example 5 using C,C-bis-(4-methoxy-phenyl)-methylamine instead of (RS)-1-(4-chloro-phenyl)-ethylamine. MS: m/z=473 [M+H]+.

Example 12

(RS)-2-Oxo-N-{phenyl[3-(trifluoromethyl)phenyl]methyl}-2-(1'H,3H-spiro[2-benzofuran-1,4'-piperidin]-1'-yl)ethanamine

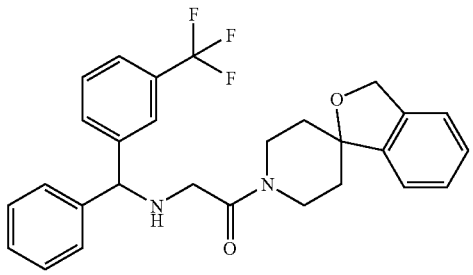

The title compound was prepared in analogy to example 5 using (RS)-C-phenyl-C-(3-trifluoromethyl-phenyl)-methylamine (intermediate 8) instead of (RS)-1-(4-chloro-phenyl)-ethylamine. MS: m/z=481 [M+H]$^+$.

Example 13

(RS)-N-{(4-Fluorophenyl)[3-(trifluoromethyl)phenyl]methyl}-2-oxo-2-(1'H,3H-spiro[2-benzofuran-1,4'-piperidin]-1'-yl)ethanamine

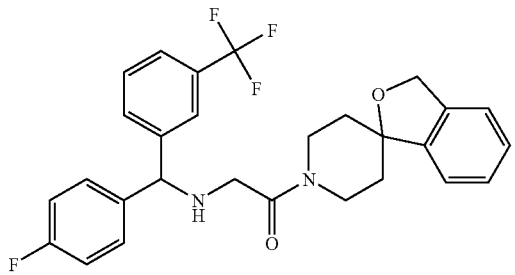

The title compound was prepared in analogy to example 5 using (RS)-C-(4-fluoro-phenyl)-C-(3-trifluoromethyl-phenyl)-methylamine (intermediate 9) instead of (RS)-1-(4-chloro-phenyl)-ethylamine. MS: m/z=499 [M+H]$^+$.

Example 14

(RS)-N-{(4-Methylphenyl)[3-(trifluoromethyl)phenyl]methyl}-2-oxo-2-(1'H,3H-spiro[2-benzofuran-1,4'-piperidin]-1'-yl)ethanamine

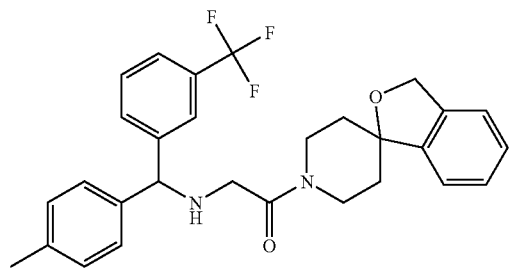

The title compound was prepared in analogy to example 5 using (RS)-C-p-tolyl-C-(3-trifluoromethyl-phenyl)-methylamine (intermediate 10) instead of (RS)-1-(4-chloro-phenyl)-ethylamine. MS: m/z=495 [M+H]$^+$.

Example 15

(RS)-N-{(4-Methoxyphenyl)[3-(trifluoromethyl)phenyl]methyl}-2-oxo-2-(1'H,3H-spiro[2-benzofuran-1,4'-piperidin]-1'-yl)ethanamine

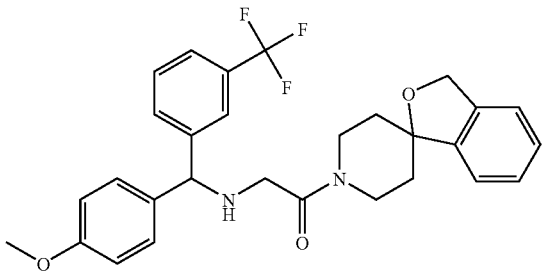

The title compound was prepared in analogy to example 5 using (RS)-C-(4-methoxy-phenyl)-C-(3-trifluoromethyl-phenyl)-methylamine (intermediate 11) instead of (RS)-1-(4-chloro-phenyl)-ethylamine. MS: m/z=511 [M+H]$^+$.

Example 16

4-Chloro-N-ethyl-N-methyl-2-[{[2-oxo-2-(1'H,3H-spiro[2-benzofuran-1,4'-piperidin]-1'-yl)ethyl]amino}(phenyl)methyl]aniline

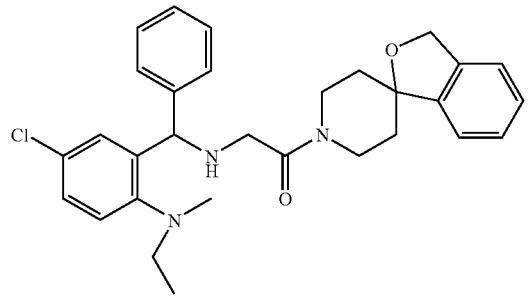

The title compound was prepared in analogy to example 5 using (RS)-[2-(amino-phenyl-methyl)-4-chloro-phenyl]-ethyl-methyl-amine (intermediate 12) instead of (RS)-1-(4-chloro-phenyl)-ethylamine. MS: m/z=505 [M+H]$^+$.

Example 17

(RS)-2-Oxo-N-[phenyl(pyrimidin-2-yl)methyl]-2-(1'H,3H-spiro[2-benzofuran-1,4'-piperidin]-1'-yl)ethanamine

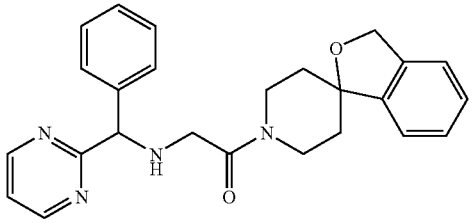

The title compound was prepared in analogy to example 5 using (RS)-C-phenyl-C-pyrimidin-2-yl-methylamine (intermediate 13) instead of (RS)-1-(4-chloro-phenyl)-ethylamine. MS: m/z=415 [M+H]$^+$.

Example 18

(RS)-2-Oxo-N-{phenyl[4-(trifluoromethyl)phenyl]methyl}-2-(1'H,3H-spiro[2-benzofuran-1,4'-piperidin]-1'-yl)ethanamine

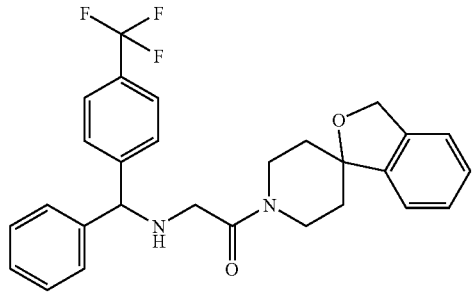

The title compound was prepared in analogy to example 5 using (RS)-C-phenyl-C-(4-trifluoromethyl-phenyl)-methylamine (intermediate 14) instead of (RS)-1-(4-chloro-phenyl)-ethylamine. MS: m/z=481 [M+H]$^+$.

Example 19

(RS)-N-[(4-Chlorophenyl)(4-fluorophenyl)methyl]-2-oxo-2-(1'H,3H-spiro[2-benzofuran-1,4'-piperidin]-1'-yl)ethanamine

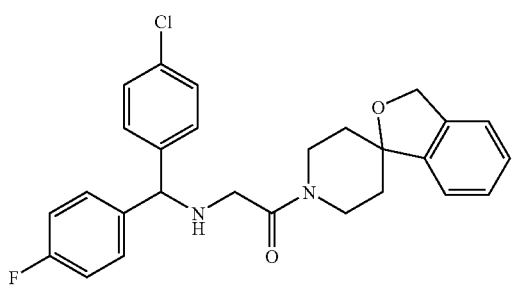

The title compound was prepared in analogy to example 5 using (RS)-C-(4-chloro-phenyl)-C-(4-fluoro-phenyl)-methylamine instead of (RS)-1-(4-chloro-phenyl)-ethylamine. MS: m/z=465 [M+H]$^+$.

Example 20

(RS)-2-Oxo-N-[phenyl(2-thienyl)methyl]-2-(1'H,3H-spiro[2-benzofuran-1,4'-piperidin]-1'-yl)ethanamine

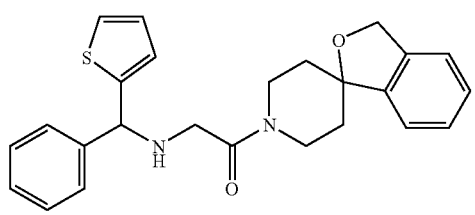

The title compound was prepared in analogy to example 5 using (RS)-C-phenyl-C-thiophen-2-yl-methylamine instead of (RS)-1-(4-chloro-phenyl)-ethylamine. MS: m/z=419 [M+H]$^+$.

Example 21

(RS)-N-[1-(3-Chlorophenyl)ethyl]-2-oxo-2-(1'H,3H-spiro[2-benzofuran-1,4'-piperidin]-1'-yl)ethanamine

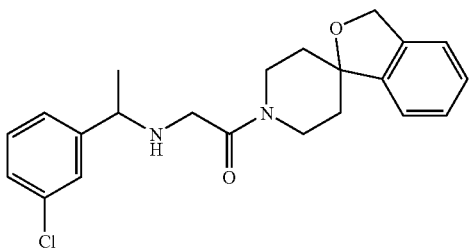

The title compound was prepared in analogy to example 5 using (RS)-1-(3-chloro-phenyl)-ethylamine instead of (RS)-1-(4-chloro-phenyl)-ethylamine. MS: m/z=385 [M+H]$^+$.

Example 22

(RS)-2-Oxo-N-[phenyl(pyridin-4-yl)methyl]-2-(1'H,3H-spiro[2-benzofuran-1,4'-piperidin]-1'-yl)ethanamine

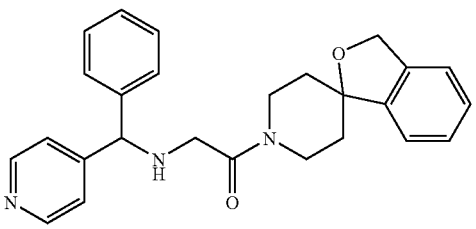

The title compound was prepared in analogy to example 5 using (RS)-C-phenyl-C-pyridin-4-yl-methylamine instead of (RS)-1-(4-chloro-phenyl)-ethylamine. MS: m/z=414 [M+H]$^+$.

Example 23

(RS)-4-Chloro-N-methyl-2-[{[2-oxo-2-(1'H,3H-spiro[2-benzofuran-1,4'-piperidin]-1'-yl)ethyl]amino}(phenyl)methyl]aniline

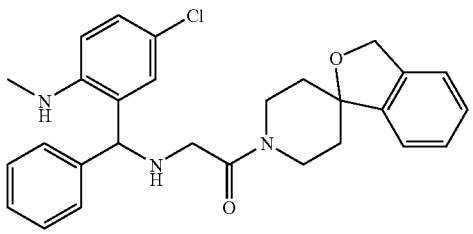

The title compound was prepared in analogy to example 5 using (RS)-[2-(1-amino-2-propenyl-penta-2,4-dienyl)-4-chloro-phenyl]-methyl-amine (intermediate 15) instead of (RS)-1-(4-chloro-phenyl)-ethylamine. MS: m/z=477 [M+H]$^+$.

Example 24

(RS)-N-{[2-Chloro-5-(trifluoromethyl)phenyl](phenyl)methyl}-2-oxo-2-(1'H,3H-spiro[2-benzofuran-1,4'-piperidin]-1'-yl)ethanamine

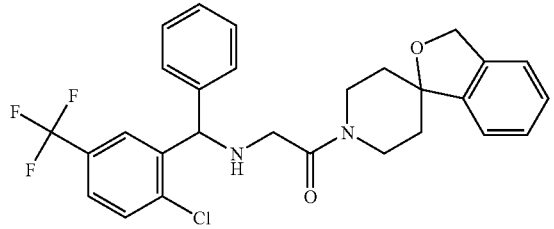

The title compound was prepared in analogy to example 5 using (RS)-[C-(2-chloro-5-trifluoromethyl-phenyl)-C-phenyl-methylamine (intermediate 16) instead of (RS)-1-(4-chloro-phenyl)-ethylamine. MS: m/z=515 [M+H]$^+$.

Example 25

(RS)-N,N-Dimethyl-2-[{[2-oxo-2-(1'H,3H-spiro[2-benzofuran-1,4'-piperidin]-1'-yl)ethyl]amino}(phenyl)methyl]aniline

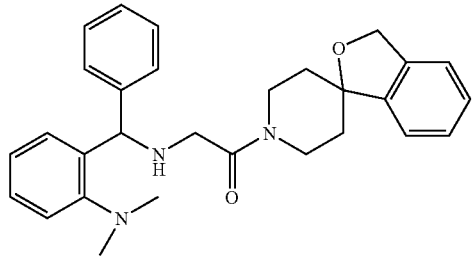

The title compound was prepared in analogy to example 5 using (RS)-[2-(amino-phenyl-methyl)-phenyl]-dimethyl-amine (intermediate 17) instead of (RS)-1-(4-chloro-phenyl)-ethylamine. MS: m/z=456 [M+H]$^+$.

Example 26

(RS)-N-[(4-Chlorophenyl)(pyridin-3-yl)methyl]-2-oxo-2-(1'H,3H-spiro[2-benzofuran-1,4'-piperidin]-1'-yl)ethanamine

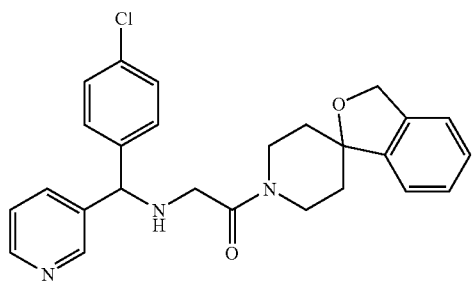

The title compound was prepared in analogy to example 5 using (RS)-C-(4-chloro-phenyl)-C-pyridin-3-yl-methylamine instead of (RS)-1-(4-chloro-phenyl)-ethylamine. MS: m/z=448 [M+H]$^+$.

Example 27

(RS)-2-Oxo-N-[phenyl(pyridin-2-yl)methyl]-2-(1'H,3H-spiro[2-benzofuran-1,4'-piperidin]-1'-yl)ethanamine

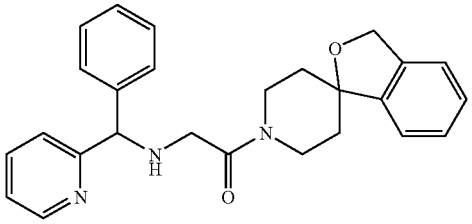

The title compound was prepared in analogy to example 5 using (RS)-C-phenyl-C-pyridin-2-yl-methylamine instead of (RS)-1-(4-chloro-phenyl)-ethylamine. MS: m/z=414 [M+H]$^+$.

Example 28

(RS)-N-{[4-(Difluoromethoxy)phenyl](phenyl)methyl}-2-oxo-2-(1'H,3H-spiro[2-benzofuran-1,4'-piperidin]-1'-yl)ethanamine

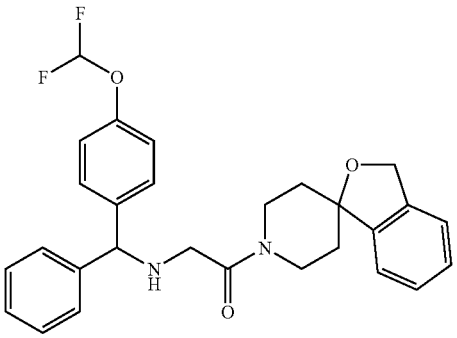

The title compound was prepared in analogy to example 5 using (RS)-C-(4-difluoromethoxy-phenyl)-C-phenyl-methylamine instead of (RS)-1-(4-chloro-phenyl)-ethylamine. MS: m/z=479 [M+H]$^+$.

Example 29

(RS)-N-[(4-Fluorophenyl)(2-thienyl)methyl]-2-oxo-2-(1'H,3H-spiro[2-benzofuran-1,4'-piperidin]-1'-yl)ethanamine

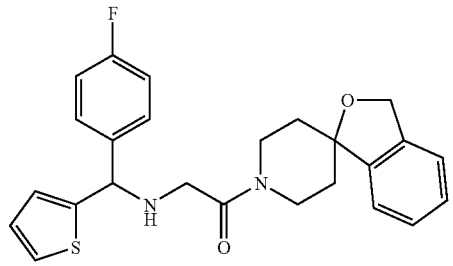

The title compound was prepared in analogy to example 5 using (RS)-C-(4-fluoro-phenyl)-C-thiophen-2-yl-methylamine instead of (RS)-1-(4-chloro-phenyl)-ethylamine. MS: m/z=437 [M+H]$^+$.

Example 30

(RS)-N-[(3,5-Dimethyl-1H-pyrazol-4-yl)(phenyl)methyl]-2-oxo-2-(1'H,3H-spiro[2-benzofuran-1,4'-piperidin]-1'-yl)ethanamine

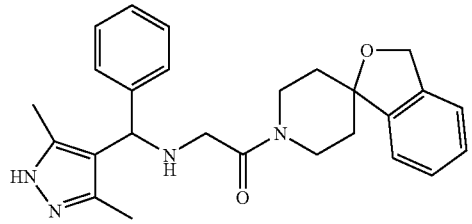

The title compound was prepared in analogy to example 5 using (RS)-C-(3,5-dimethyl-1H-pyrazol-4-yl)-C-phenyl-methylamine instead of (RS)-1-(4-chloro-phenyl)-ethylamine. MS: m/z=431 [M+H]$^+$.

Example 31

(2R)-N-(4-Chlorophenyl)-2-{[2-oxo-2-(1'H,3H-spiro[2-benzofuran-1,4-piperidin]-1'-yl)ethyl]amino}-2-phenylacetamide

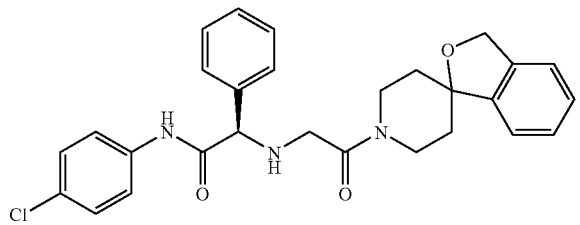

The title compound was prepared in analogy to example 5 using (2R)-2-amino-N-(4-chloro-phenyl)-2-phenyl-acetamide (intermediate 18) instead of (RS)-1-(4-chloro-phenyl)-ethylamine. MS: m/z=491 [M+H]$^+$.

Example 32

(RS)-Benzyl 3-{[2-oxo-2-(140 H,3H-spiro[2-benzofuran-1,4'-piperidin]-1'-yl)ethyl]amino}-3-phenyl-propanoate

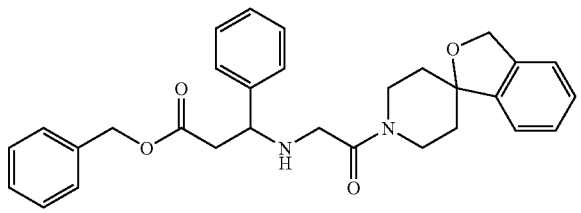

The title compound was prepared in analogy to example 5 using (RS)-3-amino-3-phenyl-propionic acid benzyl ester (intermediate 19) instead of (RS)-1-(4-chloro-phenyl)-ethylamine. MS: m/z=485 [M+H]$^+$.

Example 33

(RS)-Ethyl 3-{[2-oxo-2-(1'H,3H-spiro[2-benzofuran-1,4'-piperidin]-1'-yl)ethyl]amino}-3-phenylpropanoate

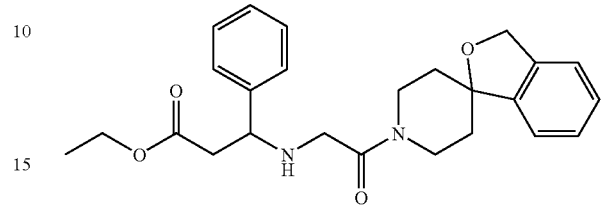

The title compound was prepared in analogy to example 5 using (RS)-3-amino-3-phenyl-propionic acid ethyl ester instead of (RS)-1-(4-chloro-phenyl)-ethylamine. MS: m/z=423 [M+H]$^+$.

Example 34

(RS)-N-[(3-Methylphenyl)(phenyl)methyl]-2-oxo-2-(1'H,3H-spiro[2-benzofuran-1,4'-piperidin]-1'-yl)ethanamine

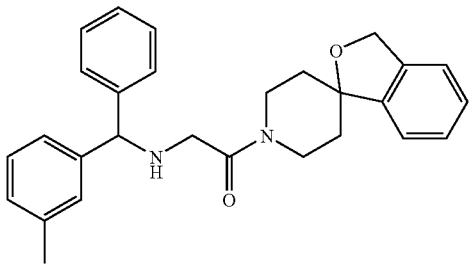

The title compound was prepared in analogy to example 5 using (RS)-C-phenyl-C-m-tolyl-methylamine (intermediate 20) instead of (RS)-1-(4-chloro-phenyl)-ethylamine. MS: m/z=427 [M+H]$^+$.

Example 35

(RS)-N-[(4-Methoxyphenyl)(phenyl)methyl]-2-oxo-2-(1'H,3H-spiro [2-benzofuran-1,4'-piperidin]-1'-yl)ethanamine

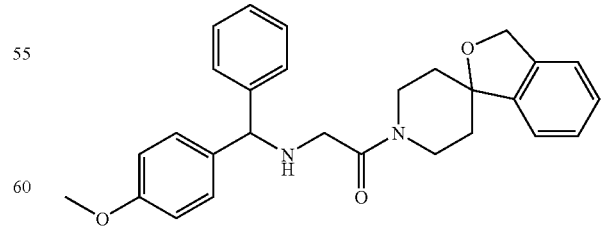

The title compound was prepared in analogy to example 5 using (RS)-C-(4-methoxy-phenyl)-C-phenyl-methylamine instead of (RS)-1-(4-chloro-phenyl)-ethylamine. MS: m/z=443 [M+H]$^+$.

Example 36

(RS)-N-[(4-Chlorophenyl)(pyridin-4-yl)methyl]-2-oxo-2-(1'H,3H-spiro[2-benzofuran-1,4'-piperidin]-1'-yl)ethanamine

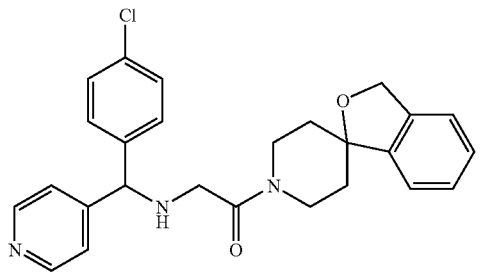

The title compound was prepared in analogy to example 5 using (RS)-C-(4-chloro-phenyl)-C-pyridin-4-yl-methylamine instead of (RS)-1-(4-chloro-phenyl)-ethylamine. MS: m/z=448 [M+H]$^+$.

Example 37

(RS)-4-Chloro-2-[{[2-oxo-2-(1'H,3H-spiro[2-benzofuran-1,4'-piperidin]-1'yl)ethyl]amino}(phenyl)methyl]phenol

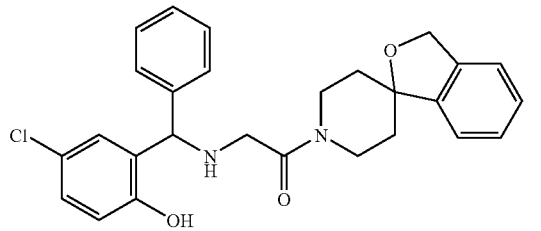

The title compound was prepared in analogy to example 5 using (RS)-2-(amino-phenyl-methyl)-4-chloro-phenol (intermediate 21) instead of (RS)-1-(4-chloro-phenyl)-ethylamine. MS: m/z=463 [M+H]$^+$.

Example 38

(RS)-Ethyl N-{4-chloro-2-[{[2-oxo-2-(1'H,3H-spiro[2-benzofuran-1,4'-piperidin]-1'-yl)ethyl]amino}(phenyl)methyl]phenyl}glycinate

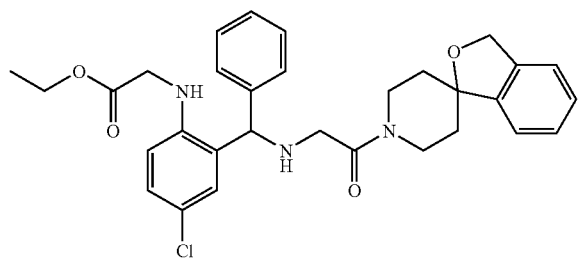

The title compound was prepared in analogy to example 5 using (RS)-[2-(amino-phenyl-methyl)-4-chloro-phenylamino]-acetic acid ethyl ester (intermediate 22) instead of (RS)-1-(4-chloro-phenyl)-ethylamine. MS: m/z=549 [M+H]$^+$.

Example 39

(RS)-4-Chloro-2-[{[2-oxo-2-(1'H,3H-spiro[2-benzofuran-1,4'-piperidin]-1'-yl)ethyl]amino}(phenyl)methyl]aniline

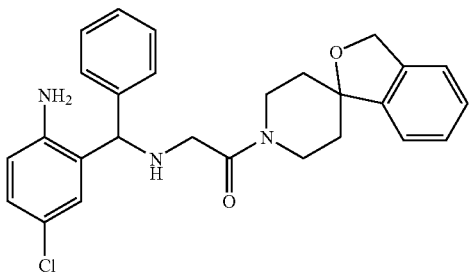

The title compound was prepared in analogy to example 5 using (RS)-2-(amino-phenyl-methyl)-4-chloro-phenylamine (intermediate 23) instead of (RS)-1-(4-chloro-phenyl)-ethylamine. MS: m/z=462 [M+H]$^+$.

Example 40

(RS)-4-Methyl-N-{2-[{[2-oxo-2-(1'H,3H-spiro[2-benzofuran-1,4'-piperidin]-1'-yl)ethyl]amino}(phenyl)methyl]phenyl}benzenesulfonamide

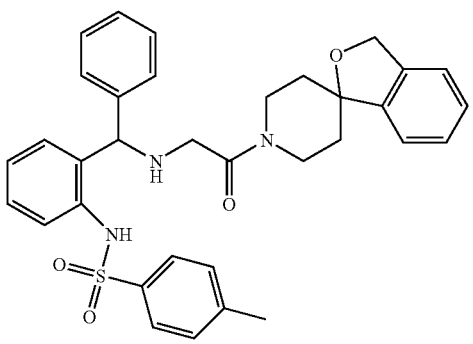

The title compound was prepared in analogy to example 5 using (RS)-hepta-2,4-diene-3-sulfonic acid [2-(amino-phenyl-methyl)-phenyl]-amide (intermediate 24) instead of (RS)-1-(4-chloro-phenyl)-ethylamine. MS: m/z=582 [M+H]$^+$.

Example 41

(RS)-2-[(2-Amino-5-chlorophenyl){[2-oxo-2-(1'H,3H-spiro[2-benzofuran-1,4'-piperidin]-1'-yl)ethyl]amino}methyl]phenol

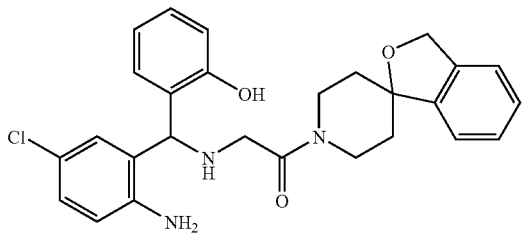

The title compound was prepared in analogy to example 5 using (RS)-2-[amino-(2-amino-5-chloro-phenyl)-methyl]-phenol (intermediate 25) instead of (RS)-1-(4-chloro-phenyl)-ethylamine. MS: m/z=478 [M+H]$^+$.

Example 42

(RS)-N-{[2-(1H-Imidazol-2-yl)phenyl](phenyl)methyl}-2-oxo-2-(1'H,3H-spiro[2-benzofuran-1,4'-piperidin]-1'-yl)ethanamine

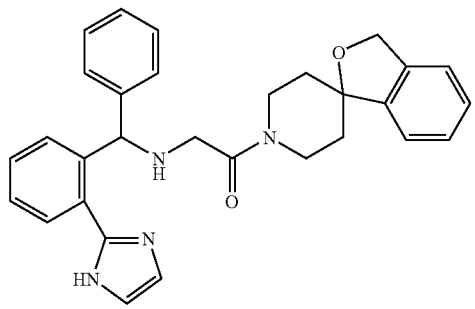

The title compound was prepared in analogy to example 5 using (RS)-C-[2-(1H-imidazol-2-yl)-phenyl]-C-phenyl-methylamine (intermediate 26) instead of (RS)-1-(4-chloro-phenyl)-ethylamine. MS: m/z=479 [M+H]$^+$.

Example 43

(RS)-N-[4-Chloro-2-(hydroxymethyl)phenyl]-2-{[2-oxo-2-(1'H,3H-spiro[2-benzofuran-1,4'-piperidin]-1'-yl)ethyl]amino}-2-phenylacetamide

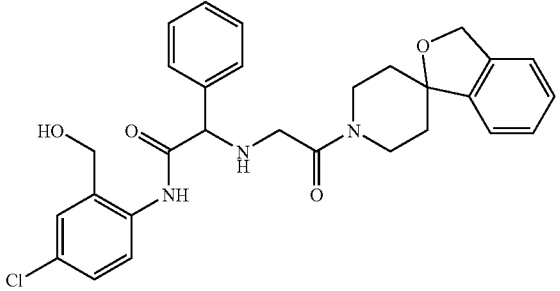

The title compound was prepared in analogy to example 5 using (RS)-2-amino-N-(4-chloro-2-hydroxymethyl-phenyl)-2-phenyl-acetamide (intermediate 27) instead of (RS)-1-(4-chloro-phenyl)-ethylamine. MS: m/z=521 [M+H]$^+$.

Example 44

(RS)-N-[4-Chloro-2-(hydroxymethyl)phenyl]-2-{[2-oxo-2-(1'H,3H-spiro[2-benzofuran-1,4'-piperidin]-1'-yl)ethyl]amino}-2-phenylacetamide

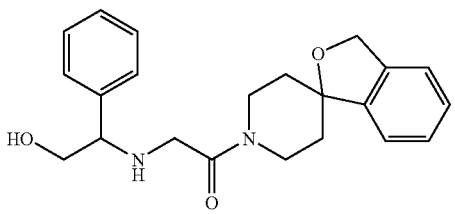

The title compound was prepared in analogy to example 5 using (RS)-2-amino-2-phenyl-ethanol instead of (RS)-1-(4-chloro-phenyl)-ethylamine. MS: m/z=367 [M+H]$^+$.

Example 45

(RS)-N-[(4-Chlorophenyl)(1-methyl-1H-imidazol-2-yl)methyl]-2-oxo-2-(1'H,3H-spiro[2-benzofuran-1,4'-piperidin]-1'-yl)ethanamine

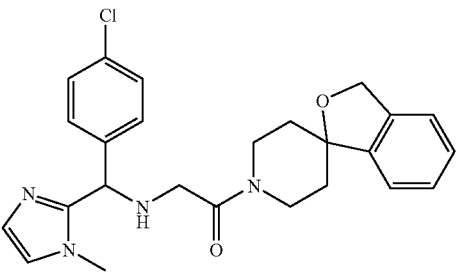

The title compound was prepared in analogy to example 5 using (RS)-C-(4-chloro-phenyl)-C-(1-methyl-1H-imidazol-2-yl)-methylamine instead of (RS)-1-(4-chloro-phenyl)-ethylamine. MS: m/z=451 [M+H]$^+$.

Example 46

(1S,2R)-2-(4-Chlorophenyl)-1-(4-morpholin-4-ylphenyl)-2-{[2-oxo-2-(1'H,3H-spiro[2-benzofuran-1,4'-piperidin]-1'-yl)ethyl]amino}ethanol

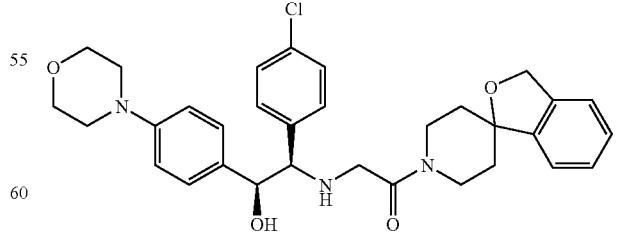

The title compound was prepared in analogy to example 5 using (1S,2R)-2-amino-2-(4-chloro-phenyl)-1-(4-morpholin-4-yl-phenyl)-ethanol (intermediate 28) instead of (RS)-1-(4-chloro-phenyl)-ethylamine. MS: m/z=563 [M+H]$^+$.

Example 47

(1S,2R)-1-(2-Chlorophenyl)-2-(4-chlorophenyl)-2-{[2-oxo-2-(1'H,3H-spiro[2-benzofuran-1,4'-piperidin]-1'-yl)ethyl]amino}ethanol

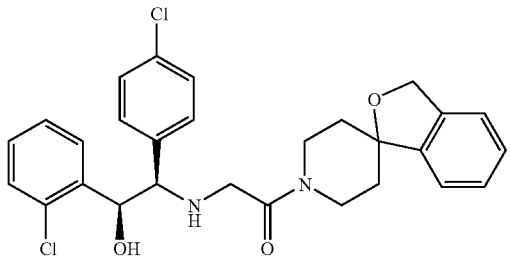

The title compound was prepared in analogy to example 5 using (1S,2R)-2-amino-2-(4-chloro-phenyl)-1-(2-chloro-phenyl)-ethanol (intermediate 29) instead of (RS)-1-(4-chloro-phenyl)-ethylamine. MS: m/z=512 [M+H]$^+$.

Example 48

(RS)-4-(4-Chlorophenyl)-4-[{2-oxo-2-(1'H,3H-spiro[2-benzofuran-1,4'-piperidin]-1'-yl)ethyl]amino}butanoic acid

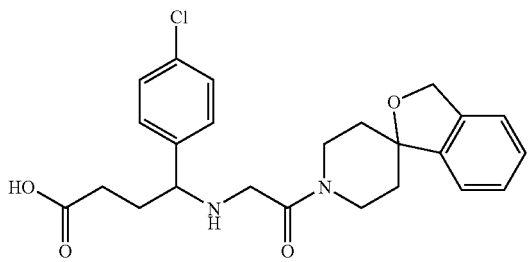

The title compound was prepared in analogy to example 5 using (RS)-4-amino-4-(4-chloro-phenyl)-butyric acid (intermediate 30) instead of (RS)-1-(4-chloro-phenyl)-ethylamine. MS: m/z=443 [M+H]$^+$.

Example 49

(1RS,2RS)-1-(4-Chlorophenyl)-1-{[2-oxo-2-(1'H,3H-spiro[2-benzofuran-1,4'-piperidin]-1'-yl)ethyl]amino}-2-pyridin-2-yl-propan-2-ol

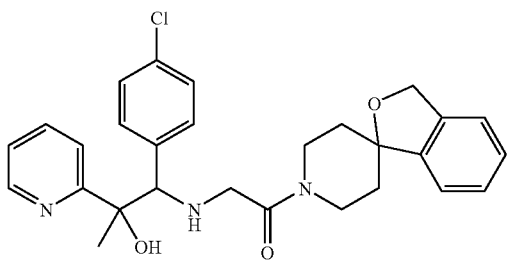

The title compound was prepared in analogy to example 5 using (1RS,2RS)-1-amino-1-(4-chloro-phenyl)-2-pyridin-2-yl-propan-2-ol (intermediate 31) instead of (RS)-1-(4-chloro-phenyl)-ethylamine. MS: m/z=493 [M+H]$^+$.

Example 50

(1RS,2RS)-1-(4-Chlorophenyl)-1-{[2-oxo-2-(1'H,3H-spiro[2-benzofuran-1,4'-piperidin]-1'-yl)ethyl]amino}-2-pyridin-3-yl-propan-2-ol

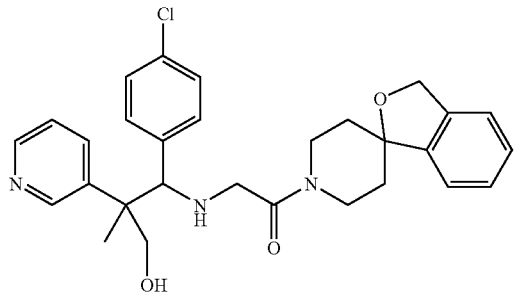

The title compound was prepared in analogy to example 5 using (2RS,3RS)-3-amino-3-(4-chloro-phenyl)-2-methyl-2-pyridin-3-yl-propan-1-ol (intermediate 32) instead of (RS)-1-(4-chloro-phenyl)-ethylamine. MS: m/z=507 [M+H]$^+$.

Example 51

1-(4-Chlorophenyl)-1-{[2-oxo-2-(1'H,3H-spiro[2-benzofuran-1,4'-piperidin]-1'-yl)ethyl]amino}-2-pyridin-3-yl-propan-2-ol

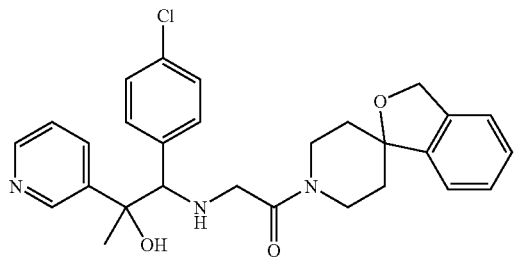

The title compound was prepared in analogy to example 5 using and (1RS,2RS)-1-amino-1-(4-chloro-phenyl)-2-phenyl-propan-2-ol (intermediate 33) instead of (RS)-1-(4-chloro-phenyl)-ethylamine. MS: m/z=492 [M+H]$^+$.

Example 52

1-(4-Chlorophenyl)-1-{[2-oxo-2-(1'H,3H-spiro[2-benzofuran-1,4'-piperidin]-1'-yl)ethyl]amino}-2-pyridin-4-ylpropan-2-ol

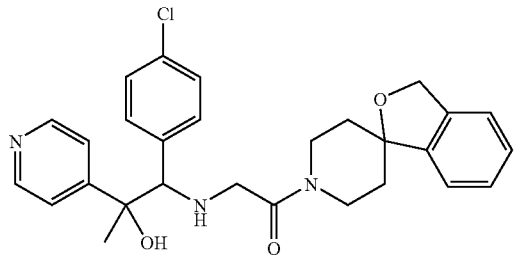

The title compound was prepared in analogy to example 5 using and (1RS,2RS)-1-amino-1-(4-chloro-phenyl)-2-pyridin-4-yl-propan-2-ol (intermediate 34) instead of (RS)-1-(4-chloro-phenyl)-ethylamine. MS: m/z=493 [M+H]⁺.

Example 53

(1RS,2R)-N-{(4-Chlorophenyl)[4-(trifluoromethoxy)phenyl]methyl}-1-oxo-1-(1'H,3H-spiro[2-benzofuran-1,4'-piperidin]-1'-yl)propan-2-amine

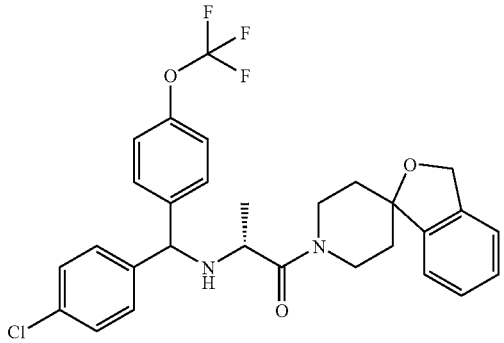

(2R)-1-Oxo-1-(1'H,3H-spiro[2-benzofuran-1,4'-piperidin]-1'-yl)propan-2-amine (obtained from the corresponding trifluoroacetate by extraction with DCM and 1 N NaOH) (0.1 g, 0.38 mmol) and 4-(trifluoromethoxy)-4'-chlorobenzophenone (0.122 g, 0.38 mmol) were dissolved in toluene (10 mL), tetraisopropyl orthotitanate (0.24 mL, 0.76 mmol) was added and the reaction mixture was refluxed for 18 h. After evaporation the residue was dissolved in EtOH (10 mL) and treated with sodium cyanoborhydride (0.031 g, 0.46 mmol) at 20° C. for 1 h. EtOH was evaporated and the residue was stirred with DCM (20 mL), water (10 mL) and 3N NaOH (3 mL). The resulting suspension was filtered, the layers were separated, the aqueous layer was extracted with DCM (20 mL) and the organic layer was washed with 3N NaOH (10 mL). The combined organic layers were dried and evaporated to give a yellow oil, which was purified by chromatography on silica gel in heptane/AcOEt 2:1 affording a white foam (60 mg, 27%). MS: m/z=545 [M+H]⁺.

Example 54

(RS,2R)-N-[1-Benzofuran-2-yl(4-chlorophenyl)methyl]-1-oxo-1-(1'H,3H-spiro[2-benzofuran-1,4'-piperidin]-1'-yl)propan-2-amine

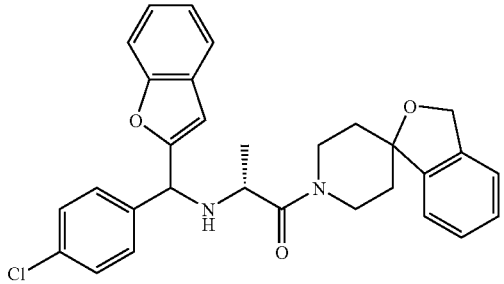

The title compound was prepared in analogy to example 53 using 4-(chlorobenzoyl)benzofuran instead of 4-(trifluoromethoxy)-4'-chlorobenzophenone. MS: m/z=502 [M+H]⁺.

Example 55

(RS)-N-[(2-Chlorophenyl)(4-chlorophenyl)methyl]-2-oxo-2-(1'H,3H-spiro[2-benzofuran-1,4'-piperidin]-1'-yl)ethanamine

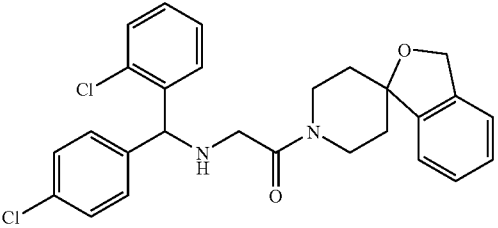

2-Oxo-2-(1'H,3H-spiro[2-benzofuran-1,4'-piperidin]-1'-yl)ethanamine (50 mg, 0.203 mmol) and (4-chloro-phenyl)-(2-chloro-phenyl)-methanone (51 mg, 0.203 mmol) were dissolved in toluene (1 mL). Tetraisopropyl orthotitanate (0.12 mL, 0.406 mmol) was added and the mixture was heated in a sealed tube in a microwave oven at 140° C. for 15 min. After cooling, ethanol (1 mL) and sodium cyanoborohydride (15 mg) were added and the reduction was allowed to proceed at 20° C. over night. Next day, water (0.2 mL) was added and shaking was continued for 24 h to precipitate the titanium oxides. The suspension was filtered through dicalite and the solid rinsed with EtOH (5 mL). The filtrate was recuperated and evaporated to dryness. The residue was dissolved in DMSO (1 mL) and then directly purified by preparative HPLC on a YMC-AQ column with a gradient of acetonitrile acid (30-95% in 15 min.) in aqueous 0.05% formic. The fractions with the correct mass were collected and evaporated to dryness to afford the title compound. MS: m/z=482 [M+H]⁺.

Example 56

(RS)-N-[(3,4-Dichlorophenyl)(pyridin-2-yl)methyl]-2-oxo-2-(1'H,3H-spiro[2-benzofuran-1,4'-piperidin]-1'-yl)ethanamine

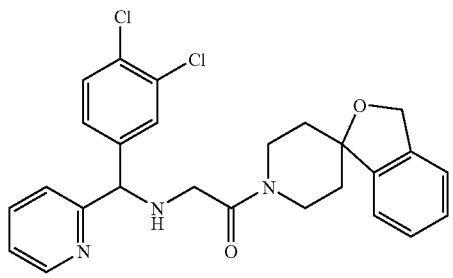

The title compound was prepared in analogy to example 55 using (3,4-dichloro-phenyl)-pyridin-2-yl-methanone instead of (4-chloro-phenyl)-(2-chloro-phenyl)-methanone. MS: m/z=483 [M+H]⁺.

Example 57

(RS)-N-[(3-chlorophenyl)(pyridin-2-yl)methyl]-2-oxo-2-(1'H,3H-spiro[2-benzofuran-1,4'-piperidin]-1'-yl)ethanamine

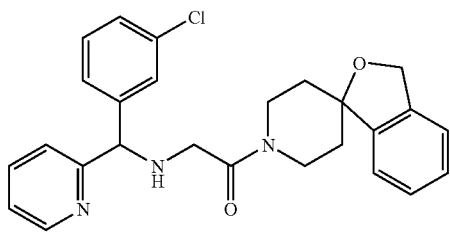

The title compound was prepared in analogy to example 55 using (3-chloro-phenyl)-pyridin-2-yl-methanone instead of (4-chloro-phenyl)-(2-chloro-phenyl)-methanone. MS: m/z=448 [M+H]$^+$.

Example 58

(RS)-N-[(4-Chlorophenyl)(1,3-thiazol-2-yl)methyl]-2-oxo-2-(1'H,3H-spiro[2-benzofuran-1,4'-piperidin]-1'-yl)ethanamine

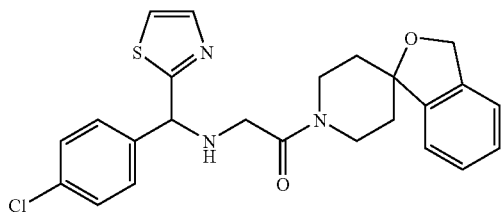

The title compound was prepared in analogy to example 55 using (4-chloro-phenyl)-thiazol-2-yl-methanone instead of (4-chloro-phenyl)-(2-chloro-phenyl)-methanone. MS: m/z=454 [M+H]$^+$.

Example 59

(RS)-N-[(3-Chlorophenyl)(1,3-thiazol-2-yl)methyl]-2-oxo-2-(1'H,3H-spiro[2-benzofuran-1,4'-piperidin]-1'-yl)ethanamine

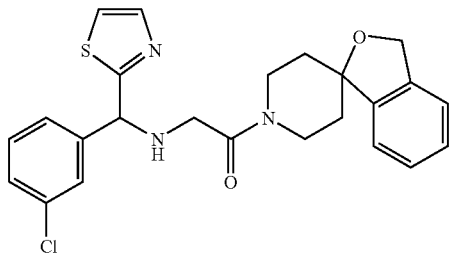

The title compound was prepared in analogy to example 55 using (3-chloro-phenyl)-thiazol-2-yl-methanone instead of (4-chloro-phenyl)-(2-chloro-phenyl)-methanone. MS: m/z=454 [M+H]$^+$.

Example 60

(RS)-N-[(3,4-Dichlorophenyl)(1,3-thiazol-2-yl)methyl]-2-oxo-2-(1'H,3H-spiro[2-benzofuran-1,4'-piperidin]-1'-yl)ethanamine

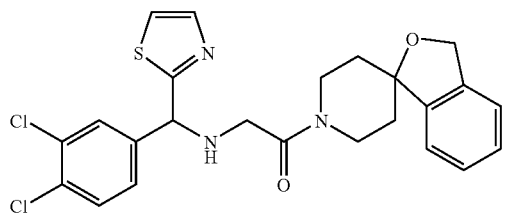

The title compound was prepared in analogy to example 55 using (3,4-dichloro-phenyl)-thiazol-2-yl-methanone instead of (4-chloro-phenyl)-(2-chloro-phenyl)-methanone. MS: m/z=489 [M+H]$^+$.

Example 61

N-[Bis(3-chlorophenyl)methyl]-2-oxo-2-(1'H,3H-spiro[2-benzofuran-1,4'-piperidin]-1'-yl)ethanamine

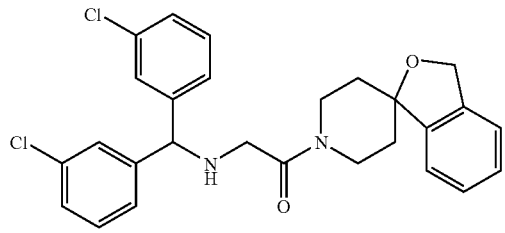

The title compound was prepared in analogy to example 55 using bis-(3-chloro-phenyl)-methanone instead of (4-chloro-phenyl)-(2-chloro-phenyl)-methanone. MS: m/z=482 [M+H]+.

Example 62

(RS)-N-[(4-Chlorophenyl){3-[(4-methylpiperazin-1-yl)methyl]phenyl}methyl]-2-oxo-2-(1'H,3H-spiro[2-benzofuran-1,4'-piperidin]-1'-yl)ethanamine

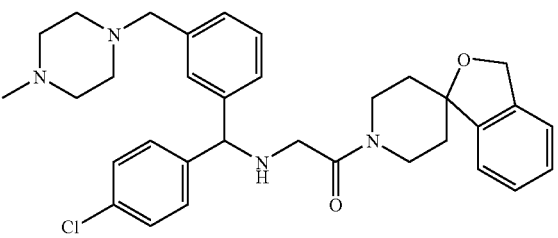

The title compound was prepared in analogy to example 55 using (4-chloro-phenyl)-[3-(4-methyl-piperazin-1-ylmethyl)-phenyl]-methanone instead of (4-chloro-phenyl)-(2-chloro-phenyl)-methanone. MS: m/z=560 [M+H]$^+$.

Example 63

(RS)-N-[(3-Chlorophenyl){2-[(4-methylpiperazin-1-yl)methyl]phenyl}methyl]-2-oxo-2-(1'H,3H-spiro[2-benzofuran-1,4'-piperidin]-1'-yl)ethanamine

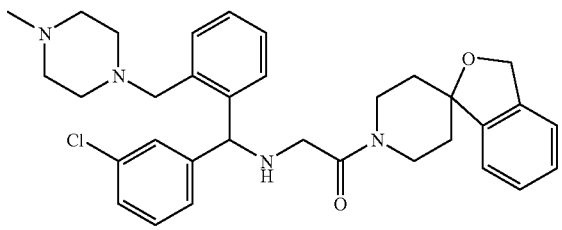

The title compound was prepared in analogy to example 55 using (3-chloro-phenyl)-[2-(4-methyl-piperazin-1-ylmethyl)-phenyl]-methanone instead of (4-chloro-phenyl)-(2-chloro-phenyl)-methanone. MS: m/z=560 [M+H]⁺.

Example 64

(RS)-N-[(4-Chlorophenyl)(pyridin-2-yl)methyl]-2-oxo-2-(1'H,3H-spiro[2-benzofuran-1,4'-piperidin]-1'-yl)ethanamine

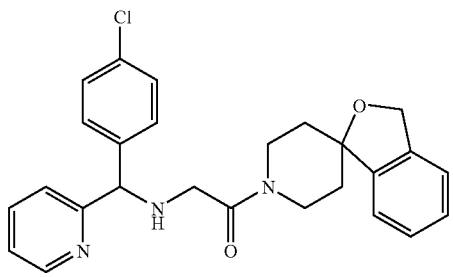

The title compound was prepared in analogy to example 55 using (4-chloro-phenyl)-pyridin-2-yl-methanone instead of (4-chloro-phenyl)-(2-chloro-phenyl)-methanone. MS: m/z=448 [M+H]⁺.

Example 65

(RS)-N-[(3-Chlorophenyl){3-[(4-methylpiperazin-1-yl)methyl]phenyl}methyl]-2-oxo-2-(1'H,3H-spiro[2-benzofuran-1,4'-piperidin]-1'-yl)ethanamine

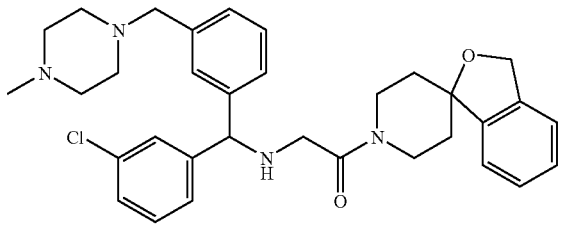

The title compound was prepared in analogy to example 55 using (3-chloro-phenyl)-[3-(4-methyl-piperazin-1-ylmethyl)-phenyl]-methanone instead of (4-chloro-phenyl)-(2-chloro-phenyl)-methanone. MS: m/z=560 [M+H]⁺.

Example 66

(RS)-N-[(3,4-Dichlorophenyl){3-[(4-methylpiperazin-1-yl)methyl]phenyl}methyl]-2-oxo-2-(1'H,3H-spiro[2-benzofuran-1,4'-piperidin]-1'-yl)ethanamine

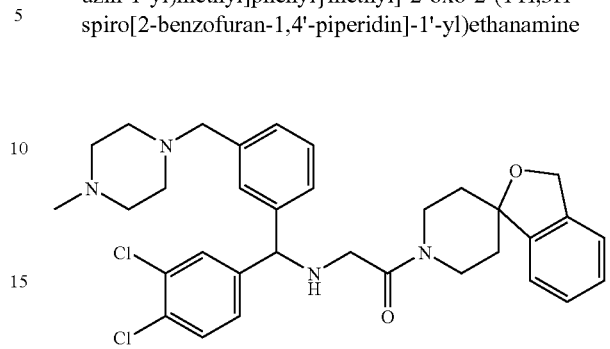

The title compound was prepared in analogy to example 55 using (3,4-dichloro-phenyl)-[3-(4-methyl-piperazin-1-ylmethyl)-phenyl]-methanone instead of (4-chloro-phenyl)-(2-chloro-phenyl)-methanone. MS: m/z=594 [M+H]⁺.

Example 67

(RS)-N-[(4-Chlorophenyl)(1,3-oxazol-2-yl)methyl]-2-oxo-2-(1'H,3H-spiro[2-benzofuran-1,4'-piperidin]-1'-yl)ethanamine

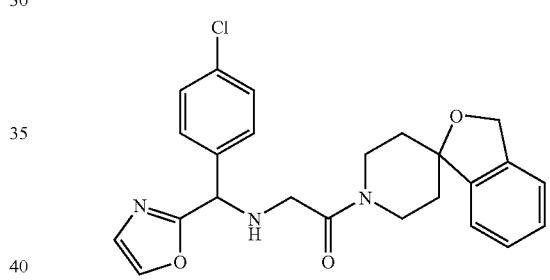

The title compound was prepared in analogy to example 55 using (4-chloro-phenyl)-oxazol-2-yl-methanone instead of (4-chloro-phenyl)-(2-chloro-phenyl)-methanone. MS: m/z=438 [M+H]⁺.

Example 68

(RS)-N-[(3-Chlorophenyl)(1,3-oxazol-2-yl)methyl]-2-oxo-2-(1'H,3H-spiro[2-benzofuran-1,4'-piperidin]-1'-yl)ethanamine

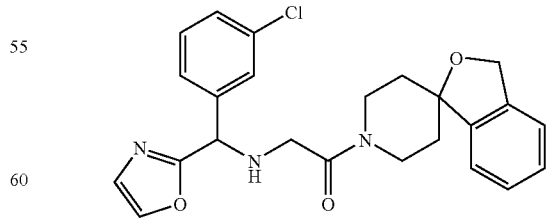

The title compound was prepared in analogy to example 55 using (3-chloro-phenyl)-oxazol-2-yl-methanone instead of (4-chloro-phenyl)-(2-chloro-phenyl)-methanone. MS: m/z=438 [M+H]⁺.

Example 69

(2R)-N-(Diphenylmethyl)-1-oxo-1-(1'H,3H-spiro[2-benzofuran-1,4'-piperidin]-1'-yl)propan-2-amine

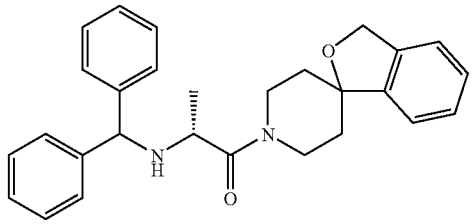

(2R)-1-oxo-1-(1'H,3H-spiro[2-benzofuran-1,4'-piperidin]-1'-yl)propan-2-amine trifluoroacetate (0.1 g, 0.26 mmol) dissolved in MeCN (3 mL), bromodiphenylmethane (0.066 g, 0.26 mmol) and cesium carbonate (169 mg, 0.52 mmol) added and stirred at reflux over night. Filtration, evaporation and chromatography on silica gel with heptane/AcOEt 2:1 gave a white foam (30 mg, 26%). MS: m/z=427 [M+H]$^+$.

Example 70

N-(Diphenylmethyl)-2-methyl-1-oxo-1-(1'H,3H-spiro[2-benzofuran-1,4'-piperidin]-1'-yl)propan-2-amine

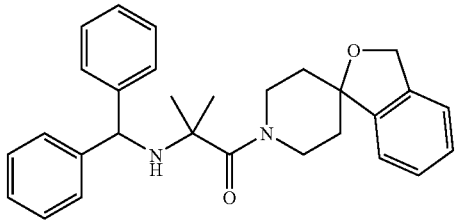

2-Methyl-1-oxo-1-(1'H,3H-spiro[2-benzofuran-1,4'-piperidin]-1'-yl)propan-2-amine (100 mg, 0.36 mmol), bromodiphenylmethane (99 mg, 0.4 mmol), and N-ethyldiisopropylamine (0.069 mL, 0.4 mmol) in NMP (1 mL) were heated in a microwave oven at 200° C. for 10 min. NMP was distilled off at 100° C./0.5 mbar. The residue was extracted with heptane, 1 N NaOH. Chromatography: heptane/AcOEt 4:1. One obtained 68 mg (42%) white foam. MS: m/z=441 [M+H]$^+$.

Example 71

1-[(2R)-2-{[2-Oxo-2-(1'H,3H-spiro[2-benzofuran-1,4'-piperidin]-1'-yl)ethyl]amino}-2-phenylacetyl]azetidin-3-ol

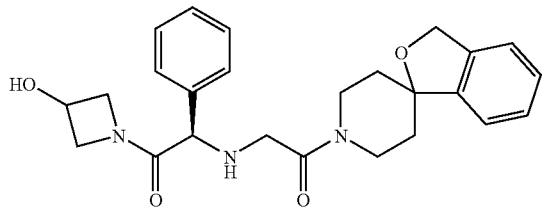

(2R)-{[(Allyloxy)carbonyl][2-oxo-2-(1'H,3H-spiro[2-benzofuran-1,4'-piperidin]-1'-yl)ethyl]amino}(phenyl)acetic acid (40 mg, 0.086 mmol), azetin-3-ol (6 mg, 0.086 mmol), and O-(7-azabenzotriazol-1-yl)-N,N,N',N'-tetramethyluronium hexafluorophosphate (HATU) (49 mg, 0.13 mmol) were suspended in screw-capped vials in DCM (2 mL) and treated with triethylamine (0.04 mL, 0.3 mmol) for 5 h at 20° C. Pyrrolidine (0.07 mL, 0.86 mmol) and a solution of tetrakis (triphenylphosphine)palladium (1 mg, 0.001 mmol) in DCM (0.2 mL) were added and shaking at 20° C. was continued for 14 h. DCM was evaporated, the residue was dissolved in DMF (0.8 mL), diluted with water (0.1 mL) and then directly purified by preparative HPLC on a Zorbax XDB column with a gradient of MeCN/water 10-90%. One obtained 8 mg (21%) of colorless oil. MS: m/z=436 [M+H]$^+$.

Example 72

(2R)-N-(5-Chloropyridin-2-yl)-2-{[2-oxo-2-(1'H,3H-spiro[2-benzofuran-1,4'-piperidin]-1'-yl)ethyl]amino}-2-phenylacetamide

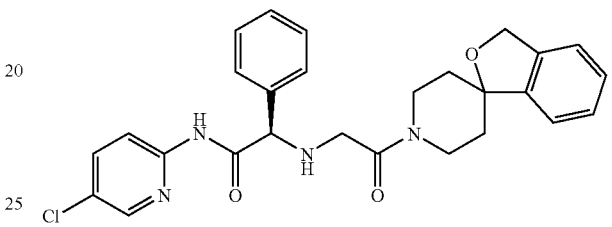

The title compound was prepared in analogy to example 71 using 2-amino-5-chloropyridine instead of azetin-3-ol. MS: m/z=491 [M+H]$^+$.

Example 73

(1R)-2-Oxo-N-[2-oxo-2-(1'H,3H-spiro[2-benzofuran-1,4'-piperidin]-1'-yl)ethyl]-1-phenyl-2-pyrrolidin-1-ylethanamine

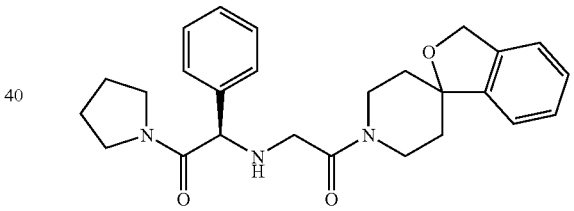

The title compound was prepared in analogy to example 71 using pyrrolidine instead of azetin-3-ol. MS: m/z=434 [M+H]$^+$.

Example 74

{(2R)-1-[(2R)-2-{[2-Oxo-2-(1'H,3H-spiro[2-bezofuran-1,4'-piperidin]-1'-yl)ethyl]amino}-2-phenylacetyl]pyrrolidin-2-yl}methanol

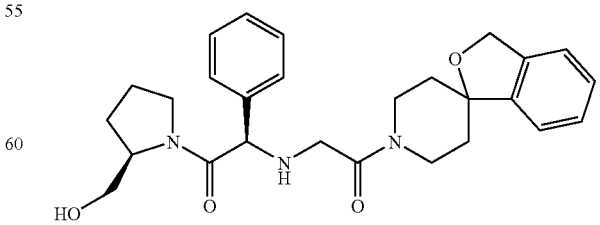

The title compound was prepared in analogy to example 71 using (S)-(+)-2-(hydroxymethyl)pyrrolidine instead of azetin-3-ol. MS: m/z=464 [M+H]$^+$.

Example 75

1-[(2R)-2-[{2-Oxo-2-(1'H,3H-spiro[2-benzofuran-1,4'-piperidin]-1'-yl)ethyl]amino}-2-phenylacetyl]pyrrolidin-3-ol

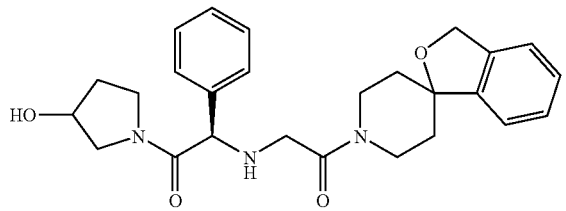

The title compound was prepared in analogy to example 71 using 3-pyrrolidinol instead of azetin-3-ol. MS: m/z=450 [M+H]+.

Example 76

N,N-Dimethyl-1-[(2R)-2-{[2-oxo-2-(1'H,3H-spiro[2-benzofuran-1,4'-piperidin]-1'-yl)ethyl]amino}-2-phenylacetyl]pyrrolidin-3-amine

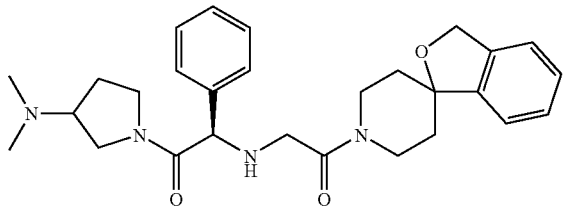

The title compound was prepared in analogy to example 71 using 3-(dimethylamino)pyrrolidine instead of azetin-3-ol. MS: m/z=477 [M+H]+.

Example 77

(1R)-2-Morpholin-4-yl-2-oxo-N-[2-oxo-2-(1'H,3H-spiro[2-benzofuran-1,4'-piperidin]-1'-yl)ethyl]-1-phenylethanamine

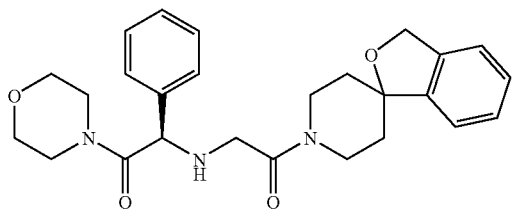

The title compound was prepared in analogy to example 71 using morpholine instead of azetin-3-ol. MS: m/z=450 [M+H]+.

Example 78

1-[(2R)-2-[{2-Oxo-2-(1'H,3H-spiro[2-benzofuran-1,4'-piperidin]-1'-yl)ethyl]amino}-2-phenylacetyl]piperidin-4-ol

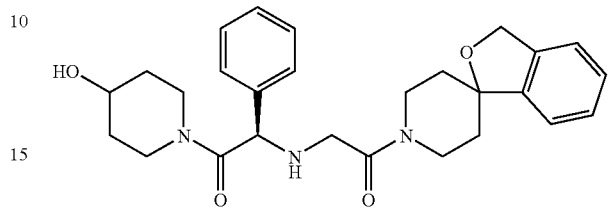

The title compound was prepared in analogy to example 71 using 4-hydroxypiperidine instead of azetin-3-ol. MS: m/z=464 [M+H]+.

Example 79

(1R)-2-(4-Methylpiperazin-1-yl)-2-oxo-N-[2-oxo-2-(1'H,3H-spiro[2-benzofuran-1,4'-piperidin]-1'-yl)ethyl]-1-phenylethanamine

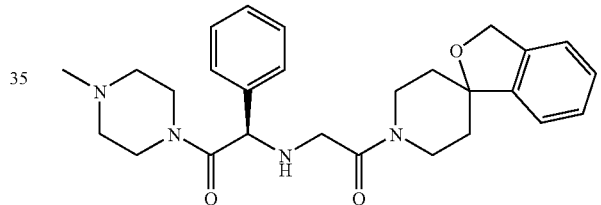

The title compound was prepared in analogy to example 71 using 1-methylpiperazine instead of azetin-3-ol. MS: m/z=463 [M+H]+.

Example 80

2-{4-[(2R)-2-{[2-Oxo-2-(1'H,3H-spiro[2-benzofuran-1,4'-piperidin]-1'-yl)ethyl]amino}-2-phenylacetyl]piperazin-1-yl}ethanol

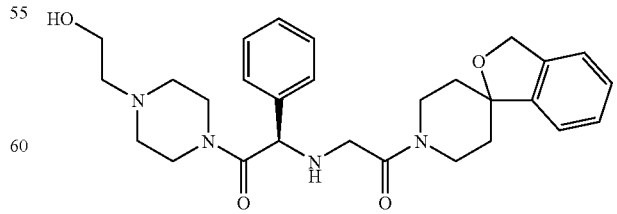

The title compound was prepared in analogy to example 71 using N-(2-hydroxyethyl)piperazine instead of azetin-3-ol. MS: m/z=493 [M+H]+.

Example 81

(1R)-2-[4-(Methylsulfonyl)piperazin-1-yl]-2-oxo-N-[2-oxo-2-(1'H,3H-spiro[2-benzofuran-1,4'-piperidin]-1'-yl)ethyl]-1-phenylethanamine

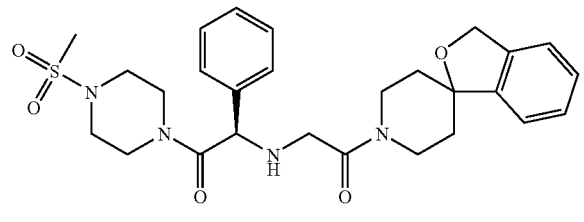

The title compound was prepared in analogy to example 71 using 1-methanesulfonyl-piperazine instead of azetin-3-ol. MS: m/z=493 [M+H]+.

Example 82

(2R)-2-[{2-Oxo-2-(1'H,3H-spiro[2-benzofuran-1,4'-piperidin]-1'-yl)ethyl]amino}-2-phenyl-N-pyridin-2-ylacetamide

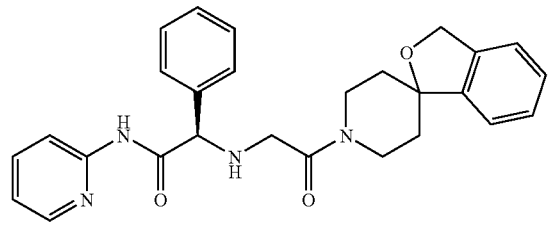

The title compound was prepared in analogy to example 71 using 2-aminopyridine instead of azetin-3-ol. MS: m/z=457 [M+H]+.

Example 83

(2R)-2-[{2-Oxo-2-(1'H,3H-spiro[2-benzofuran-1,4'-piperidin]-1'-yl)ethyl]amino}-2-phenyl-N-pyrimidin-2-ylacetamide

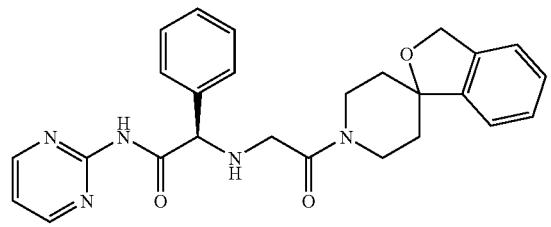

The title compound was prepared in analogy to example 71 using 2-aminopyrimidine instead of azetin-3-ol. MS: m/z=458 [M+H]+.

Example 84

(2R)-2-{[2-Oxo-2-(1'H,3H-spiro[2-benzofuran-1,4'-piperidin]-1'-yl)ethyl]amino}-2-phenyl-N-pyrazin-2-ylacetamide

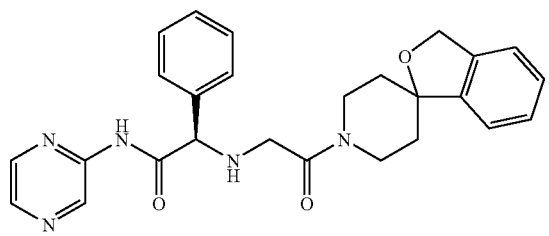

The title compound was prepared in analogy to example 71 using 2-aminopyrazine instead of azetin-3-ol. MS: m/z=458 [M+H]+.

Example 85

(1R)-2-(1,1-Dioxidothiomorpholin-4-yl)-2-oxo-N-[2-oxo-2-(1'H,3H-spiro[2-benzofuran-1,4'-piperidin]-1'-yl)ethyl]-1-phenylethanamine

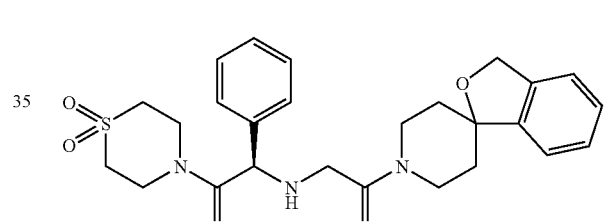

The title compound was prepared in analogy to example 71 using thiomorpholine 1,1-dioxide instead of azetin-3-ol. MS: m/z=498 [M+H]+.

Example 86

N,N-Dimethyl-4-[(2R)-2-{[2-oxo-2-(1'H,3H-spiro[2-benzofuran-1,4'-piperidin]-1'-yl)ethyl]amino}-2-phenylacetyl]piperazine-1-carboxamide

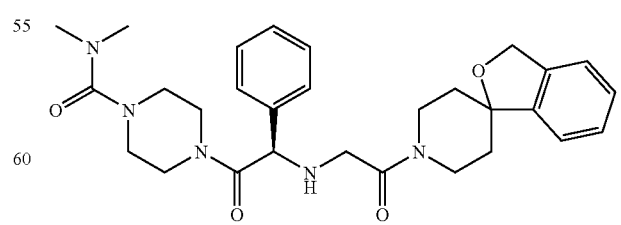

The title compound was prepared in analogy to example 71 using piperazine-1-carboxylic acid dimethylamide instead of azetin-3-ol. MS: m/z=520 [M+H]+.

Example 87

N,N-Dimethyl-4-[(2R)-2-{[2-oxo-2-(1'H,3H-spiro[2-benzofuran-1,4'-piperidin]-1'-yl)ethyl]amino}-2-phenylacetyl]piperazine-1-sulfonamide

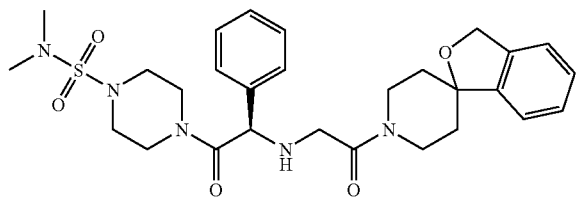

The title compound was prepared in analogy to example 71 using piperazine-1-sulfonic acid dimethylamide instead of azetin-3-ol. MS: m/z=556 [M+H]⁺.

Example 88

(2R)-N-Isoxazol-3-yl-2-{[2-oxo-2-(1'H,3H-spiro[2-benzofuran-1,4'-piperidin]-1'-yl)ethyl]amino}-2-phenylacetamide

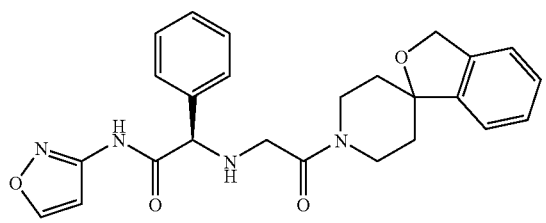

The title compound was prepared in analogy to example 71 using 3-aminoisoxazole instead of azetin-3-ol. MS: m/z=447 [M+H]⁺.

Example 89

{(2R)-1-[(2R)-2-(4-Chlorophenyl)-2-{[2-oxo-2-(1'H,3H-spiro[2-benzofuran-1,4'-piperidin]-1'-yl)ethyl]amino}acetyl]pyrrolidin-2-yl}methanol

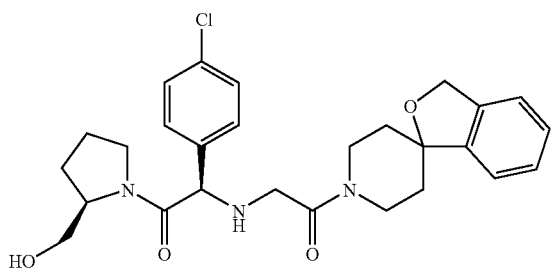

(2R)-{[(Allyloxy)carbonyl][2-oxo-2-(1'H,3H-spiro[2-benzofuran-1,4'-piperidin]-1'-yl)ethyl]amino}(4-chlorophenyl)acetic acid (50 mg, 0.1 mmol), (S)-(+)-2-hydroxymethyl)pyrrolidine (10 mg, 0.1 mmol), and O-(7-azabenzotriazol-1-yl)-N,N,N',N'-tetramethyluronium hexafluorophosphate (HATU) (57 mg, 0.15 mmol) were suspended in DCM (3 mL) and treated with triethylamine (0.05 mL, 0.35 mmol) for 5 h at 20° C. Pyrrolidine (0.09 mL, 1 mmol) and tetrakis(triphenylphosphine)palladium (1 mg, 0.01 mmol) were added and stirring at 20° C. was continued over night. Extraction with water gave a yellow oil, which was purified by chromatography on silica gel in AcOEt/MeOH 10:0 to 10:1 affording a light yellow foam (20 mg, 40%). MS: m/z=499 [M+H]⁺.

Example 90 tert-Butyl (2S)-2-[(2S)-2-(3-chlorophenyl)-2-{[2-oxo-2-(1'H,3H-spiro[2-benzofuran-1,4'-piperidin]-1'-yl)ethyl]amino}ethyl]pyrrolidine-1-carboxylate

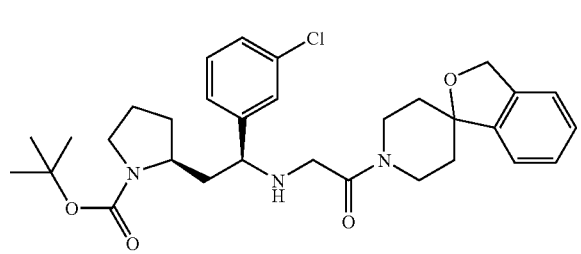

(R)-2-[2-(3-Chloro-phenyl)-2-oxo-ethyl]-pyrrolidine-1-carboxylic acid tert-butyl ester (1.67 g, 5.2 mmol) and 2-oxo-2-(1'H,3H-spiro[2-benzofuran-1,4'-piperidin]-1'-yl)ethanamine (1.27 g, 5.1 mmol) were transferred with DCM to a 50 mL flask and evaporated to dryness. The resulting neat mixture of oils was treated with tetraisopropyl orthotitanate (2 mL, 6.5 mmol) for 3 h at 20° C. The resulting suspension was diluted with ethanol (5 mL) and treated with sodium cyanoborohydride (117 mg, 3.5 mmol) at 20° C. for 14 h. The yellow suspension was cooled in ice, quenched with water (1 mL) and stirred for 15 min. and then filtered through celite and washed thoroughly with EtOH. The crude product (2.8 g) was purified by chromatography on silica gel in heptane/AcOEt 33:67. One obtained two epimers in order of elution: first 550 mg (19%) of the title compound, and second 1.2 g (41%) of its epimer, both as white foam. MS: m/z=554 [M+H]⁺.

Example 91

(1S)-1-(3-Chlorophenyl)-N-[2-oxo-2-(1'H,3H-spiro[2-benzofuran-1,4'-piperidin]-1'-yl)ethyl]-2-[(2S)-pyrrolidin-2-yl]ethanamine trifluoroacetate

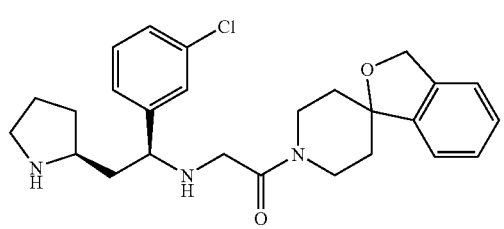

tert-Butyl (2S)-2-[(2S)-2-(3-chlorophenyl)-2-{[2-oxo-2-(1'H,3H-spiro[2-benzofuran-1,4'-piperidin]-1'-yl)ethyl]amino}ethyl]pyrrolidine-1-carboxylate (20 mg, 0.036 mmol) was stirred in a mixture of DCM and TFA at 20° C. for 2 h. The solvents were evporated to dryness. One obtained 22 mg (89%) of coloress oil. MS: m/z=455 [M+H]⁺.

Example 92

1'-[N-(Diphenylmethyl)glycyl]-3H-spiro[2-benzofuran-1,4'-piperidin]-3-one

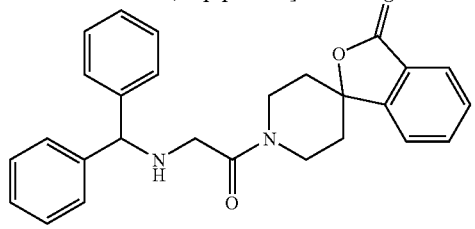

1'-(Chloroacetyl)-3H-spiro[2-benzofuran-1,4'-piperidine]-3-one (50 mg, 0.179 mmol)) and diphenylmethylamine (33 mg, 0.179 mmol) were dissolved in dry DMF (0.8 mL). Then triethylamine (0.074 mL, 0.536 mmol) was added and the reaction mixture was shaken at 25° C. for 2.5 days. Water (0.1 mL) was added and the whole mixture was directly purified by preparative HPLC on YMC-AQ column with a gradient of MeCN in water from 0-90% in 15 min. MS: m/z=427 [M+H]$^+$.

Example 93

N-(Diphenylmethyl)-N-methyl-2-oxo-2-(1'H,3H-spiro[2-benzofuran-1,4'-piperidin]-1'-yl)ethanamine

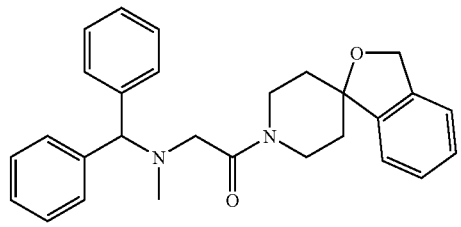

N-(Diphenylmethyl)-2-oxo-2-(1'H,3H-spiro[2-benzofuran-1,4'-piperidin]-1'-yl)ethanamine (Example 6) (90 mg, 0.218 mmol) was dissolved under nitrogen in DMF (1 mL), cooled in ice and treated with 55% sodium hydride (31 mg, 0.72 mmol) and iodomethane (0.045 mL, 0.72 mmol) for 24 h. Extraction: DCM, 10% Na$_2$CO$_3$. Chromatography: silica gel, heptane/AcOEt gradient 0-33%. One obtained a white solid (50 mg, 53%). MS: m/z=427 [M+H]$^+$.

The invention claimed is:

1. A compound of formula (I)

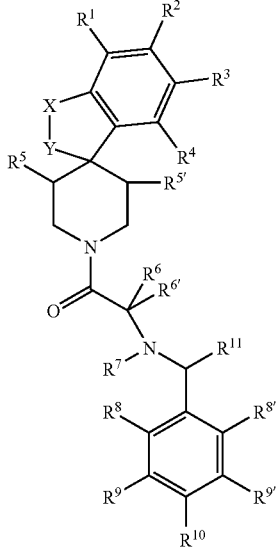

I wherein
X and Y are selected from the combinations of:
X is CH$_2$, and Y is O,
X is C=O, and Y is O,
X is O, and Y is CH$_2$,
and
X is O, and Y is C=O;
R$^1$, R$^2$, R$^3$, and R$^4$ are each independently hydrogen, halo, C$_{1-6}$-alkyl, C$_{1-6}$-haloalkyl, C$_{1-6}$-alkoxy or C$_{1-6}$-haloalkoxy;
R$^5$ and R$^{5'}$ are each independently hydrogen or methyl;
R$^6$ and R$^{6'}$ are each independently hydrogen or methyl;
R$^7$ is hydrogen, C$_{1-6}$-alkyl, —C(O)O—C$_{1-6}$-alkyl, or —C(O)O—C$_{2-6}$-alkenyl;
R$^8$, R$^{8'}$, R$^9$, R$^{9'}$, and R$^{10}$ are each independently selected from
hydrogen,
halogen,
C$_{1-4}$-alkyl, optionally substituted by CN or OH,
C$_{1-4}$-haloalkyl,
C$_{1-4}$-alkoxy,
C$_{1-4}$-haloalkoxy, and
hydroxy;
R$^{11}$ is hydrogen,
C$_{1-6}$-alkyl, optionally substituted by CN or OH,
—(CR$^i$R$^{ii}$)$_m$—R$^{iii}$,
wherein R$^i$ and R$^{ii}$ are each independently
H,
OH, or
C$_{1-4}$-alkyl, optionally substituted with OH,
or one R$^i$ and one R$^{ii}$ together with the carbon atom to which they are bound form a 3 to 5-membered cycloalkyl,
wherein m is from 0 to 4,
wherein R$^{iii}$ is
phenyl, naphthyl, 5- to 6-membered monocyclic or 9- to 10-membered bicyclic heteroaryl, 3- to 7-membered heterocycloalkyl, or 3- to 7-membered cycloalkyl,
each of which is optionally substituted by one or more A,
—C(O)—R$^{iv}$,
wherein R$^{iv}$ is
C$_{1-6}$-alkyl, optionally substituted with OH, or CN,
C$_{1-6}$-alkoxy,
hydroxy,
phenyl, naphthyl, benzyl, -Obenzyl, 5- to 6-membered monocyclic or 9- to 10-membered bicyclic heteroaryl, 3- to 7-membered heterocycloalkyl, or 3- to 7-membered cycloalkyl,
each of which is optionally substituted by one or more A,
—C(O)—NR$^f$R$^g$, or
—NR$^h$R$^j$,
wherein R$^f$, R$^g$, R$^h$ and R$^j$ are each independently selected from
hydrogen,
C$_{1-6}$-alkyl, and
phenyl or 5- to 6-membered heteroaryl,
optionally substituted with one or more A,
A is halo, nitro, hydroxy, cyano, =O, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, —(CH$_2$)$_x$—S(O)$_{0-2}$C$_{1-6}$-alkyl, —(C$_{1-6}$-alkylene)-O—C$_{1-6}$-alkyl, —(C$_{1-6}$-alkylene)-O—C$_{1-6}$-haloalkyl, —(CH$_2$)$_x$—NR$^a$R$^b$, —(CH$_2$)$_x$—C(O)NR$^a$R$^b$, —(CH$_2$)$_x$—S(O)$_2$NR$^a$R$^b$, —(CH$_2$)$_x$—R$^c$, —(CH$_2$)$_x$—O—R$^d$, —(CH$_2$)$_x$—S(O)$_{0-2}$—R$^d$, —(CH$_2$)$_x$—NR$^a$R$^d$, —(CH$_2$)$_x$—C(O)—NR$^a$R$^d$, —(CH$_2$)$_x$—C(O)R$^e$,
—(CH$_2$)$_x$—NR$^a$S(O)$_2$R$^e$, or —(CH$_2$)$_x$—NR$^a$(CH$_2$)$_x$C(O)R$^e$,
wherein
x is from 0 to 4;
R$^a$ and R$^b$ are each independently hydrogen or C$_{1-6}$-alkyl,
R$^c$ is phenyl, 5- to 6-membered heteroaryl, 3- to 7-membered heterocycloalkyl, or 3- to 7-membered cycloalkyl,
R$^d$ is phenyl or 5- to 6-membered heteroaryl,
R$^e$ is C$_{1-6}$-alkyl, C$_{1-6}$-alkoxy, phenyl, or 5- to 6-membered heteroaryl, 3- to 7-membered heterocycloalkyl, or 3- to 7-membered cycloalkyl,
   wherein phenyl, 5- to 6-membered heteroaryl, 3- to 7-membered heterocycloalkyl, or 3- to 7-membered cycloalkyl of R$^c$, R$^d$ or R$^e$ are optionally substituted with one, two, or three halo, C$_{1-6}$-haloalkyl, C$_{1-6}$-alkyl, or C$_{1-6}$-alkoxy,
or one of R$^8$ or R$^{8'}$ together with R$^{11}$ and the atoms to which they are bound form a 5-membered carbocycle, optionally anellated with benzo,
   wherein the benzo is optionally substituted with one, two or three substituents selected from halo, C$_{1-6}$-haloalkyl, C$_{1-6}$-alkyl, C$_{1-6}$-alkoxy, C$_{1-6}$-haloalkoxy, nitro, hydroxy, and cyano,
or a pharmaceutically acceptable salt thereof.

2. The compound of claim 1, wherein R$^1$, R$^2$, R$^3$, and R$^4$ are each independently hydrogen, halo, methyl, ethyl, trifluoromethyl, methoxy, ethoxy, or trifluoromethoxy.

3. The compound of claim 1, wherein R$^5$ and R$^{5'}$ are each hydrogen.

4. The compound of claim 1, wherein
R$^9$, R$^{9'}$, and R$^{10}$ are each independently selected from hydrogen, halogen, C$_{1-4}$-alkyl, C$_{1-4}$-hydroxyalkyl, C$_{1-4}$-cyanoalkyl, C$_{1-4}$-haloalkyl, C$_{1-4}$-alkoxy, C$_{1-4}$-haloalkoxy, and hydroxy, and R$^8$ and R$^{8'}$ are hydrogen.

5. The compound of claim 1, wherein R$^7$ is H or C$_{1-6}$-alkyl.

6. The compound of claim 1, wherein
R$^{11}$ is C$_{1-6}$-alkyl, optionally substituted by CN, OH or halogen,
—(CR$^i$R$^{ii}$)$_m$—R$^{iii}$,
   wherein R$^i$ and R$^{ii}$ are independently from each other
   H,
   OH,
   C$_{1-4}$-alkyl, optionally substituted with OH,
   wherein m is from 0 to 4,
   wherein R$^{iii}$ is
      phenyl, 5- to 6-membered monocyclic or 9- to 10-membered bicyclic heteroaryl, or 3- to 7-membered heterocycloalkyl,
      each of which is optionally substituted by one or more A,
   —C(O)—R$^{iv}$,
      wherein R$^{iv}$ is
         C$_{1-6}$-alkyl, optionally substituted with OH, or CN,
         C$_{1-6}$-alkoxy,
         hydroxy,
         phenyl, -Obenzyl, 5- to 6-membered monocyclic heteroaryl, or 3- to 7-membered heterocycloalkyl,
         each of which is optionally substituted by one or more A,
   —C(O)—NR$^f$R$^g$,
      wherein R$^f$, and R$^g$ are each independently selected from
         hydrogen,
         C$_{1-6}$-alkyl, and
         phenyl or 5- to 6-membered heteroaryl,
            optionally substituted with one or more A,
A is halo, nitro, hydroxy, cyano, =O, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, —(CH$_2$)$_x$—S(O)$_{0-2}$C$_{1-6}$-alkyl, —(C$_{1-6}$-alkylene)-O—C$_{1-6}$-alkyl, —(C$_{1-6}$-alkylene)-O—C$_{1-6}$-haloalkyl, —(CH$_2$)$_x$—NR$^a$R$^b$, —(CH$_2$)$_x$—C(O)NR$^a$R$^b$, —(CH$_2$)$_x$—S(O)$_2$NR$^a$R$^b$, —(CH$_2$)$_x$—R$^c$, —(CH$_2$)$_x$—O—R$^d$, —(CH$_2$)$_x$—S(O)$_{0-2}$—R$^d$, —(CH$_2$)$_x$—NR$^a$R$^d$, —(CH$_2$)$_x$—C(O)—NR$^a$R$^d$, —(CH$_2$)$_x$—C(O)R$^e$, —(CH$_2$)$_x$—NR$^a$S(O)$_2$R$^e$, or —(CH$_2$)$_x$—NR$^a$(CH$_2$)$_x$C(O)R$^e$,
wherein
x is from 0 to 4;
R$^a$ and R$^b$ are each independently hydrogen or C$_{1-6}$-alkyl,
R$^c$ is phenyl, 5- to 6-membered heteroaryl, 3- to 7-membered heterocycloalkyl, or 3- to 7-membered cycloalkyl,
R$^d$ is phenyl or 5- to 6-membered heteroaryl,
R$^e$ is C$_{1-6}$-alkyl, C$_{1-6}$-alkoxy, phenyl, or 5- to 6-membered heteroaryl, 3- to 7-membered heterocycloalkyl, or 3- to 7-membered cycloalkyl,
   wherein phenyl, 5- to 6-membered heteroaryl, 3- to 7-membered heterocycloalkyl, or 3- to 7-membered cycloalkyl of R$^c$, R$^d$ or R$^e$ are optionally substituted with one, two, or three halo, C$_{1-6}$-haloalkyl, C$_{1-6}$-alkyl, or C$_{1-6}$-alkoxy.

7. The compound of claim 1, wherein R$^1$, R$^2$, R$^3$, and R$^4$ are each hydrogen.

8. The compound of claim 1, wherein R$^2$ is fluoro, and R$^1$, R$^3$, and R$^4$ are hydrogen.

9. The compound of claim 1, wherein R$^1$, R$^2$, R$^3$, and R$^4$ are independently hydrogen and methyl.

10. The compound of claim 1, wherein R$^6$ and R$^{6'}$ are each hydrogen.

11. The compound of claim 1, wherein R$^8$, R$^{8'}$, R$^9$, R$^{9'}$, and R$^{10}$ are each independently selected from the group consisting of hydrogen, halogen, C$_{1-4}$-alkyl, C$_{1-4}$-haloalkyl, C$_{1-4}$-alkoxy, C$_{1-4}$-haloalkoxy, and hydroxyl.

12. The compound of claim 1, wherein R$^8$, R$^{8'}$, R$^9$, R$^{9'}$ and R$^{10}$ are each independently selected from the group consisting of hydrogen, halogen, methyl, ethyl, trifluoromethyl, methoxy, and hydroxyl.

13. The compound of claim 1, wherein R$^9$, R$^{9'}$, and R$^{10}$ are each independently selected from the group consisting of hydrogen, halogen, methyl, ethyl, trifluoromethyl, and R8 and R8' are each hydrogen.

14. The compound of claim 1, wherein X is CH$_2$ and Y is O.

15. The compound of claim 1, wherein X is C=O and Y is O.

16. The compound of claim 1, wherein X is O and Y is CH$_2$.

17. The compound of claim 1, wherein X is O and Y is C=O.

18. The compound of claim 1, selected from the group consisting of
(RS)-N-[(4-Chlorophenyl)(phenyl)methyl]-2-oxo-2-(1'H,3H-spiro[2-benzofuran-1,4'-piperidin]-1'-yl)ethanamine,
N-[(+)-(4-chlorophenyl)(phenyl)methyl]-2-oxo-2-(1'H,3H-spiro[2-benzofuran-1,4'-piperidin]-1'-yl)ethanamine,
N-(Diphenylmethyl)-2-oxo-2-(1'H,3H-spiro[2-benzofuran-1,4'-piperidin]-1'-yl)ethanamine,
(RS)—N-[(3-Chlorophenyl)(phenyl)methyl]-2-oxo-2-(1'H,3H-spiro[2-benzofuran-1,4'-piperidin]-1'-yl)ethanamine,
(RS)—N-[(3,4-Dichlorophenyl)(phenyl)methyl]-2-oxo-2-(1'H,3H-spiro[2-benzofuran-1,4'-piperidin]-1'-yl)ethanamine, (RS)-2-Oxo-N-{phenyl[3-(trifluoromethyl)phenyl]methyl}-2-(1'H,3H-spiro[2-benzofuran-1,4'-piperidin]-1'-yl)ethanamine, (RS)—N-{(4-Fluorophenyl)[3-(trifluoromethyl)phenyl]methyl}-2-oxo-2-(1'H,3H-spiro[2-benzofuran-1,4'-piperidin]-1'-yl)ethanamine, (RS)-2-Oxo-N-{phenyl[4-(trifluoromethyl)phenyl]methyl}-2-(1'H,3H-spiro[2-benzofuran-1,4'-piperidin]-1'-yl)ethanamine, (RS)-2-Oxo-N-[phenyl(2-thienyl)methyl]-2-(1'H,3H-spiro[2-benzofuran-1,4'-piperidin]-1'-yl)ethanamine, (RS)-2-Oxo-N-[phenyl(pyridin-2-yl)methyl]-2-(1'H,3H-spiro[2-benzofuran-1,4'-piperidin]-1'-yl)ethanamine, (RS)—N-[(4-Fluorophenyl)(2-thienyl)methyl]-2-oxo-2-(1'H,3H-spiro[2-benzofuran-1,4'-piperidin]-1'-yl)ethanamine, (RS)—N-[(3,5-Dimethyl-1H-pyrazol-4-yl)(phenyl)methyl]-2-oxo-2-(1'H,3H-spiro[2-benzofuran-1,4'-piperidin]-1'-yl)ethanamine, (2R)—N-(4-Chlorophenyl)-2-{[2-oxo-2-(1'H,3H-spiro[2-benzofuran-1,4'-piperidin]-1'-yl)ethyl]amino}-2-phenylacetamide, (RS)—N-[(3-Methylphenyl)(phenyl)methyl]-2-oxo-2-(1'H,3H-spiro[2-benzofuran-1,4'-piperidin]-1'-yl)ethanamine, (RS)-4-Chloro-2-[{[2-oxo-2-(1'H,3H-spiro[2-benzofuran-1,4'-piperidin]-1'yl)ethyl]amino}(phenyl)methyl]phenol, (1S,2R)-2-(4-Chlorophenyl)-1-(4-morpholin-4-ylphenyl)-2-{[2-oxo-2-(1'H,3H-spiro[2-benzofuran-1,4'-piperidin]-1'-yl)ethyl]amino}ethanol, (1RS,2RS)-1-(4-Chlorophenyl)-1-{[2-oxo-2-(1'H,3H-spiro[2-benzofuran-1,4'-piperidin]-1'-yl)ethyl]amino}-2-pyridin-2-yl-propan-2-ol, 1-(4-Chlorophenyl)-1-{[2-oxo-2-(1'H,3H-spiro[2-benzofuran-1,4'-piperidin]-1'-yl)ethyl]amino}-2-pyridin-4-ylpropan-2-ol, (RS)—N-[(3-Chlorophenyl){3-[(4-methylpiperazin-1-yl)methyl]phenyl}methyl]-2-oxo-2-(1'H,3H-spiro[2-benzofuran-1,4'-piperidin]-1'-yl)ethanamine, (RS)—N-[(3-Chlorophenyl)(1,3-oxazol-2-yl)methyl]-2-oxo-2-(1'H,3H-spiro[2-benzofuran-1,4'-piperidin]-1'-yl)ethanamine, 1-[(2R)-2-{[2-Oxo-2-(1'H,3H-spiro[2-benzofuran-1,4'-piperidin]-1'-yl)ethyl]amino}-2-phenylacetyl]azetidin-3-ol, 1'-[N-(Diphenylmethyl)glycyl]-3H-spiro[2-benzofuran-1,4'-piperidin]-3-one, and N-(Diphenylmethyl)-N-methyl-2-oxo-2-(1'H,3H-spiro[2-benzofuran-1,4'-piperidin]-1'-yl)ethanamine.

19. A pharmaceutical composition comprising a therapeutically effective amount of a compound of formula I

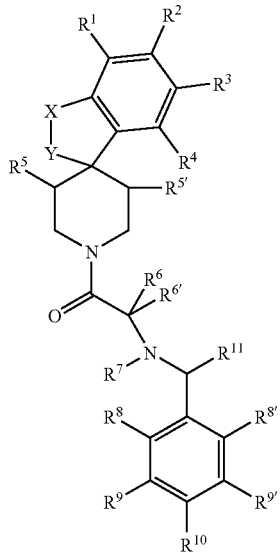

wherein
X and Y are selected from the combinations of:
X is $CH_2$, and Y is O,
X is C=O, and Y is O,
X is O, and Y is $CH_2$,
and
X is O, and Y is C=O;
$R^1$, $R^2$, $R^3$, and $R^4$ are each independently hydrogen, halo, $C_{1-6}$-alkyl, $C_{1-6}$-haloalkyl, $C_{1-6}$-alkoxy or $C_{1-6}$-haloalkoxy;
$R^5$ and $R^{5'}$ are each independently hydrogen or methyl;
$R^6$ and $R^{6'}$ are each independently hydrogen or methyl;
$R^7$ is hydrogen, $C_{1-6}$-alkyl, —C(O)O—$C_{1-6}$-alkyl, or —C(O)O—$C_{2-6}$-alkenyl;
$R^8$, $R^{8'}$, $R^9$, $R^{9'}$, and $R^{10}$ are each independently selected from
hydrogen,
halogen,
$C_{1-4}$-alkyl, optionally substituted by CN or OH,
$C_{1-4}$-haloalkyl,
$C_{1-4}$-alkoxy,
$C_{1-4}$-haloalkoxy, and
hydroxy;
$R^{11}$ is hydrogen,
$C_{1-6}$-alkyl, optionally substituted by CN or OH,
—$(CR^iR^{ii})_m$—$R^{iii}$,
wherein $R^i$ and $R^{ii}$ are each independently
H,
OH, or
$C_{1-4}$-alkyl, optionally substituted with OH,
or one $R^i$ and one $R^{ii}$ together with the carbon atom to which they are bound form a 3 to 5-membered cycloalkyl,
wherein m is from 0 to 4,
wherein $R^{iii}$ is
phenyl, naphthyl, 5- to 6-membered monocyclic or 9- to 10-membered bicyclic heteroaryl, 3- to 7-membered heterocycloalkyl, or 3- to 7-membered cycloalkyl,
each of which is optionally substituted by one or more A, —C(O)—$R^{iv}$,
  wherein $R^{iv}$ is
    $C_{1-6}$-alkyl, optionally substituted with OH, or CN,
    $C_{1-6}$-alkoxy,
    hydroxy,
    phenyl, naphthyl, benzyl, -Obenzyl, 5- to 6-membered monocyclic or 9- to 10-membered bicyclic heteroaryl, 3- to 7-membered heterocycloalkyl, or 3- to 7-membered cycloalkyl, each of which is optionally substituted by one or more A,
—C(O)—$NR^{f}R^{g}$, or
—$NR^{h}R^{j}$,
  wherein $R^{f}$, $R^{g}$, $R^{h}$ and $R^{j}$ are each independently selected from
    hydrogen,
    $C_{1-6}$-alkyl, and
    phenyl or 5- to 6-membered heteroaryl, optionally substituted with one or more A,
A is halo, nitro, hydroxy, cyano, =O, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —$(CH_2)_x$—$S(O)_{0-2}C_{1-6}$-alkyl, —$(C_{1-6}$-alkylene)-O—$C_{1-6}$-alkyl, —$(C_{1-6}$-alkylene)-O—$C_{1-6}$-haloalkyl, —$(CH_2)_x$—$NR^{a}R^{b}$, —$(CH_2)_x$—$C(O)NR^{a}R^{b}$, —$(CH_2)_x$—$S(O)_2NR^{a}R^{b}$, —$(CH_2)_x$—$R^{c}$, —$(CH_2)_x$—O—$R^{d}$, —$(CH_2)_x$—$S(O)_{0-2}$—$R^{d}$, —$(CH_2)_x$—$NR^{a}R^{d}$, —$(CH_2)_x$—$C(O)$—$NR^{a}R^{d}$, —$(CH_2)_x$—$C(O)R^{e}$, —$(CH_2)_x$—$NR^{a}S(O)_2R^{e}$, or —$(CH_2)_x$—$NR^{a}(CH_2)_xC(O)R^{e}$,
wherein
  x is from 0 to 4;
  $R^{a}$ and $R^{b}$ are each independently hydrogen or $C_{1-6}$-alkyl,
  $R^{c}$ is phenyl, 5- to 6-membered heteroaryl, 3- to 7-membered heterocycloalkyl, or 3- to 7-membered cycloalkyl,
  $R^{d}$ is phenyl or 5- to 6-membered heteroaryl,
  $R^{e}$ is $C_{1-6}$-alkyl, $C_{1-6}$-alkoxy, phenyl, or 5- to 6-membered heteroaryl, 3- to 7-membered heterocycloalkyl, or 3- to 7-membered cycloalkyl,
    wherein phenyl, 5- to 6-membered heteroaryl, 3- to 7-membered heterocycloalkyl, or 3- to 7-membered cycloalkyl of $R^{c}$, $R^{d}$ or $R^{e}$ are optionally substituted with one, two, or three halo, $C_{1-6}$-haloalkyl, $C_{1-6}$-alkyl, or $C_{1-6}$-alkoxy,
or one of $R^{8}$ or $R^{8'}$ together with $R^{11}$ and the atoms to which they are bound form a 5-membered carbocycle, optionally anellated with benzo,
  wherein the benzo is optionally substituted with one, two or three substituents selected from halo, $C_{1-6}$-haloalkyl, $C_{1-6}$-alkyl, $C_{1-6}$-alkoxy, $C_{1-6}$-haloalkoxy, nitro, hydroxy, and cyano,
or a pharmaceutically acceptable salt thereof and a pharmaceutically acceptable carrier.

* * * * *